(12) United States Patent  (10) Patent No.:  US 8,211,301 B2
Safar et al.  (45) Date of Patent:  Jul. 3, 2012

(54) STRUCTURE AND METHOD FOR HANDLING MAGNETIC PARTICLES IN BIOLOGICAL ASSAYS

(75) Inventors: Scott G. Safar, Burlington, WI (US); Charles M. Galitz, Kenosha, WI (US); Stephen L. Herchenbach, Antioch, IL (US); Chadwick M. Dunn, Janesville, WI (US); Larry L. McDowell, Beach Park, IL (US)

(73) Assignee: Abbott Laboratories, Des Plaines, IL (US)

( * ) Notice: Subject to any disclaimer, the term of this patent is extended or adjusted under 35 U.S.C. 154(b) by 0 days.

(21) Appl. No.: 12/660,930

(22) Filed: Mar. 4, 2010

(65) Prior Publication Data

US 2010/0227387 A1  Sep. 9, 2010

Related U.S. Application Data

(62) Division of application No. 10/512,033, filed as application No. PCT/US03/12930 on Apr. 25, 2003, now Pat. No. 7,718,072.

(60) Provisional application No. 60/375,766, filed on Apr. 26, 2002.

(51) Int. Cl.
*B03C 1/02* (2006.01)
*C12P 19/34* (2006.01)
*C12Q 1/68* (2006.01)

(52) U.S. Cl. ...... 210/222; 435/6.1; 435/91.2; 435/287.2; 435/287.3; 422/509; 422/527

(58) Field of Classification Search ............ 435/6, 91.2, 435/287.2, 287.3, 6.1; 422/509, 527; 210/222
See application file for complete search history.

(56) References Cited

U.S. PATENT DOCUMENTS

| | | |
|---|---|---|
| 3,219,318 A | 11/1965 | Hershler |
| 3,433,465 A | 3/1969 | Szpur |
| 3,595,531 A | 7/1971 | Williams et al. |
| 3,985,549 A | 10/1976 | Rheinlander et al. |
| 3,995,835 A | 12/1976 | Cichy et al. |
| 4,310,253 A | 1/1982 | Sada et al. |
| 4,728,500 A | 3/1988 | Higo |
| 4,895,650 A | 1/1990 | Wang |
| 5,222,808 A | 6/1993 | Sugarman et al. |
| 5,234,809 A | 8/1993 | Boom et al. |
| 5,272,092 A | 12/1993 | Hamasaki et al. |
| 5,352,036 A | 10/1994 | Haber et al. |
| 5,458,785 A | 10/1995 | Howe et al. |
| 5,536,475 A | 7/1996 | Moubayed et al. |
| 5,578,201 A | 11/1996 | Collier et al. |
| 5,589,394 A | 12/1996 | Kim et al. |
| 5,601,234 A | 2/1997 | Larue |
| 5,631,165 A | 5/1997 | Chupp et al. |
| 5,631,730 A | 5/1997 | Chupp et al. |
| 5,656,499 A | 8/1997 | Chupp et al. |

(Continued)

FOREIGN PATENT DOCUMENTS

EP  0905520  3/1999

(Continued)

*Primary Examiner* — David A Reifsnyder
(74) *Attorney, Agent, or Firm* — McDermott Will & Emery LLP

(57) ABSTRACT

Magnetic handling structure (1*a*) comprising a retractable magnet (4) and a probe (3) for the manipulation of magnetic particles in biological samples and methods of handling magnetic particles in biological samples.

3 Claims, 57 Drawing Sheets

U.S. PATENT DOCUMENTS

| | | |
|---|---|---|
| 5,702,950 A | 12/1997 | Tajima |
| 5,770,461 A | 6/1998 | Sakazume et al. |
| 5,779,907 A | 7/1998 | Yu |
| 5,795,784 A | 8/1998 | Arnquist et al. |
| D397,938 S | 9/1998 | Graham et al. |
| 5,812,419 A | 9/1998 | Chupp et al. |
| D401,697 S | 11/1998 | Cloonan et al. |
| D401,699 S | 11/1998 | Herchenbach et al. |
| 5,856,194 A | 1/1999 | Arnquist et al. |
| 5,891,734 A | 4/1999 | Gill et al. |
| 6,033,574 A | 3/2000 | Siddiqi |
| 6,165,778 A | 12/2000 | Kedar |
| 6,176,609 B1 | 1/2001 | Cleveland et al. |
| 6,228,268 B1 | 5/2001 | Siddiqi |
| 6,335,166 B1 * | 1/2002 | Ammann et al. ............ 435/6.11 |
| 6,357,907 B1 | 3/2002 | Cleveland et al. |
| 6,382,827 B1 | 5/2002 | Gebrian |
| 6,413,780 B1 | 7/2002 | Bach et al. |
| 6,467,946 B1 | 10/2002 | Gebrian |
| 6,500,343 B2 | 12/2002 | Siddiqi |
| 6,579,453 B1 | 6/2003 | Bachler et al. |
| 6,616,730 B1 | 9/2003 | Bienvenu |
| 6,689,615 B1 | 2/2004 | Murto et al. |
| 6,764,859 B1 | 7/2004 | Kreuwel et al. |
| 7,718,072 B2 | 5/2010 | Safar et al. |
| 2002/0008053 A1 | 1/2002 | Hansen et al. |
| 2003/0006193 A1 | 1/2003 | Ikeda et al. |
| 2003/0170686 A1 | 9/2003 | Hoet et al. |
| 2004/0013584 A1 | 1/2004 | Arndt et al. |
| 2004/0157224 A1 | 8/2004 | Roh et al. |
| 2004/0235196 A1 | 11/2004 | Colin |
| 2005/0013741 A1 | 1/2005 | a'Brassard |
| 2005/0286342 A1 | 12/2005 | Garcia et al. |
| 2006/0024776 A1 | 2/2006 | McMillian |
| 2007/0155024 A1 | 7/2007 | Miethe et al. |

FOREIGN PATENT DOCUMENTS

| | | |
|---|---|---|
| EP | 0970742 | 1/2000 |
| EP | 1655071 | 5/2006 |
| EP | 1655071 | 11/2010 |
| GB | 1113046 | 5/1968 |
| JP | 53-129373 | 11/1978 |
| JP | 60058235 | 4/1985 |
| JP | 6327476 | 11/1994 |
| JP | 7107999 | 4/1995 |
| JP | 2000-88803 | 3/2000 |
| JP | 2000-254472 | 9/2000 |
| JP | 2001-521622 | 11/2001 |
| JP | 2005-205306 | 8/2005 |
| WO | WO 93/25913 | 12/1993 |
| WO | WO 99/61919 | 12/1999 |
| WO | WO 00/09991 | 2/2000 |
| WO | 00/23807 | 4/2000 |
| WO | WO 00/21668 | 4/2000 |
| WO | WO 00/23807 | 4/2000 |
| WO | WO 00/72968 | 12/2000 |
| WO | WO 00/73412 | 12/2000 |
| WO | WO 01/05510 | 1/2001 |
| WO | WO 01/49419 | 7/2001 |
| WO | WO 02/063042 | 8/2002 |
| WO | 03/044537 | 5/2003 |
| WO | WO 03/044537 | 5/2003 |
| WO | WO 03/090897 | 11/2003 |
| WO | WO 2004/050227 | 6/2004 |
| WO | WO 2004/057304 | 7/2004 |
| WO | WO 2005/037440 | 4/2005 |
| WO | WO 2006/010584 | 2/2006 |

* cited by examiner

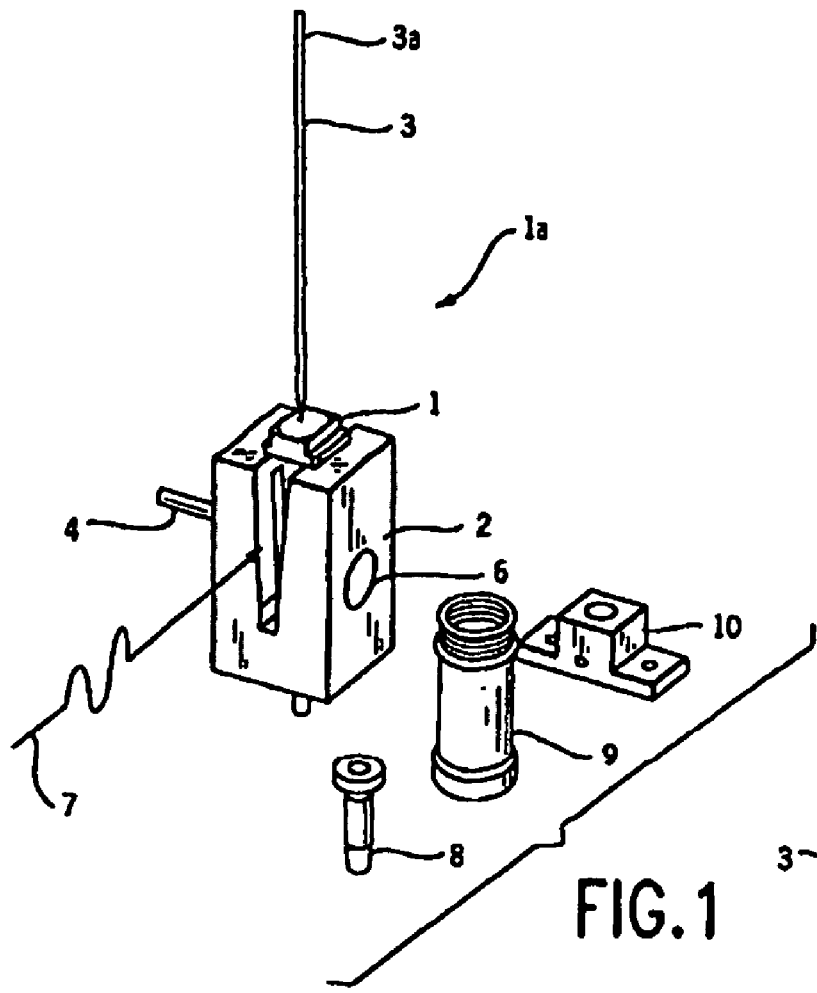
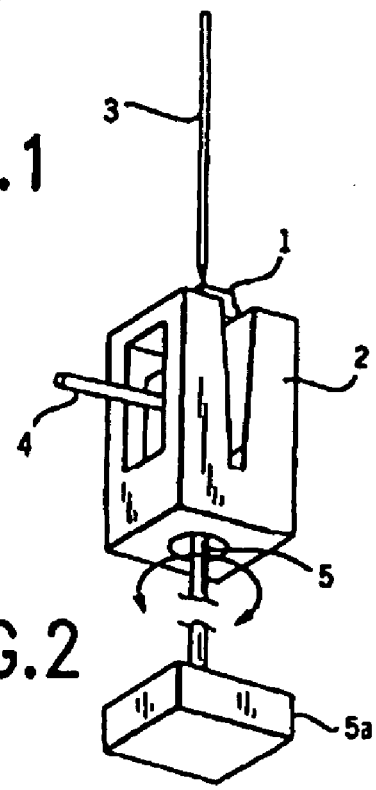
FIG. 1
FIG. 2

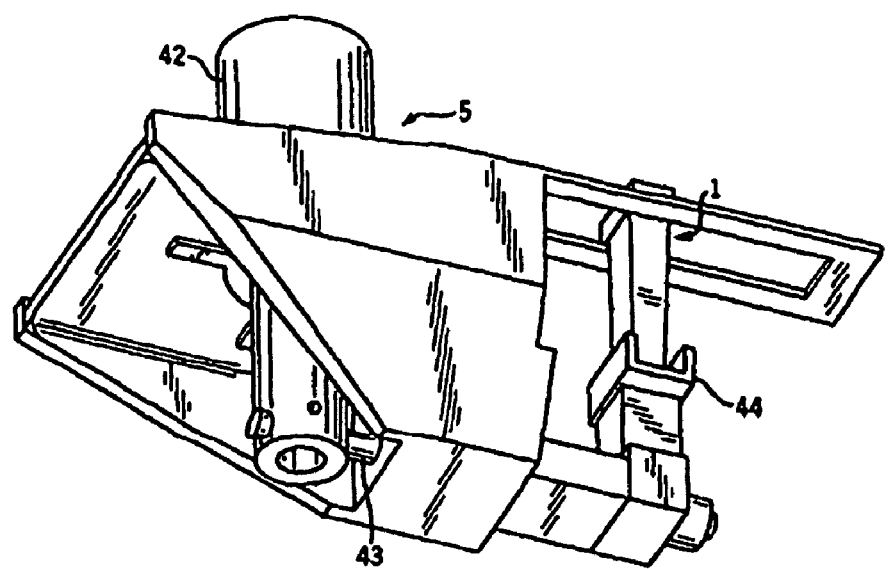
FIG. 13
FIG. 15
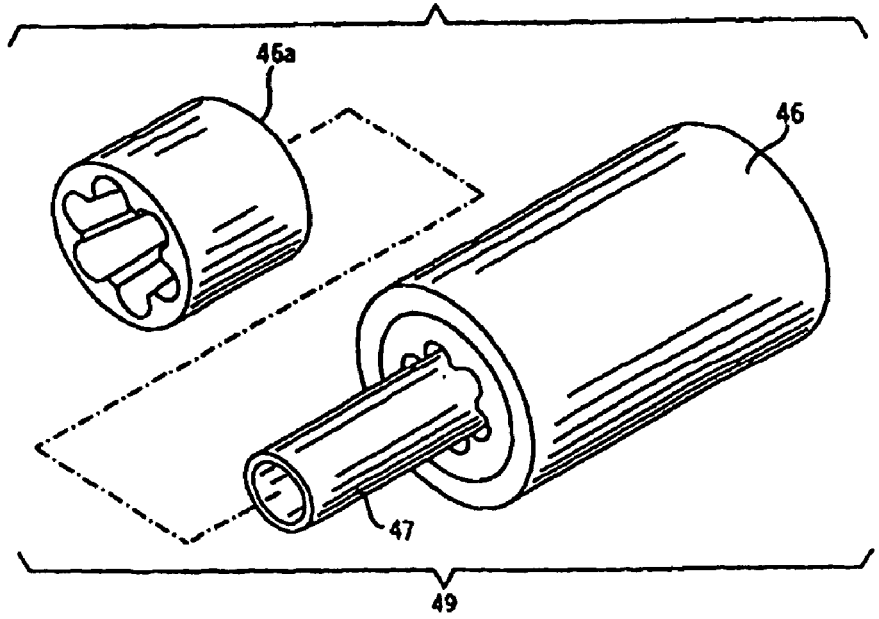

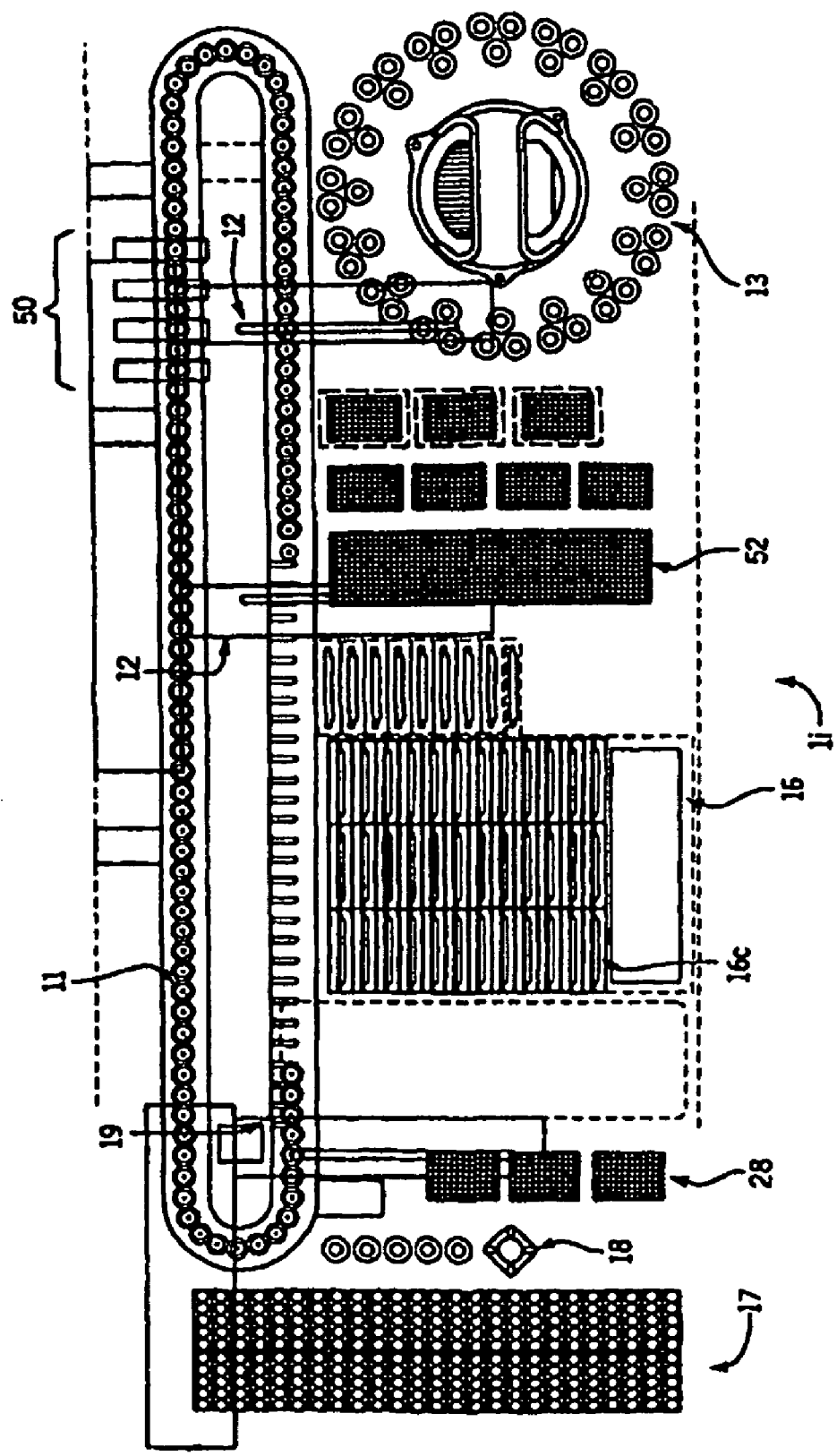

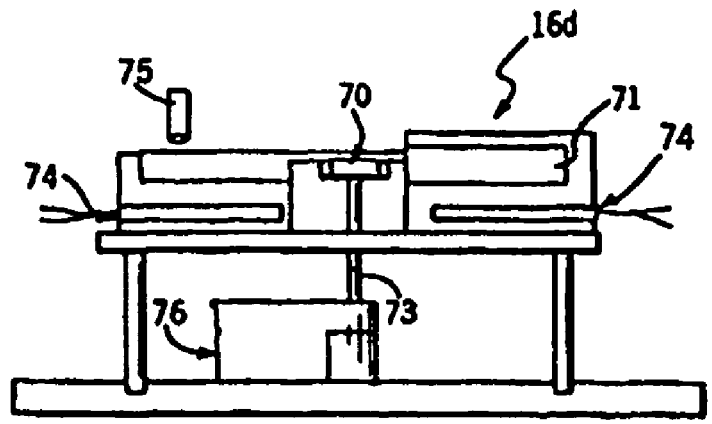
FIG. 31
FIG. 32A
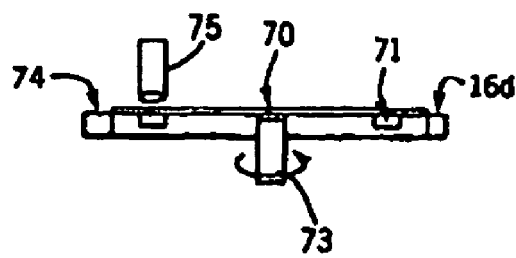
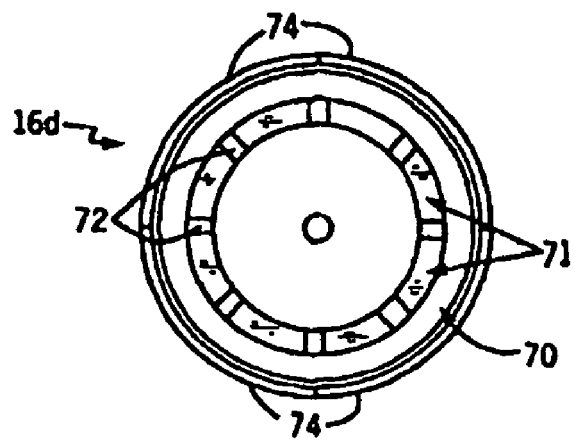
FIG. 32B

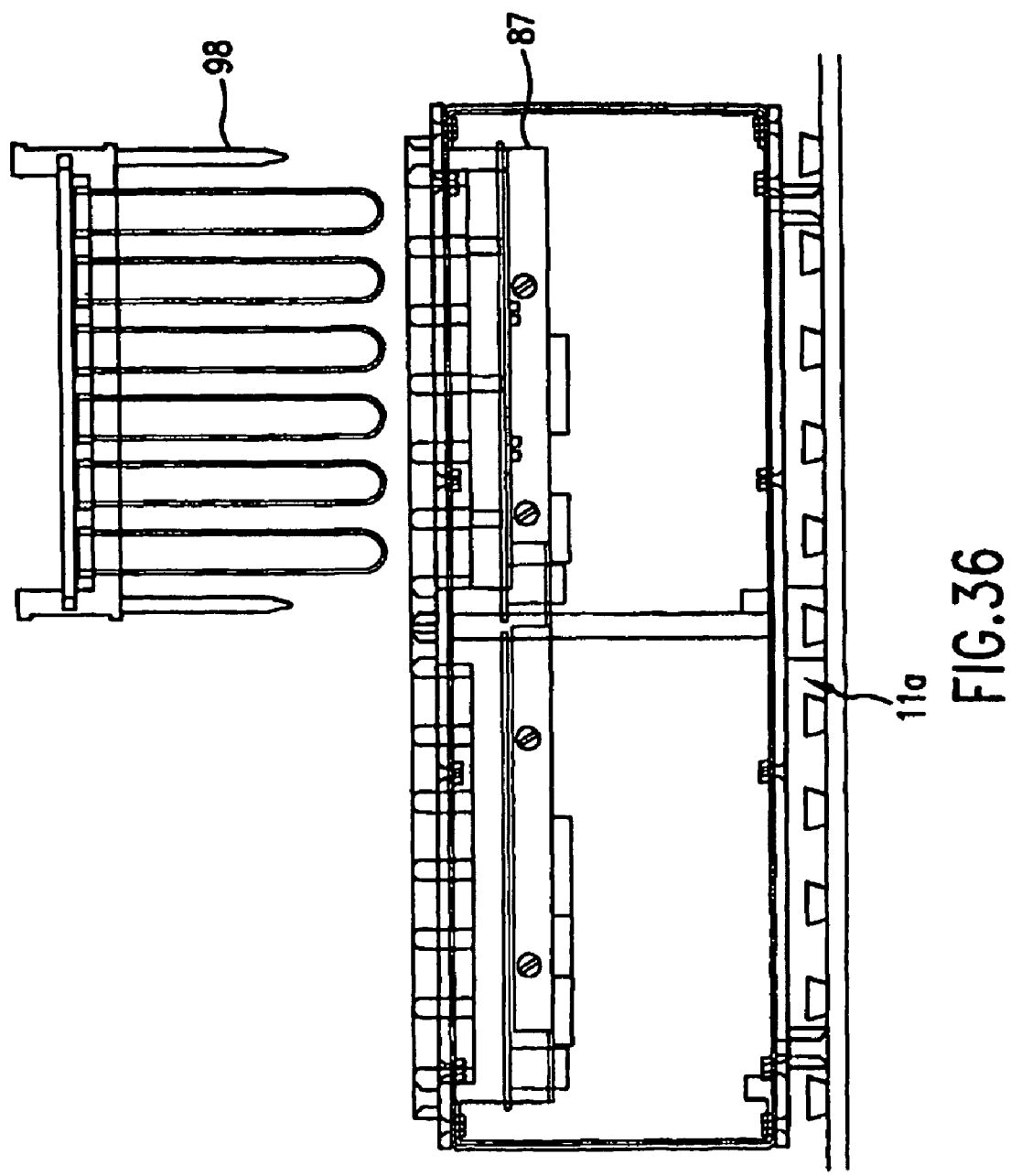

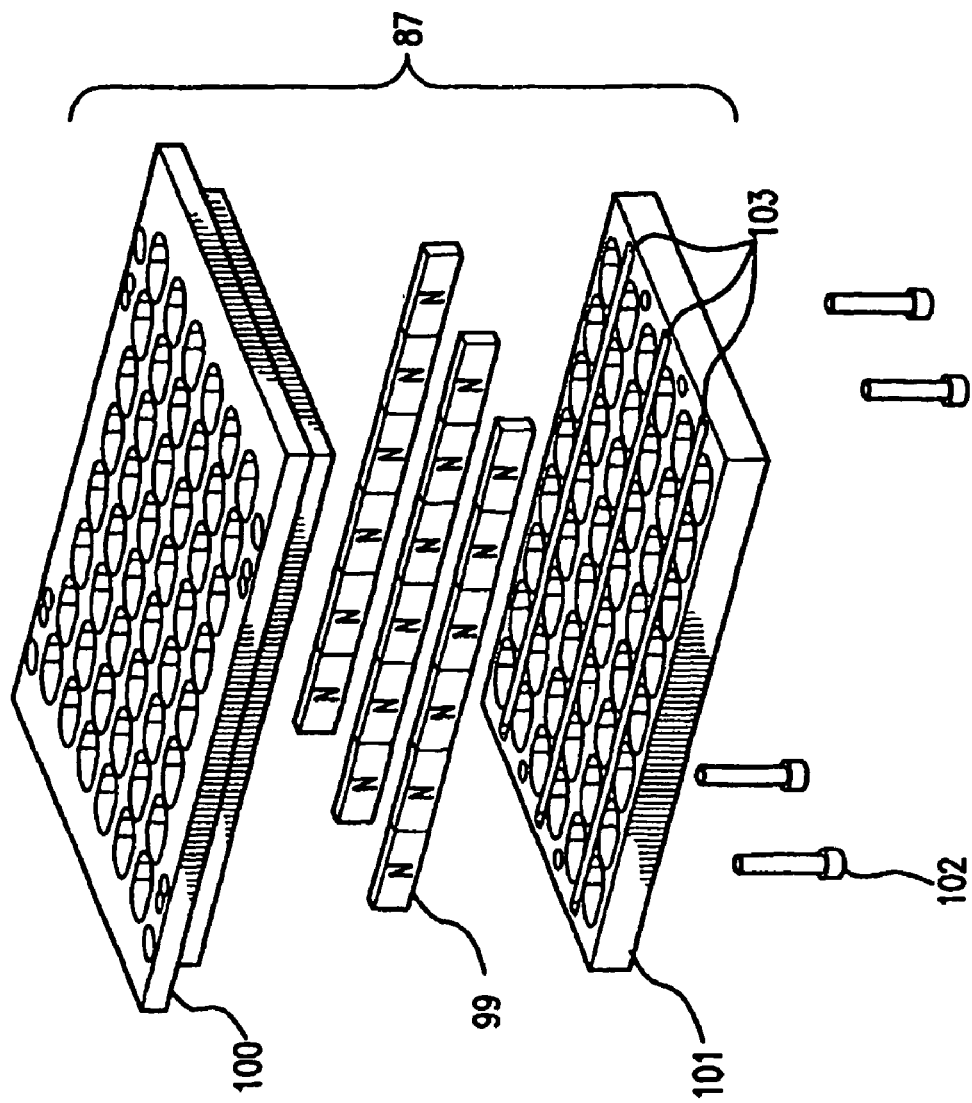

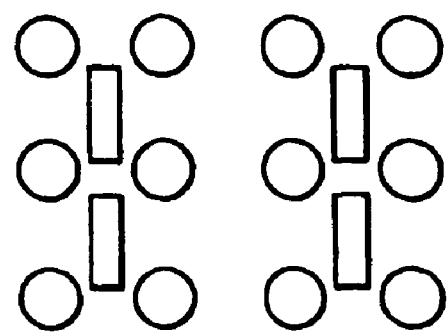
FIG. 47
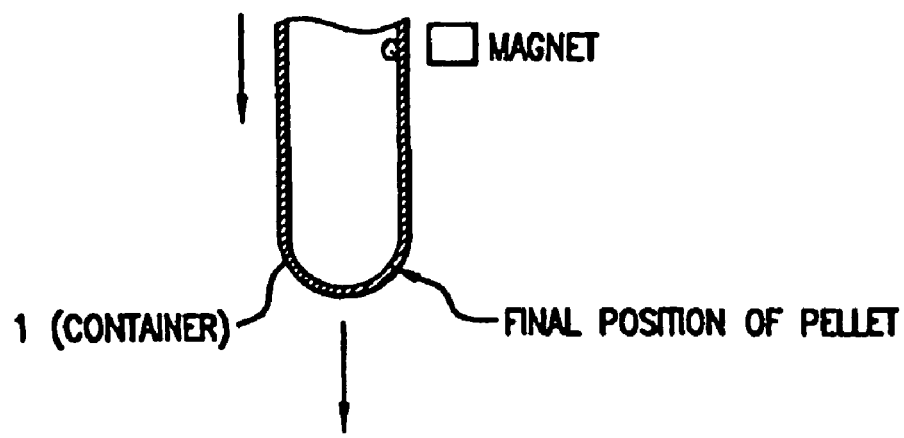
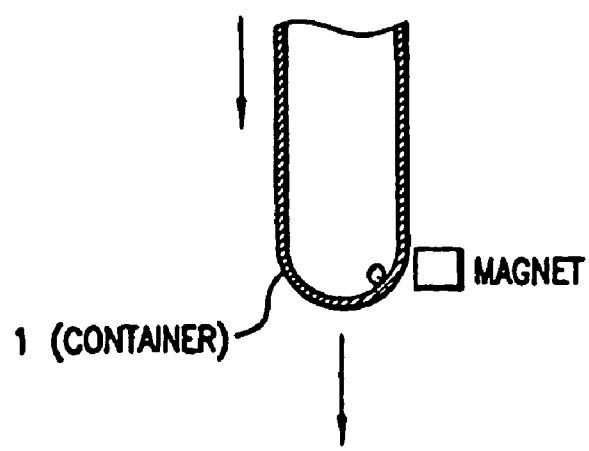
FIG. 48

STRUCTURE AND METHOD FOR HANDLING MAGNETIC PARTICLES IN BIOLOGICAL ASSAYS

CROSS-REFERENCE TO RELATED APPLICATIONS

This application is a divisional of U.S. patent application Ser. No. 10/512,033, filed Sep. 15, 2005, now U.S. Pat. No. 7,718,072 which claims priority to PCT Patent Application No. PCT/US03/12930, filed Apr. 25, 2003, which claims priority to U.S. provisional application No. 60/375,766, filed Apr. 26, 2002 both of which are incorporated by reference herein.

BACKGROUND

The following relates generally to a structure and a method for determining an item of interest in a sample. More specifically, the following relates to determining an item of interest that may be or include all or portions of a specific region of DNA, RNA, fragments, complements, peptides, polypeptides, enzymes, prions, proteins, messenger RNA, transfer RNA, mitochondrial RNA or DNA, antibodies, antigens, allergens, parts of biological entities such as cells, virons or the like, surface proteins, functional equivalents of the above, etc.

To provide information about a patient's health, a number of tests can be performed on a patient sample, such as the patient's bodily fluids. These bodily fluids may include serum, whole blood, urine, swabs, plasma, cerebra-spinal fluid, lymph fluids, tissue solids, etc. The tests performed on the patient's bodily fluids can determine an item of interest, such as those stated above, in the bodily fluids. Based on the determination of the item of interest in the patient's bodily fluids, information about the patient's health status can be obtained.

SUMMARY OF THE INVENTION

In one aspect of the invention, a method of performing a determination of an item of interest in a sample is provided using a single structure. A sample is provided accessible to the single structure. A first container for processing the sample is placed in a first process path on the single structure. The sample is transferred to the first container in the first process path. A reagent is added to the first container in the first process path. Contents of the first container is mixed in the first process path. The item of interest in the sample is separated from the contents of the first container in the first process path. The separated item of interest in the sample is transferred from the first container in the first process path to a second container in a second process path on the single structure. Contents of the second container is brought to a first temperature different from a temperature of the first process path in the second process path. The item of interest in the second container is detected in the second process path.

In another method, a sample is transferred to a first container in a first process path on a single structure. An item of interest in the sample is separated from the contents of the first container in the first process path. The separated item of interest in the sample is transferred from the first container in the first process path to a second container in a second process path on the single structure. Contents of the second container is brought to a first temperature different from a temperature of the first process path in the second process path. The item of interest is detected in the second container in the second process path.

In an additional method, a sample is transferred to a container in a process path on the single structure. An item of interest in the sample is separated from the contents of the container in the process path. Contents of the container is brought to a first temperature in the process path. Contents of the container is brought to a second temperature different from the first temperature in the process path. The item of interest is detected in the container in the process path.

In a further method, a sample is transferred to a first container in a first process path on the single structure. The sample is transferred from the first container in the first process path to a second container in a second process path on the single structure. Contents of the second container is brought to a first temperature different from a temperature of the first process path in the second process path. The item of interest is detected in the second container in the second process path.

In yet a further method, a sample is transferred to a container in a process path on the single structure. Contents of the container is brought to a first temperature on the process path on the single structure. Contents of the container is brought to a second temperature different from the first temperature in the process path on the single structure. The item of interest is detected in the container in the process path on the single structure.

BRIEF DESCRIPTION OF DRAWINGS

FIG. 1 is a perspective view of a container structure described herein;

FIG. 2 is a perspective view of the container structure of FIG. 1;

FIG. 13 illustrates engagement of the container of FIG. 12E with a mixer;

FIG. 15 is an exploded perspective view of a pipettor for use with the apparatus of FIGS. 3A and 3B;

FIG. 26 is a top view of yet a further apparatus similar to the apparatus of FIGS. 3A and 3B;

FIG. 31 is a sectional view of the module of FIG. 30A;

FIG. 32A is a sectional view of another thermal cycling module;

FIG. 32B is a top view of the module of FIG. 32A;

FIG. 36 is another view of alternate sample prep process area of FIG. 35;

FIG. 36A is a perspective view of magnets contained in FIG. 36;

FIG. 47 is an illustration of a pattern of magnets and tube holders that comprises two copies of the pattern shown in FIG. 46 and places additional tube holders about the periphery of the assembly to take fuller advantage of the magnetic flux produced by the magnets.

FIG. 48 illustrates preferred relative movement of the container 1 and the magnet(s) for washing of nucleic acid bound magnetic particles.

DETAILED DESCRIPTION OF THE INVENTION

Figure 3A:
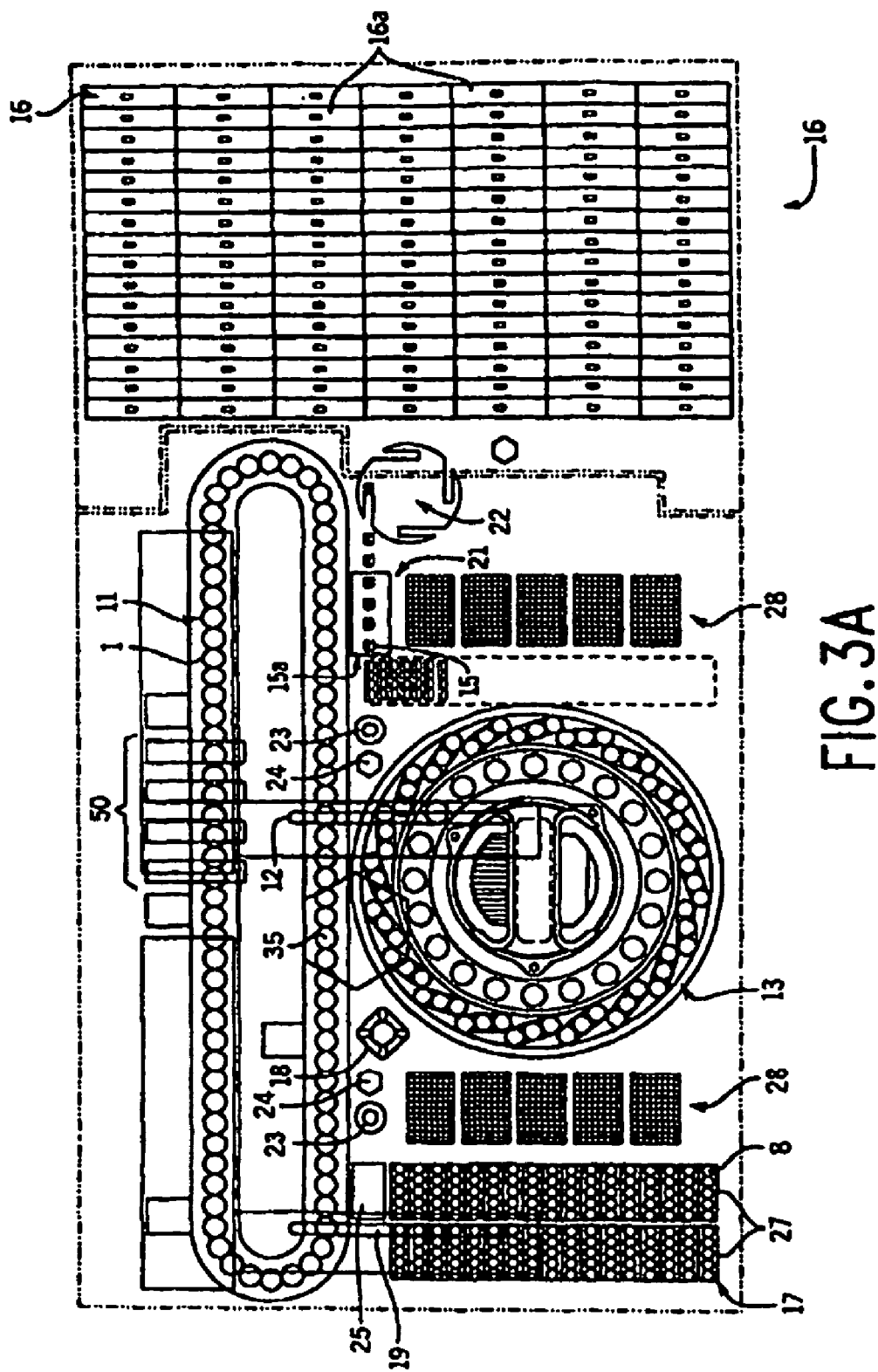
FIG. 3A is a generic top view of one embodiment of an apparatus with which the present invention may be used.

The embodiments described herein relate to methods and structures for determining an item of interest in a sample. The item of interest may be a specific region or regions of DNA or RNA, or may be fragments, complements, peptides, polypeptides, enzymes, prions, proteins, messenger RNA, transfer RNA, mitochondrial RNA or DNA, antibodies, antigens, allergens, parts of biological entities such as cells, virons or the like, surface proteins, functional equivalents of any of these, concentrations of any of these or any other desired element of the sample. In an exemplary embodiment, the item of interest may be selected from, but is not limited to specific DNA or RNA regions, antibodies, or antigens including but not limited to, CT, CT/GC, MT, HCV, HBV, HPV, HIV, CMV, HLA, HTLV, and other items related, but not limited to, infectious diseases, genetic markers, cancers, cardiovascular items, pharmacogenetic items, etc. In some embodiments, the item of interest may be selected from, but not limited to antibodies to HCV, antibodies to HIV 1/HIV 2, antibodies to hepatitis B core antigen (HBcAb), carcinoembryonic antigen (CEA), cancer antigen 19-9 (CA19-9), Hepatitis B Surface Antigen (HBsAg), antibodies to Hepatitis B Surface antigen (HBsAb), alpha-fetoprotein (AFP), Total prostate specific antigen (Total PSA), Free PSA, Thyroid stimulating Hormone (TSH), luteinizing hormone (LH), follicle stimulating hormone (FSH), beta human chorionic gonadotropin (B-hCG), Free Thyroxine (Free T4), Free triiodothyronine (Free T3), Total T4, Total T3, Progesterone, Testosterone, Estradiol, Prolactin, vitamin B12 (B12), Folate, Glycated Hemoglobin, and Ferritin. In essence, almost anything can be the item of interest.

The structures and methods described herein may be employed in a number of different configurations. For the sake of clarity of understanding, the structures and methods will be discussed with respect to their employment in a DNA/RNA sample preparation, amplification, and detection analyzer which performs approximately 100 or more determinations of items of interest in a sample in an hour or, if the sample preparation is divided, approximately 300 or more determinations of items of interest in a sample in an hour. Alternately, the same structure may be used as an immunoassay analyzer or as both an immunoassay analyzer and DNA/RNA analyzer. It is to be noted that the structures and methods can be used in other employments, such as in analyzers which perform 600, 400, 200, 50, etc. determinations in an hour.

A number of structures may be joined together or integrated to meet individual needs, such as modifying the number of tests performed in a given time period (throughput), tailoring the items of interest to be determined, etc. For example, a number X of structures which perform Y determinations in a given hour may be connected such that the connected structures perform XY determinations in an hour. If desired, the resources of the structures may be allocated in a manner substantially similar to that disclosed in U.S. Pat. No. 6,022,746. That application is assigned to the assignee of the present case and the disclosure thereof is incorporated herein in its entirety.

In other embodiments, one or more structures may be operatively connected with another analyzer, such as an immunoassay analyzer (e.g. disclosed in U.S. Pat. No. 5,795,784 referenced below), a blood analyzer (e.g. disclosed in U.S. Pat. No. 5,891,734 referenced below), and the like.

It is to be noted that all such structures may perform all similar determinations of items on interest in substantially the same way. For instance, all determination process steps for all similar items of interest may be performed within the same time frame, such as 36 seconds, irrespective of the number of determinations to be performed by the given structure. These structures may include common elements, such as reagents, disposable articles, other elements, such as fluids and the like, delivery technologies, determination step performance mechanisms, software, etc.

In other applications, the structure may be joined, e.g. with a conveyor system and the like, along with supporting hardware and software, such that the structure can be used with different structures or analyzers, such as clinical chemistry or hematology analyzers and the like, in the same setting. This conveyor system may move samples among the structures such that different determinations can be made with respect to one sample. Also, while operation of the structure is described herein with respect to only one structure, for the sake of clarity, it is to be remembered that multiple structures can operate in the same or in different fashion, either simultaneously or at different times. Furthermore, steps of one method of operation can be combined with steps of another method of operation to arrive at yet more methods of operation.

Any of the structures or methods described herein may be combined, in any suitable fashion, with other structures or methods or portions thereof, including those described in currently available literature, such as U.S. Pat. Nos. 5,856,194, and 6,413,780.

Construction of structures described herein is intended to analyze specimens for various items of interest in a cost-effective way. The structures allow a user to supply a sample to the structure, to have the structure process, e.g. incubate, prepare, lyse, elute, analyze, read, etc., the sample and to have the structure report a result of the process. Structure sub-components include apparatus and methods of mixing, aspiration and dispense of materials, such as samples and reagents, incubation, chemistry separation, and detection, just to name a few. In general terms, structure construction implementation for chemistry automation may be driven by many factors such as desired patient sample addition methods, reagent addition methods, throughput (number of determinations per given time period), contamination reduction methods, detection methods, degree of mixing, and incubation temperature and duration needs.

FIG. 1 discloses a structure 1a amenable to a relatively decreased throughput (such as about 1 determination per every 1.5 hours) environment. The structure 1a comprises a first container 1 removably placed in a base 2.

Figure 12A:
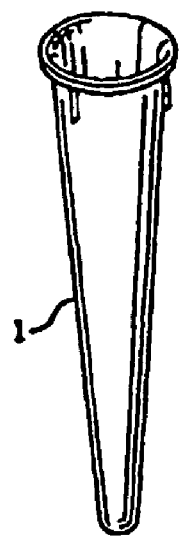
FIGS. 12A through 12R are perspective views of various alternative embodiments of the container shown in FIG. 1.
Figure 12B:
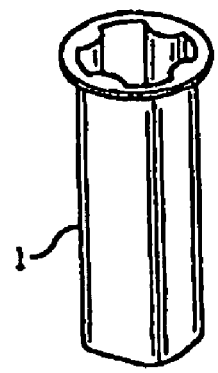
Figure 12C:
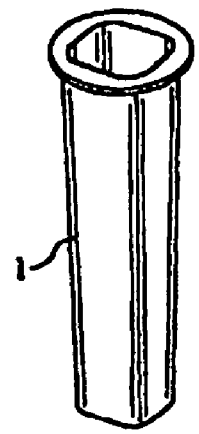
Figure 12D:
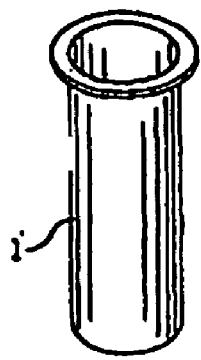
Figure 12E:
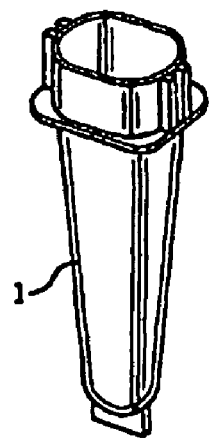
Figure 12F:
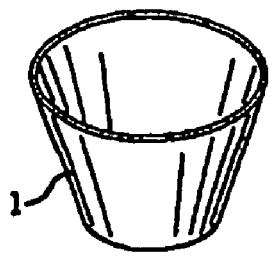
Figure 12G:
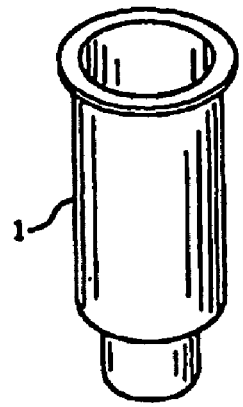
Figure 12H:
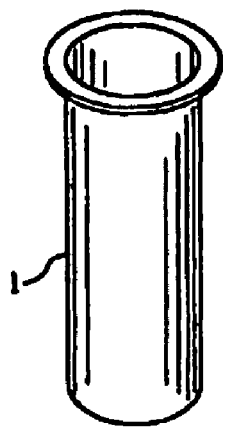
Figure 12I:
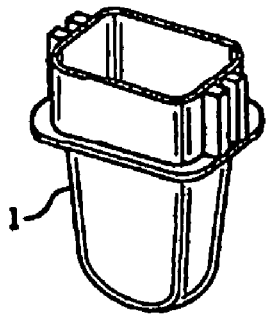
Figure 12J:
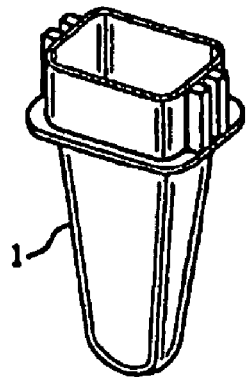
Figures 12K, 12L:
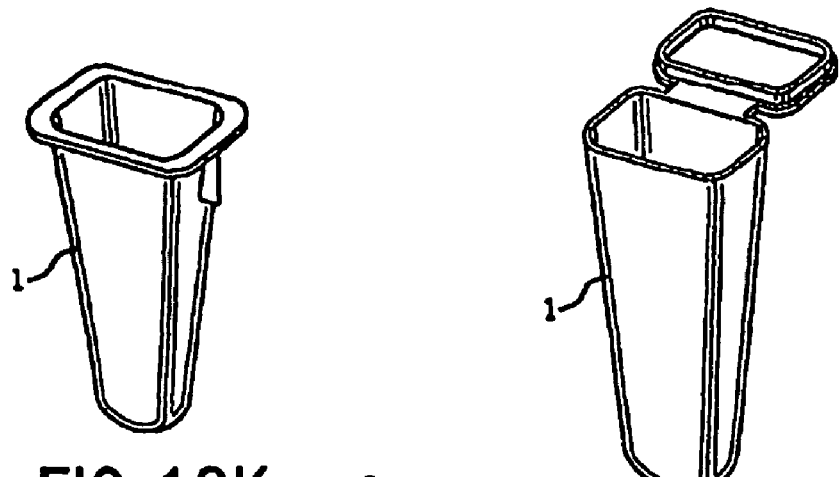
Figure 12M:
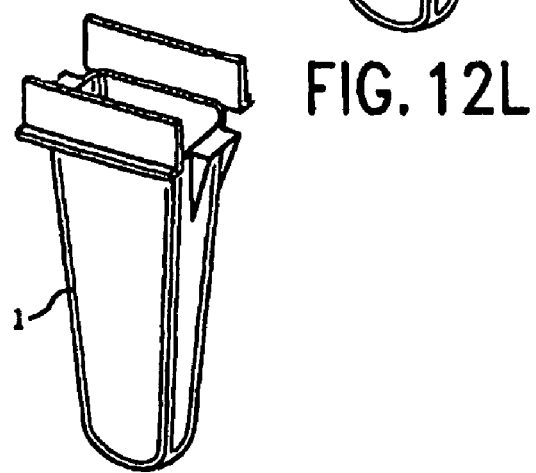
Figures 12N, 12O:
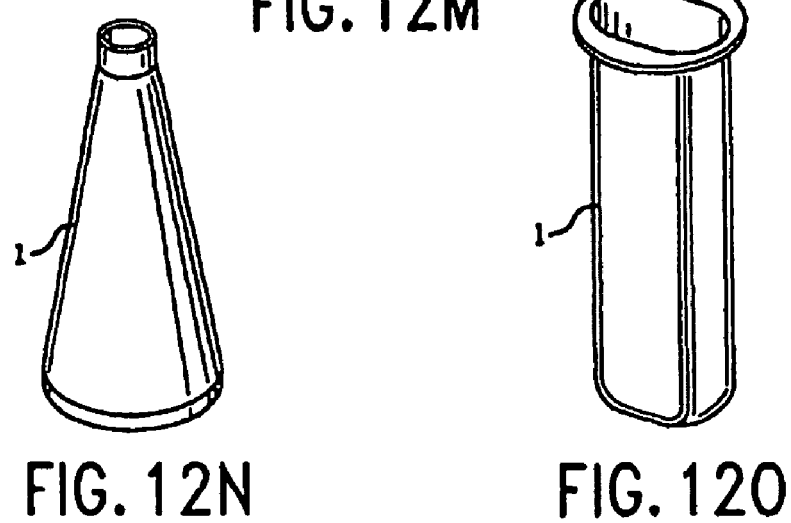
Figure 12P:
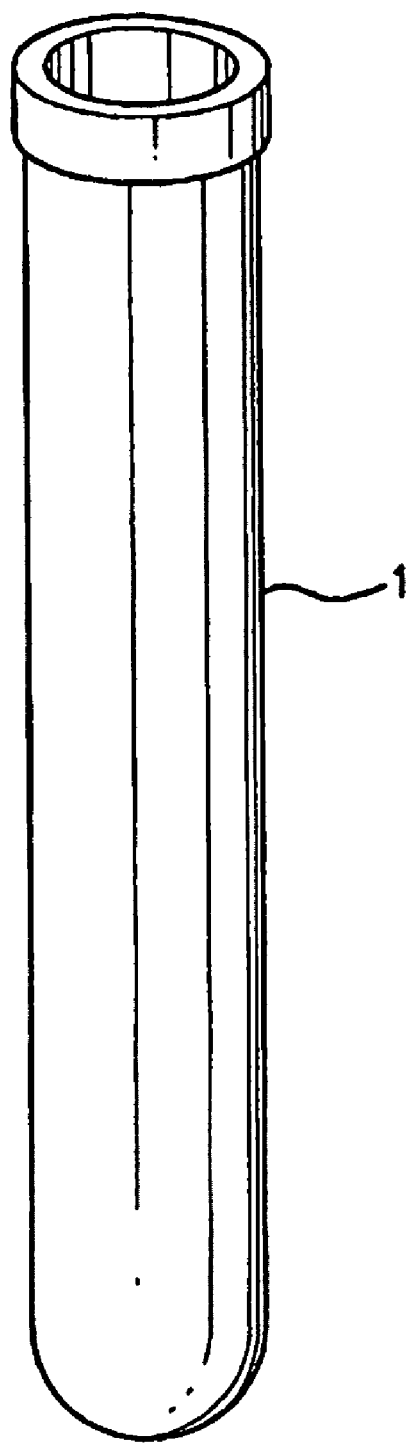
Figure 12Q:
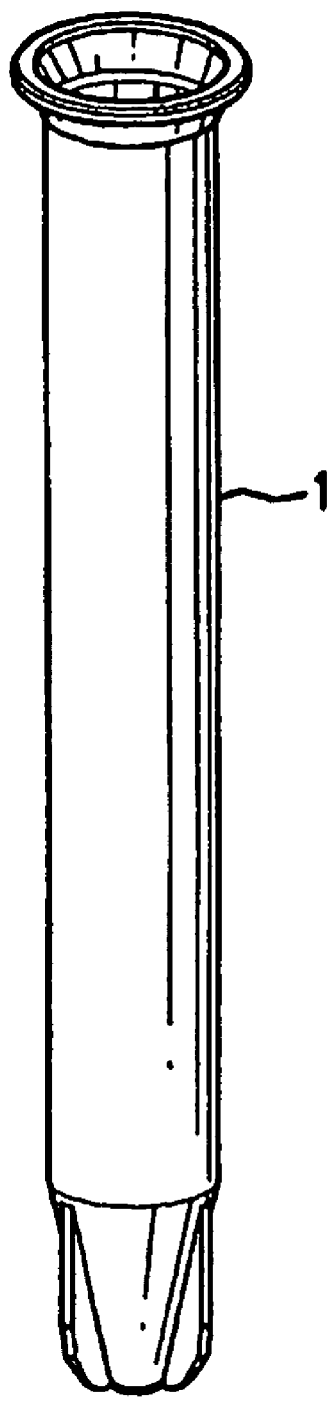

In the illustrated embodiment, the first container 1 is sized to contain a selected amount of fluid (e.g., about 7 mL of sample and reagent). However, it should be understood that various shapes and sizes of the container could be used with the present invention. FIGS. 12A through 12P show a variety of such alternative constructions of the first container 1??.

The base 2 may have any suitable construction for receiving the container including, for example, constructions similar to those of the process path disclosed in above-referenced U.S. Pat. No. 5,795,784 (in which case, the structures illustrated in FIGS. 1 and 2 can be disposed at appropriate locations along the process path). Of course, the base 2 may be modified to accommodate or complement various constructions of the first container 1.

The base 2 may be fabricated out of any suitable material, such as machined and coated aluminum and the like. In an exemplary embodiment, the base 2 is made with 6061-T6 aluminum with a MIL-A-63576 Type I finish. The first container 1 may also be fabricated out of any suitable material, including molding out of a polyethlyne (e.g., DOW 30460M HDPE or Chevron 9512) polypropylene (e.g., Montel PD701N or its replacements such as PD702), or polystyrene (e.g., Dow 666).

A probe 3 is preferably attached to a suitable drive which controls movement of the probe 3 in the desired directions (e.g., X, Y and/or Z axes). While any drive providing the desired movement would be suitable, suitable known drives includes a Tecan gantry (Tecan RSP model series, Tecan Switzerland) and an Abbott theta-Z robot (part number 78479, Abbott Laboratories, Abbott Park Ill.).

The probe 3 is fluidly connected at location 3a to suitable structures (not shown) which enable the probe 3 to perform aspiration and dispense functions. For example, these fluidic functions may be implemented with use of any pump (e.g., syringe, peristaltic, etc.) and valve technology suitable for the intended functions.

A retractable magnet 4 is suitably supported so that it can be moved with respect to the first container 1 and base 2 at selected times during performance of a given determination of an item of interest in a sample in the first container 1 as described hereafter. The movement of the magnet 4 can effect performance of a step in the determination process thereby allowing that step to be selectively automatically performed or avoided as desired. In one embodiment, the magnet 4 may be moved relatively proximate to the container 1 to attract magnetically responsive particles within the first container 1 to a side wall of first container 1 thereby separating those magnetically responsive particles, which may be bound with a desired item of interest in a patient sample, from the remaining patient sample or other contents of the first container 1.

Before, during or after such magnet 4 induced separation, the probe 3 may aspirate a portion of the first container 1 contents to a waste/wash reservoir 10. Subsequent dispense, separation, and aspiration steps may be employed to enhance the item of interest determination. During periods of the determination where magnetic separation is not desired (i.e., the magnetic separation step is avoided), the magnet 4 may be suitably moved away from the first container 1 to reduce the effects of the magnetic field of the magnet 4 on the first container 1 and its contents.

Alternatively, magnetically responsive particles to which no item of interest is attached may be attracted to the side wall of the first container 1 while the remaining contents (possibly containing an item of interest) of the first container 1 is removed from the first container 1, such as by the probe 3.

A thermal regulation device 7 may also be provided with the base 2 for providing heating and/or cooling, if such regulation is desired. The device 7 may be manually or automatically removably connected with the base 2, may be operated by an appropriate controller (such as a computer having memory running appropriate routines), and may utilize any suitable thermal transfer means, including conduction, convection, and/or radiation, etc. For example, thermally regulated (heated and/or chilled) air may be moved with respect to the first container 1 to thermally regulate the contents of the first container 1 in a desired manner.

At various times during performance of a given determination of an item of interest, a sample disposed in a sample or specimen container 8 (such as test tubes and the like) and reagent contained in a reagent container 9 may be added to first container 1, such as by use of the probe 3. If multiple samples and/or reagents are desired, an array, such as a conveyor, a carousel, other movable or stationary arrangement, possibly recirculating, or the like, of multiple containers 8 and/or 9 could be provided. The sample and reagent containers 8 and 9 may be fabricated out of any suitable material including, for example, a polymer like polystyrene (DOW 666), high-density polyethylene (DOW 30460M HDPE or Chevron 9512), and the like.

To increase preservation of the contents of either container 8 or 9, a cover 30 (see FIG. 5C), substantially similar to the cover disclosed in U.S. Pat. No. 5,795,784 referenced above, may be provided for either or both of the sample and reagent containers 8, 9. The cover 30 may be made from any suitable material, such as Lexington Medical 3481005 EPDM, Abbott EPDM (Ashland, Ohio) and the like. Suitable containers 8 and 9 and associated covers are shown in U.S. Pat. Nos. Des. 401,697, Des. 401,699, and Des. 397,938, referenced above. A method for fitting a container (such as container 8) to other containers or a carrier is described in commonly owned U.S. Pat. No. 5,915,583, and may be used within the scope of the present invention.

Once a sample and/or reagent are added to the first container 1, the probe 3 may be suitably washed to remove contaminants and thereby reduce the likelihood of the first container 1 being exposed to a contaminant thereafter. For example, the probe 3 may be moved to waste/wash reservoir 10 for a fluid rinse of the probe 3. The probe 3 may alternatively be modified to incorporate a disposable tip, such as the pipettor tip disclosed in U.S. Pat. No. 5,232,669, the entire disclosure of which is hereby incorporated by reference), with the disposable tip being ejected to waste from a fluidic/transport interface with the probe 3 after completion of its intended use. FIG. 5F illustrates another example of a disposable tip 28.

A suitable opening such as a bore 6 may be provided in the base 2 to accommodate a desired detector which may be advantageously used by the structure, such as a photomultiplier tube, a photodiode and the like. In the illustrated FIG. 1 embodiment, the bore 6 is located opposite the magnet 4 in a similar fashion to the like structures disclosed in U.S. Pat. No. 5,795,784. Thus, similar operations, such as detection of chemiluminescence or other signals generated by a label, such as a fluorophore and the like, are possible.

A suitable mixer 5, illustrated in FIG. 2, is also provided on the base 2. The mixer 5 is coupled to a suitable drive 5a that applies force to the mixer 5 which may, for example, induce an orbital motion on the first container 1 to cause the contents of the first container 1 to be mixed at desired times. Alternate constructions of suitable mixers are shown in FIG. 13 and in U.S. Pat. No. 5,795,784.

The base 2 is constructed to limit the freedom of movement of the first container 1 to allow the mixer 5 to accomplish the desired mixing. The base 2 may also include a lid (not shown) to assist in that regard.

If desired, the structure 1a shown in FIG. 1 may be modified to perform a larger number of determinations, such as about 100, in a given time period to provide a relatively increased throughput environment. When so modified, an array of structure 1a may be operatively connected together, with each effectively including one or more of the probe 3, magnet 4, mixer 5, bore 6 for a detector, and thermal regulation device 7, with such elements being individually provided for each of the connected structures 1a or appropriately shared between structures 1a. The probe 3, magnet 4, detector 6, heat/cooling elements 7, and/or mixer 5 may be selectively activated so that desired actions, such as sample and reagent aspirations and dispenses, are performed at desired times during the determination process, such a configuration being particularly well suited for selective automatic operation of those components to accomplish the desired steps. With such a configuration, a determination of an item of interest in a sample can be conducted over more than one position or with more than one structure 1a, thereby allowing at least two samples to be processed substantially simultaneously.

To streamline operative connection of multiple structures 1a, a transport system, such as a conveyor (bounded or endless), a carousel or the like, may be used to move a first container 1 from one structure 1a to another. The transport system may be substantially similar to the process path disclosed in the above-referenced U.S. Pat. No. 5,795,784. Depending on location of the structure(s) 1a, the transport system and/or the individual structures may be constructed to provide only the functions desired to be performed at a given time in a determination. For example, a relatively large number (e.g., 100) of structures 1a may be operatively connected together and only a subset (e.g., 5) of the structures 1a may include a mixer 5.

Figure 3B:
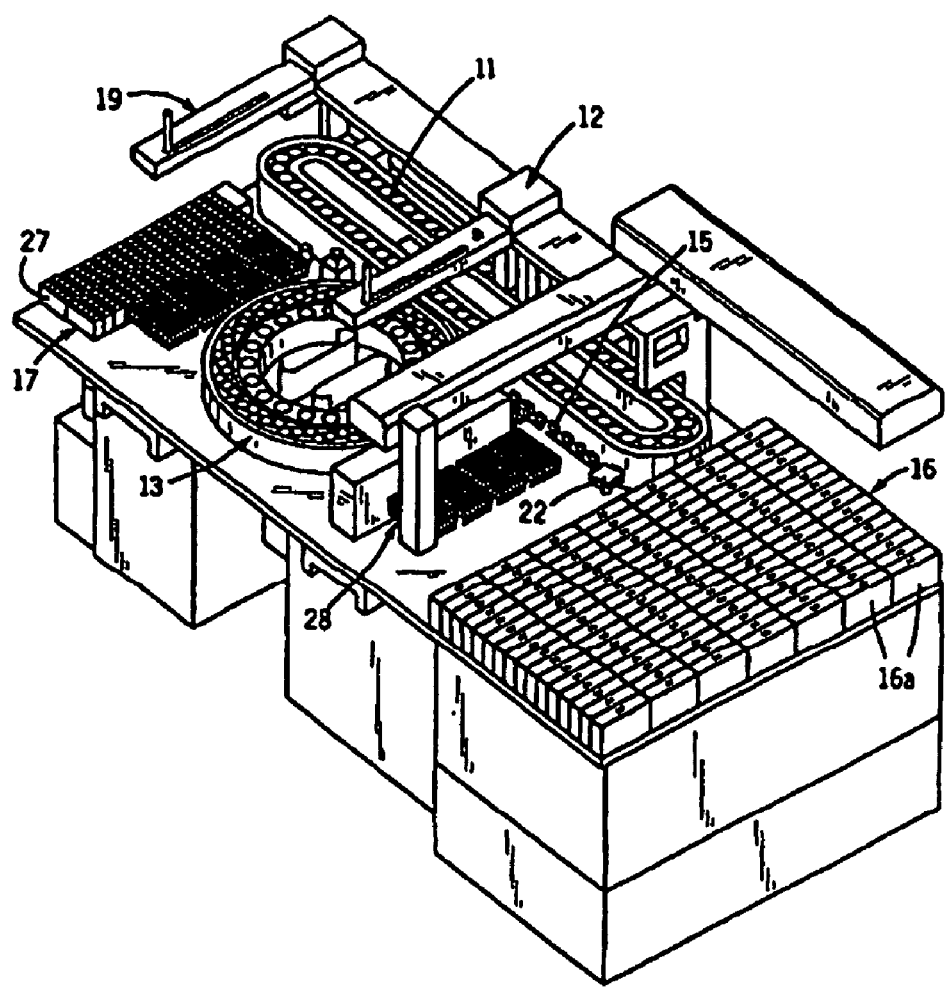
FIG. 3B is a perspective view of the apparatus shown in FIG. 3A.
Figure 9:
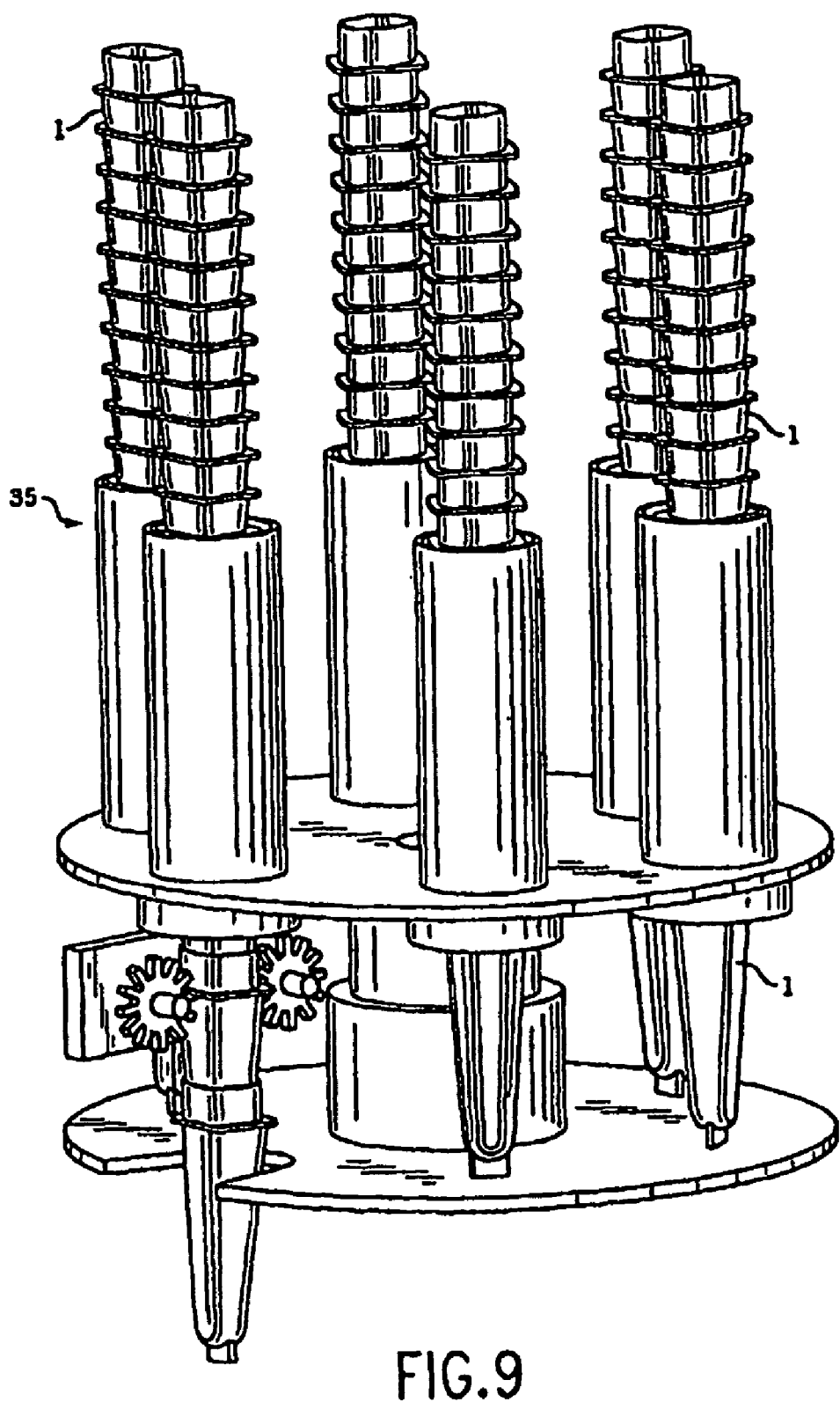
FIG. 9 is a perspective view of a container loader for use with the apparatus of FIGS. 3A and 3B.
Figure 18:
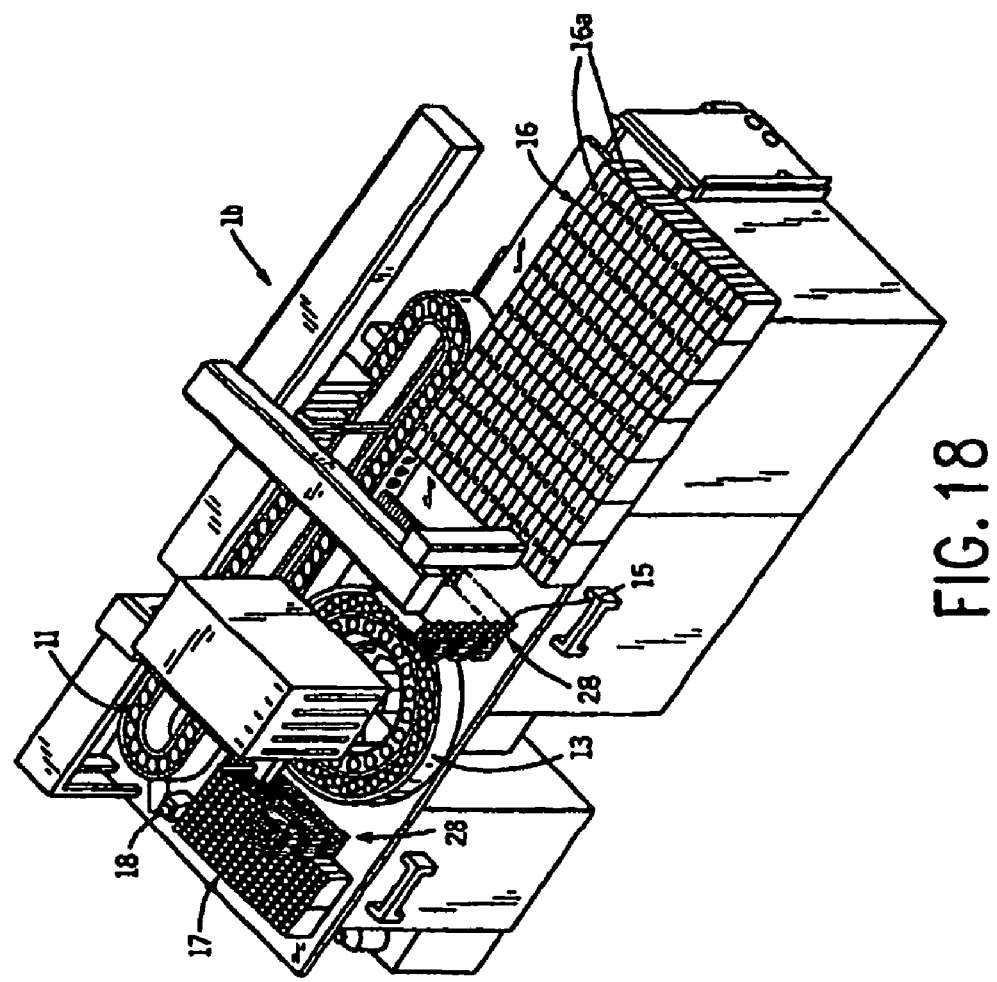
FIG. 18 is an isometric view of an alternative embodiment of an apparatus similar to the apparatus of FIGS. 3A and 3B.

FIGS. 3A, 3B and 18 show an apparatus 100 essentially including a plurality of structures 1a located substantially adjacent one another. In this embodiment, the first containers 1 are loaded substantially automatically onto a first process path 11 from a container loader and transport 35 illustrated in FIG. 9. Alternately, the first containers 1 may be loaded manually or automatically in a fashion described in U.S. Pat. No. 5,795,784. The containers 1 are moved, for example one position every selected time interval (such as every 36 seconds), through the first process path 11 to various locations along the first process path 11 where various operations (such as reagent addition, sample addition, incubation, mixing, washing and the like) are selectively automatically performed according to requirements of the intended format or protocol of the determination being performed. In an exemplary embodiment of the apparatus 100, the first container 1 is moved approximately 1.2 inches along the first process path 11 about every 36 seconds.

The first process path 11 includes at least one suitable temperature controller or heater to keep the first process path 11 at a desired temperature. The first process path 11 may be kept at one temperature or any desired number of temperatures, such as with multiple heaters. For example, in one embodiment, the heater may maintain the first process path 11 at about 37 degrees Celsius, whereas in another embodiment, one portion of the first process path 11 may be maintained at about 37 degrees Celsius while another portion of the first process path may be maintained at about 70 degrees Celsius.

Any suitable method may be used to heat the first process path 11 to at least one temperature while isolating the container 1 maintained at the least one temperature from other temperatures. Accordingly, as an example, the first process path 11 may be used to perform a first incubation, such as lysis for about 20 minutes at about 37 degrees Celsius, and a second incubation, such as elution for about 20 minutes at about 50 degrees Celsius, with a single first container 1. The container 1 being used for both lysis and elution on the first process path 11 may be thermally isolated from the second temperature while the container 1 is exposed to the first temperature, and vice versa.

As one example, the first process path 11 may be made of a suitable material, such as aluminum and the like, in which case if the first process path 11 is heated (e.g., conductively) to a first temperature or a second temperature at an appropriate time, a member may be introduced to thermally insulate portions of the first process path 11 exposed to the first temperature from portions of the first process path 11 exposed to the second temperature. This member may be an insulating material, a physical barrier or the like, and may be actively cooled or heated based on temperature conditions measured at the first process path 11 portions specific to the first temperature (e.g. 37 degrees Celsius) and specific to the second temperature (e.g. 50 degrees Celsius), thereby limiting exposure of the first container 1 to the first or second temperature, as appropriate.

In another embodiment, the first process path 11 may be maintained at a first temperature (e.g., 37 degrees Celsius). At a portion of the first process path 11, where it is desired to maintain a second temperature (e.g., 50 degrees Celsius), at least one other thermal energy source, such as an IR source and the like, may be thermally coupled with the first process path 11 to provide a desired amount of heat to the relevant portions of the first process path 11 at times required. Contents present in container 1 may experience a thermal rise to the second temperature during exposure to that additional thermal source (e.g., the IR source) followed by a thermal degradation to the first temperature as the container 1 is removed from exposure to the additional thermal source.

Figure 10:
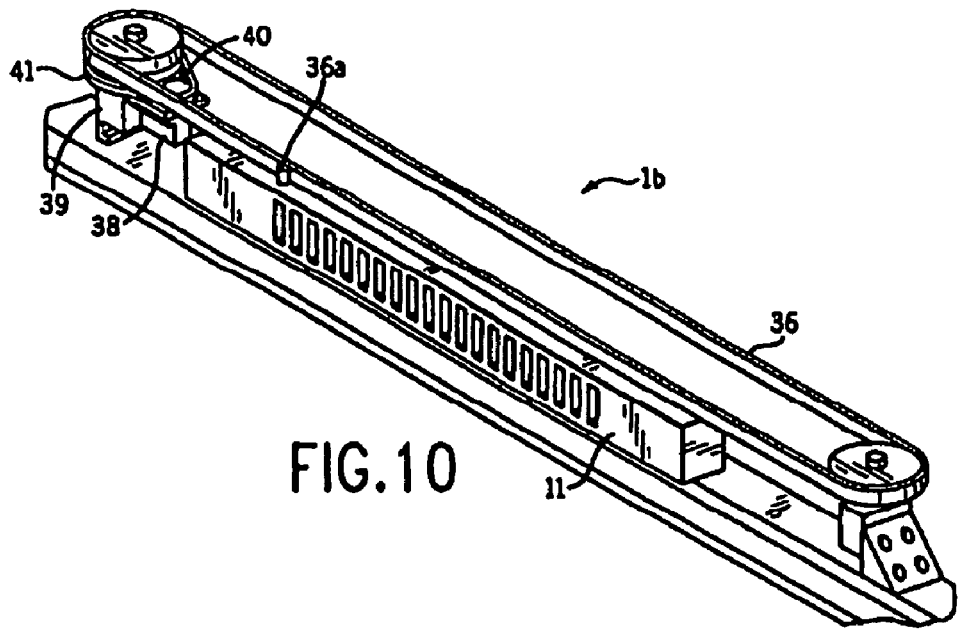
FIG. 10 is a perspective view of a container transporter for use with the apparatus shown in FIGS. 3A and 3B.
Figure 11:
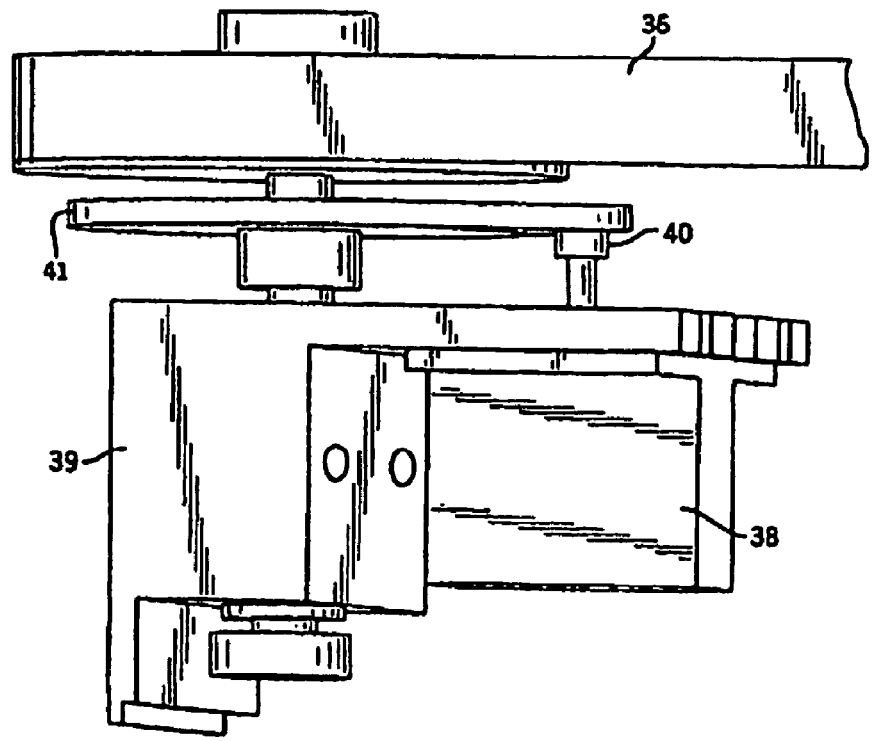
FIG. 11 is a magnified view of a portion of FIG. 10.

FIGS. 10 and 11 illustrate a container transport which may be used at the first process path 11 of the apparatus 100 illustrated in FIGS. 3A, 3B, and 11. With this structure, once a first container 1 is placed on the first process path 11, a belt 36 moves the first container 1 via engagement with pin 36a on the belt 36. The drive 38 is suitably supported on the apparatus 100 by a mount 39, and drivably engages the belt 36 via drive gear 40 and driven gear 41.

Returning to FIGS. 3A and 3B, samples disposed in sample containers 8 are suitably loaded in container carriers 27 (e.g., trays) which are loaded onto input queue 17 on the deck of the apparatus 100. It should be understood that the various process steps may, within the broad scope of various aspects of the invention disclosed herein, be done manually and/or automatically, whether described as being done in one manner or another herein.

Figure 6:
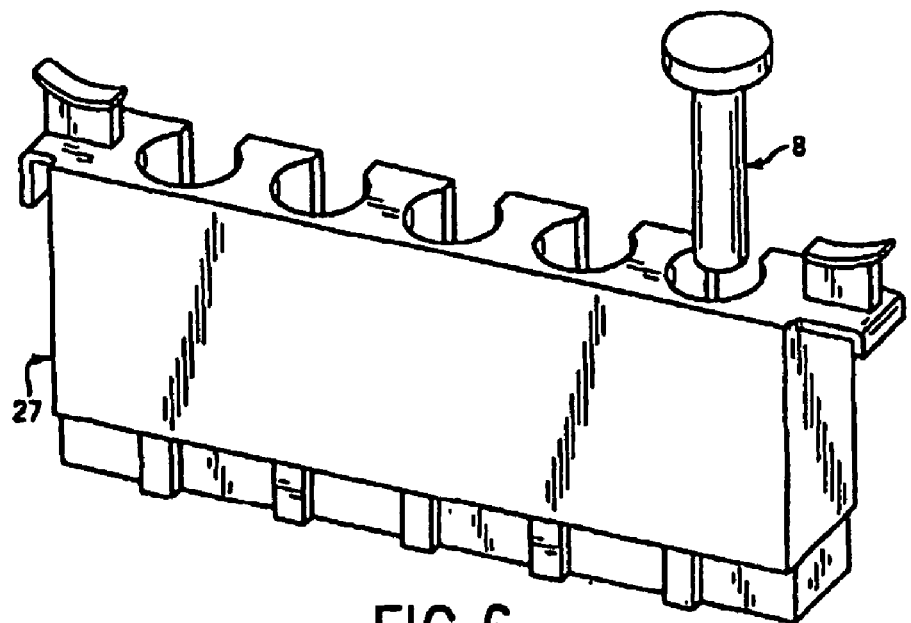
FIG. 6 is a perspective view of a container and a carrier for use with the apparatus of FIGS. 3A and 3B.

Examples of a sample container 8 and an associated container carrier 27 are shown in FIG. 6. The container 8 and the container carrier 27 may be substantially similar to the container disclosed in above-referenced U.S. Pat. No. 5,915,583 and Des. 401,697, though those with an understanding of the art will recognize that a wide variety of configurations would be suitable within the scope of the present invention.

Figure 4:
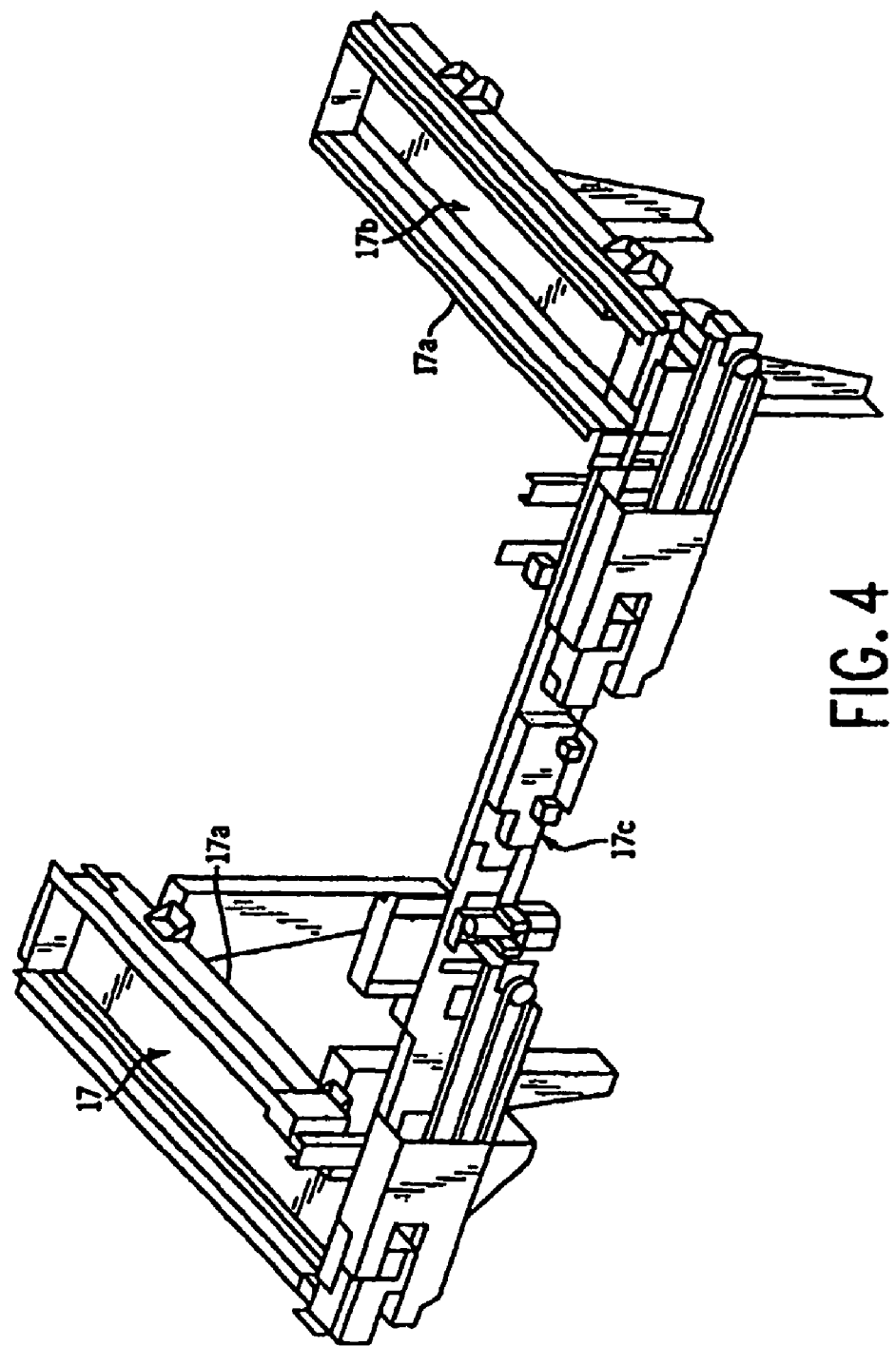
FIG. 4 is a perspective view of a sample queue for use with the apparatus of FIGS. 3A and 3B.

Input queue 17 may be any suitable configuration for holding a desired number of sample containers 8, including configurations such as those currently available from Abbott Laboratories (e.g., Abbott FPC Flexible Pipetting Center), or the structures described in U.S. Pat. No. 5,795,784. One such suitable configuration of an input queue 17 is shown in FIG. 4 and comprises a conveyor system like that disclosed in U.S. Pat. No. 5,795,784. The embodiment illustrated in FIG. 4 is constructed such that a structure, such as the apparatus 100 of FIGS. 3A and 3B, may be disposed in space 17a so that the input queue 17 and the apparatus 100 can cooperate. In this embodiment, sample input and output queues 17 and 17b, respectively, may be disposed adjacent to each other, offset by a local queue 17c.

A bar code reader 25 may be located adjacent the first process path 11 whereby that the bar code reader 25 can read a code associated with the container 8 and/or the container carrier 27. The bar code reader 25 may be used to identify a given sample located on the input queue 17 at a position accessible by a pipettor 19.

When the bar code reader 25 identifies a sample, pipettor 19 may suitably transfer that sample from the sample container 8 on the input queue 17 to a first container 1 located on the first process path 11. Other items, such as reagents and the like, may be added to one (or more, where multiple samples are being worked with) first containers 1 by pipettor 19 and pipettor 12 in accordance with a given determination format. Reagents may be stored in a suitable reagent handler 13, such as the reagent carousel disclosed in U.S. Pat. No. 5,795,784. In an exemplary embodiment, pipettors 19 and 12 may add reagents to one or more first containers 1 at times specified in the "1 Tube DNA/RNA 20-20 Min Sample Prep Protocol, 1 Tube 1.5 hr PCR End Point Protocol" specified below.

In addition to pipettor 19 and 12, dispense nozzles (not shown for clarity) fluidly connected with appropriate pumping mechanisms may be used to add reagents from bottles 29, 31, and 32 (see FIGS. 5A, 5B, 5E and 19) to a first container 1. In one embodiment, one container (e.g., container 31) may contain solid phase microparticles, which are preferably magnetically responsive, and which may require an agitator to homogenize the container 31 contents (i.e., resuspend the particles in a fluid medium). The agitator may be incorporated into a microparticle reagent handler 18 shown in FIGS. 3A and 3B, and may homogenize by suitable action (e.g., mixing fins, complementary container fins and/or fin motion, among other methods). Resuspension of the particles within container 31 may, for example, be achieved with a stir bar and associated apparatus such as is commonly understood in the field.

Some or all containers described herein may be placed on the apparatus 100 shown in FIGS. 3A and 3B. The contents of the containers may be preserved with use of reagent seal 30 (shown in FIG. 5C) and/or with use of refrigeration. To provide additional flexibility in dispensing reagents, reagent dispense nozzles operatively associated with the first process path 11 may be integrated with transport mechanisms to allow reagents to be dispensed at any desired position on the first process path 11.

Sometimes, it may be desirable to mix or to agitate the contents of a first container 1. Mixing of contents of a first container 1 along the first process path 11 may be selectively automatically performed at a selected time by a suitable mixer 5, an example of which is shown in FIG. 13. In this embodiment, a first container 1 is operatively engaged via a bracket 44 which is, in turn, operatively coupled to a gear train 43 configured to induce motion (e.g., orbital, circular or other) to the bracket 44 and engaged first container 1 when driven by drive 42. Such mixing can be accomplished at any suitable, desired time depending on the requirements of the process being accomplished, such as the times specified in the "1 Tube DNA/RNA 20-20 Min Sample Prep Protocol, 1 Tube 1.5 hr PCR End Point Protocol" specified below.

Figure 7:
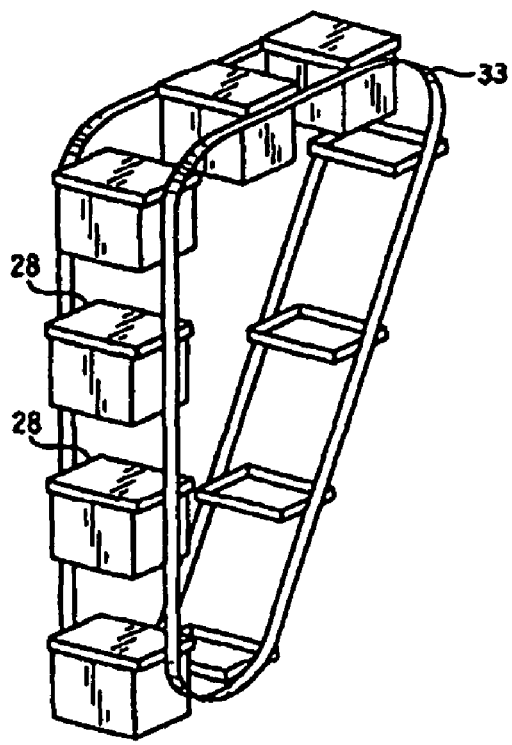
FIG. 7 is a perspective view of a pipette tip loader for use with the apparatus shown in FIGS. 3A and 3B.
Figure 8:
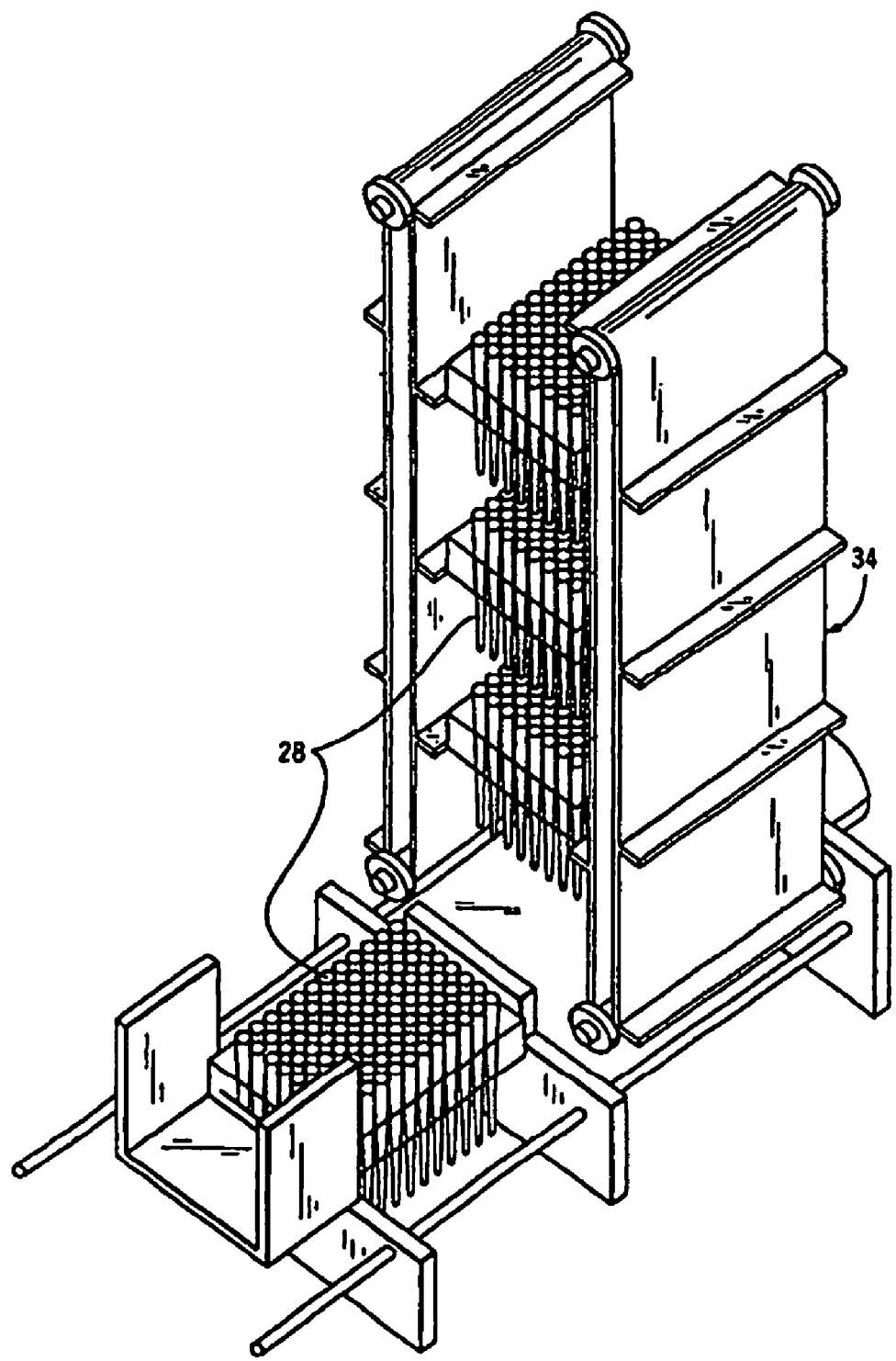
FIG. 8 is a perspective view of another embodiment of a pipette tip loader for use with the apparatus shown in FIGS. 3A and 3B.

In an embodiment where pipettors 19 and 12 are configured for use with disposable pipettor tips 28 (see FIGS. 5F and 19), transport and loading of a tip 28 or a group of tips 28 may be accomplished with suitable loader and transport mechanism 33. One such mechanism 33 is shown in FIG. 7, and another loader and transport mechanism 34 is shown in FIG. 8.

After engagement of a tip 28 by either pipettor 19 or 12, liquid level sensing (executed by any suitable method, many of which are well known in the art), aspiration from the selected container(s), and dispense to a first container 1 occurs. Pipettor 12 or 19 may include an apparatus which can detect a liquid level and/or temperature, which apparatus may include, but is not limited to, photo optics, capacitive members, IR, sonar, or other wave form generators. After dispense, tip 28 is washed with liquid at wash station 23, thereby reducing exposure to a contaminant. Subsequent additions to a first container 1 may occur in similar fashion, as desired. After all desired additions to first container 1 have been completed, first container 1 contents may be is aspirated or otherwise removed from first container 1 and dispensed or transferred to desired locations where other functions, such as genetic sequencing, a pharmacogenetic test and the like, can be performed. Then, the tip 28 may be removed from pipettor 12 or 19 and disposed to tip waste 24, thereby reducing exposure to a contaminant. Using a single tip 28 for multiple reagent and singular sample or prepared sample manipulations can reduce solid waste and can provide reduced cost while maintaining desired levels of contamination reduction. Similar steps may be performed with the pipettors 12 or 19 even if they do not include a tip 28.

Figure 14:
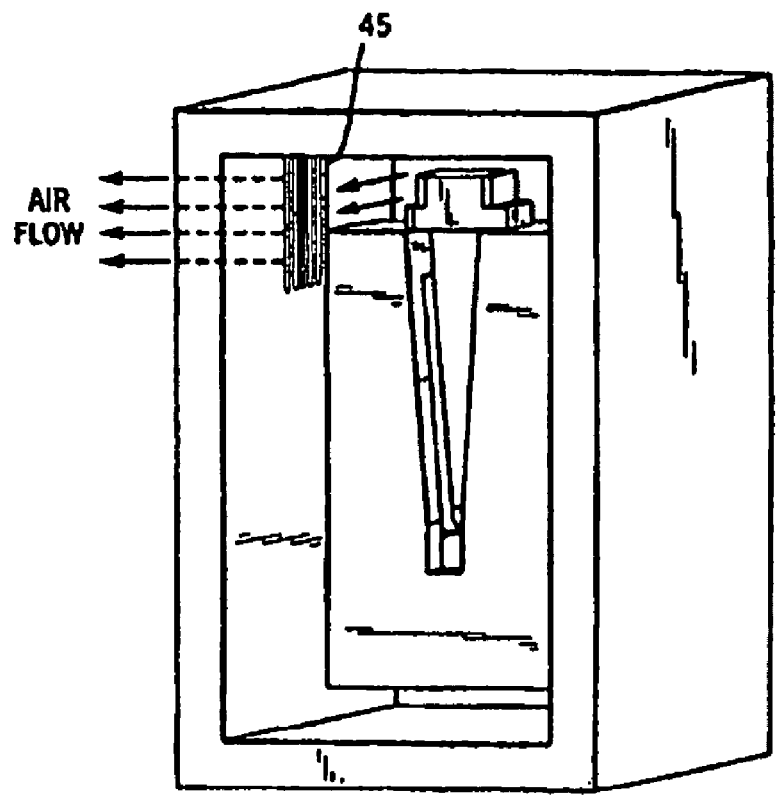
FIG. 14 shows a port provided in operative relationship with the process path of FIGS. 3A and 3B.

Mixing with mixer 5 or other motions imparted to a first container 1 may induce unintended distribution (e.g., aerosoling) of fluids contained in the first container 1. FIG. 14 shows a port 45 integrated into first process path 11 at appropriate locations. The port 45 may be fluidly connected with a fluid pressure source (e.g., a negative fluid pressure source such as a vacuum) that draws air flow above the first container 1 away from adjacent first containers 1 on the first process path 11 to a more desirable location. In this manner, undesirable airborne contaminants may be routed to controlled locations.

Washing of microparticles used in some methods performed by the structure 1a and apparatus 100, viz. immunodiagnostic and/or PCR sample preparation methods, may utilize removal, evacuation or pipetting of unbound or bound microparticles from the first container 1 and/or other constituents of the contents of the first container 1, such as if some of the first container 1 contents were attracted to and held by magnet 4.

Figure 16:
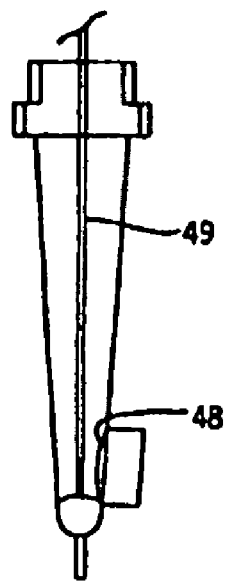
FIG. 16 illustrates one operation of the pipettor of FIG. 15.

To perform this washing, at least one wash zone 50 (see FIG. 3A) may be located at an appropriate position along first process path 11. The wash zone 50 may include a probe 49 (shown in FIG. 16) constructed to automatically evacuate or pipette the contents (e.g., unbound or bound microparticles) from first container 1. More than one probe 49 (e.g., four) may comprise a single wash zone 50. Suitable exemplary washing steps (e.g., magnetic separation, aspiration, dispense) are further described in U.S. Pat. No. 5,795,784.

Where contamination is a concern, such as with DNA/RNA determinations, the probe 49 may be formed with an outer tube 46 and inner tube 47 (see FIG. 15). The outer tube 46 may be held substantially concentrically with respect to the inner tube 47 via a support member 46a. In some embodiments, the member 46a may function as a fluid conveying conduit. In one embodiment, the outer tube 46 is fluidly connected to a wash fluid source and the inner tube 47 is fluidly connected to a vacuum source routed to waste. The wash fluid may be used for many purposes, such as to chemically wash unbound particles from particles bound to an item of interest held in first container 1, and also to remove undesirable items (i.e., contamination) from the inner tube 47 after the inner tube 47 comes into contact with fluid (e.g., fluid in the first container 1) during evacuation.

To improve methods of attracting microparticles to walls of a first container 1, the microparticles within the first container 1 may be exposed to a magnet station comprising two magnets disposed adjacent to the first container 1 along opposite sides of the first container 1.

Figure 17:
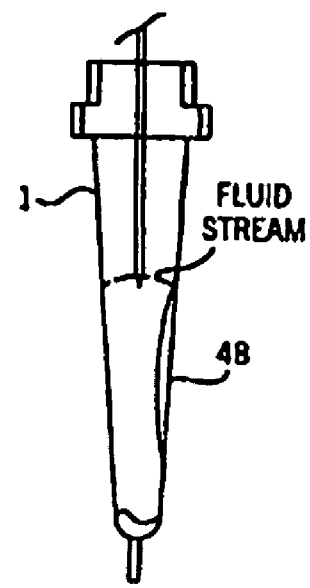
FIG. 17 illustrates another operation of the pipettor of FIG. 15.

Microparticles attracted to side wall(s) of the first container 1 can be resuspended at any time (e.g., during washing) via a suitable device, such as the mixer 5 shown in FIG. 13. Alternately, a probe 3 or 49 may be used to effect fluid and/or solid resuspension within the first container 1 by appropriate movement of fluid within the first container 1. In such an embodiment, fluid (e.g., wash solution) may be dispensed from a probe 3 or 49 such that a single or plurality of fluid streams is directed at a position within the first container 1, such as a vertical wall thereof, where relevant fluid and/or solid material to be resuspended is expected to reside. In this manner, the material to be resuspended in the first container 1 may be dispersed within the first container 1 as shown in FIG. 17.

After processing of first container 1 contents is complete according to the selected format or protocol, the first container 1 contents is moved from first container 1 and placed into second container 15 shown in FIG. 3. Material additions (e.g., reagents) to second container 15 occur via pipettor 12. The second container 15 is then sealed with sealer 21.

Where relatively quick heating and cooling rates of the second container 15 are desired, the second container 15 may be constructed to sustain relatively quick thermal energy transfer rates by using a relatively large heated surface to second container 15 contents volume ratio and/or a relatively thin wall(s) of the second container 15.

To facilitate transfer of the contents of the first container 1 to the second container 15 in an automated fashion, the second container 15 may be constructed with a first chamber and a second chamber with a first chamber opening being relatively larger than a second chamber opening. The pipettor 12 can enter and fill the first chamber with first container contents and other reagents, with the first chamber opening then sealed with sealer 21. The relatively smaller second chamber opening may restrict the contents of the first chamber from moving to the second chamber. Alternatively, the first chamber opening may be sealed by a sealer 21 to a first level (called a "soft-seal") prior to transfer of the container to a spinner 22. In this case, after removal of the second container 15 from spinner 22, the first chamber opening may be sealed by the sealer 21 to a second level different than the first level.

The second container 15 is transported to a spinner device 22 which moves the second container 15 so that the contents of the first chamber are displaced to the second chamber by centrifugal force. After the contents of the first chamber have moved to the second chamber, the second container 15 is removed from the spinner device 22 to a heat transfer device for further processing. Alternately, filling of second container 15 to its second chamber can be achieved by force induced by pressure from fluidics coupled to a pipettor 12, or a pipettor 12 can enter the second chamber of the second container 15 and thereby fill the second chamber.

Although capillary tubes or tubes having capillary-like construction are amenable to desirable heat transfer rates, filling such tubes typically involves force or centrifugation to move liquid into the tube. In another embodiment illustrated in FIGS. 27A through 27F, the second container 15 may comprise assembly 15c which accepts contents through an opening 57 which is relatively larger than a capillary tube to allow for automated pipetting of contents into the second container 15 without any secondary operations, such as centrifugation. Prior to further DNA amplification, seal 15b may engage the second container 15 to provide contamination reduction and evaporation control. An outer wall 58 of seal 15b is relatively smaller than an inner wall 59 of the second container 15 such that, when engaged with the second container 15, the contents in the second container 15 can displace around the outer wall 58. This displacement of contents increases heat transfer to liquid area ratio, thereby providing for relatively rapid heat transfer. In some embodiments, outer wall 58 may include fins (not shown) which engage the inner wall 59 of the second container 15 to position the seal 15b substantially concentrically with respect to the second container 15, thereby providing for substantially uniform displacement of contents around the outer wall 58 of the seal 15b and for substantially uniform heat transfer to the contents.

Figure 27A:
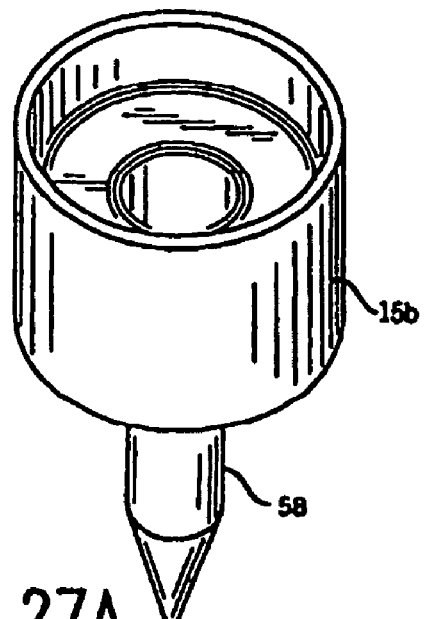
FIGS. 27A through 27F are perspective views of a container and seal for use with the apparatus of FIGS. 3A and 3B.
Figure 27B:
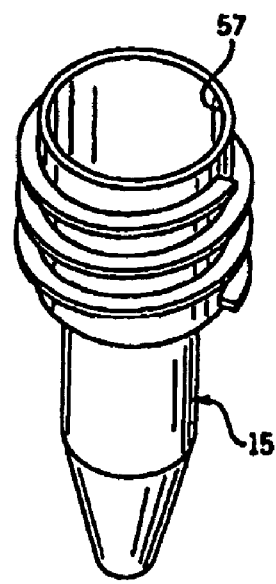
Figure 27C:
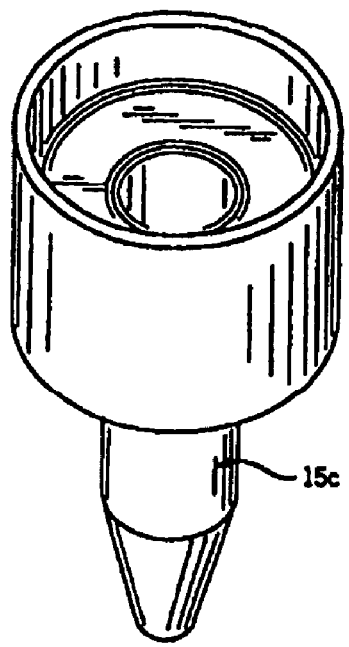
Figure 27D:
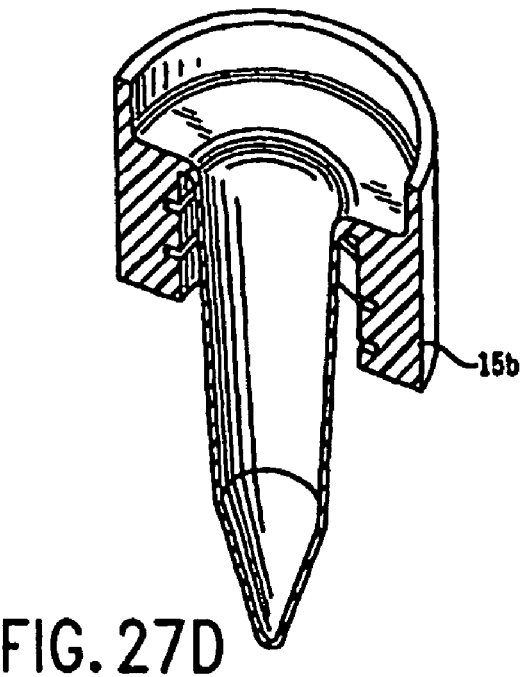
Figure 27E:
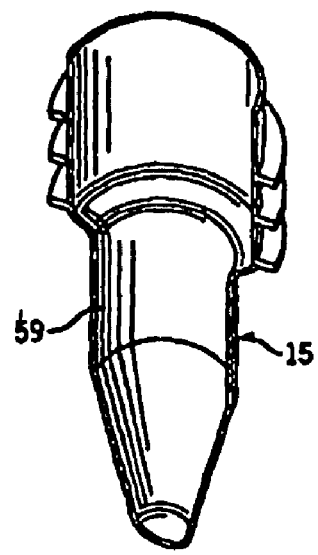
Figure 27F:
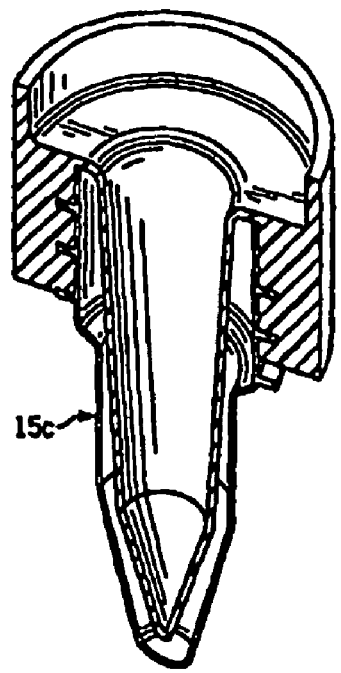

The second container 15 and seal 15b are matable to form the assembly 15c shown particularly in FIGS. 27C and 27F. This assembly 15c can be transferred to a second process path or thermal cycling/detection module 16 for further processing.

In one embodiment, the steps of transporting a second container 15 to the spinner device 22 occur after the pipettor 12 adds up to three reagents and sample to the second container 15. A robot then moves the second container 15 to a second process path or heat transfer/detection apparatus 16. The apparatus 16 may bring the second container 15 to a temperature the same as or different from a temperature(s) to which the first process path brings the first container 1.

FIGS. 3A and 3B illustrate one construction of the heat transfer/detection apparatus 16 comprising one hundred and twelve (112) heat transfer/detection modules 16a such that throughput of samples prepared on the first process path 11 is compatible with PCR processing times of approximately one hour to yield a structure throughput of approximately 100 tests per hour. The heat transfer/detection apparatus 16 can be used for isothermal reactions, thermal cycling, integrated heat transfer and detection, among other processes. In some embodiments, heat transfer functions and the detection functions can be performed by separate structures (e.g., the apparatus 16 can comprise a hat transfer structure and a detection structure, which may be located adjacently, separately or in any appropriate fashion). After detection in the apparatus 16, the second container 15 is automatically removed and discarded to waste by the robot or transferred to another detector for further determinations.

In the embodiment shown in FIGS. 3A and 3B, isolated sample preparation can be performed on the first process path 11 and amplification and detection can be performed on the adjacent apparatus 16, with these two processes being substantially separated such that contamination concerns specific to DNA/RNA chemistries may be reduced.

The first process path 11 for automated preparation of a sample may be operatively connected to the apparatus 16 for amplification and detection by further apparatus such as the robot.

The second process path 16 may also be a continuation of the first process path 11, thereby forming a single process path. In such embodiments, any of the containers described herein may be used along the entire process path, thereby eliminating the need to transfer from a first container 1 to a second container 15. In other words, a sample can be transferred from the sample container 8 to a single process container that is used to perform all the steps described herein.

There are a number of other possible modifications to the structure 1a and apparatus 100 which could be used within the scope of the broad invention described herein. In one modification, the first process path 11 in FIGS. 3A and 3B can include a process step performance lane where a process step is selectively automatically performed, and a process step avoidance lane where the process step is selectively automatically avoided (e.g., located to avoid a wash zone 50). The first container 1 containing the reaction mixture may be selectively automatically positioned in a selected one of the process step performance lane or the process step avoidance lane based on selected format or protocol similar to the manner described in U.S. Pat. No. 5,795,784.

In other modifications, the second container 15 may be a capillary tube, a tube possessing capillary tube characteristics, a reaction vessel described in U.S. Pat. No. Des. 401,700, a reaction tube (such as that supplied by Cepheid of Sunnyvale, Calif.), a tube similar to the first container 1, and the like. Also, heat transfer/detection apparatus 16 may utilize Peltier, microwave, resistive, forced air and/or liquid heating/cooling technologies. Accordingly, the modules 16a may also utilize Peltier, IR, microwave, resistive, forced air and/or liquid heating/cooling technologies, such as the thermal cycler and/or detector components of the Smart Cycler™ system supplied by Cepheid (Sunnyvale, Calif.), the Tetrad™ or PTC-100™ systems supplied by MJ Research, INC (Waltham, Mass.), the Sprint™ system supplied by Hybaid (Franklin, Mass.), the Multigene™ system supplied by Labnet International (Woodbridge, N.J.), the RoboCyler™ 40 or 96 systems supplied by Stratagene USA (La Jolla, Calif.), the 480, 9600, or 9700 systems supplied by Perkin-Elmer (Foster City, Calif.), all of which are suitable.

Still further modifications of the structure 1a and apparatus 100 are possible. The following examples of such modifications utilize common reference characters for similar structures.

Figure 20:
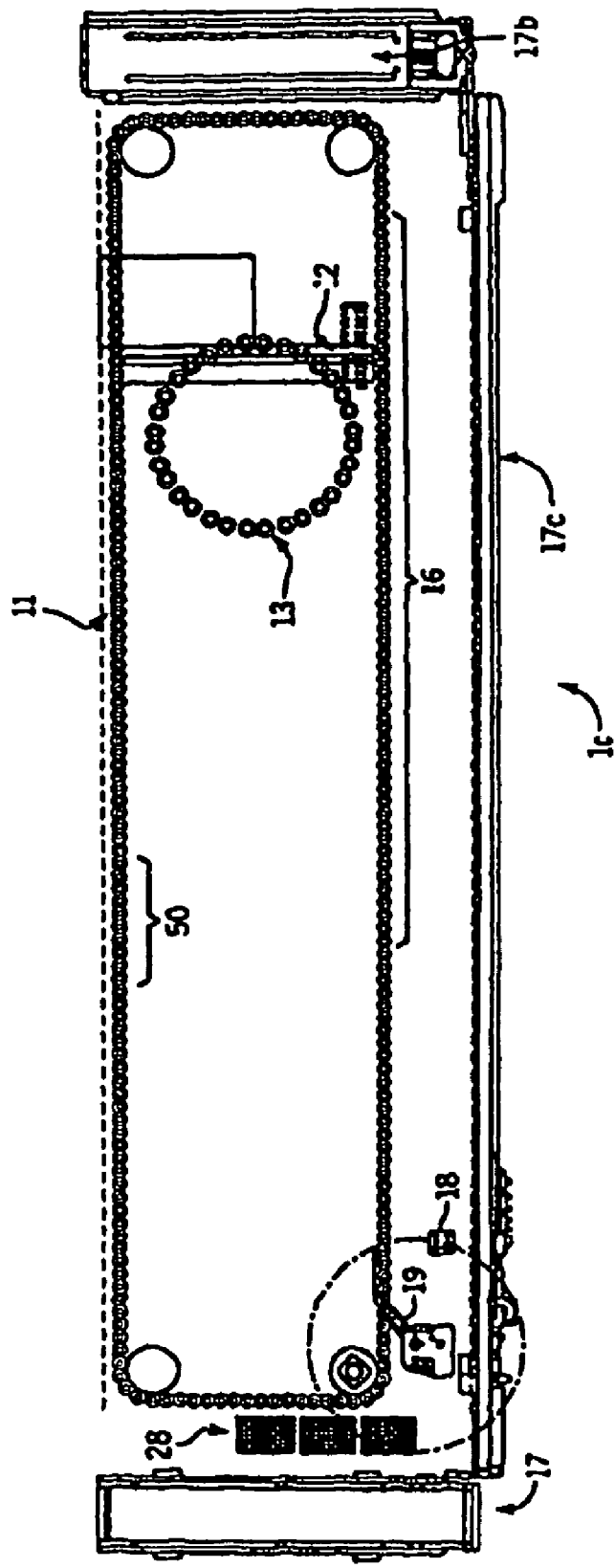
FIG. 20 is a top view of another apparatus substantially similar to the apparatus of FIGS. 3A and 3B.

In another apparatus 110 shown in FIG. 20, heat transfer/detection apparatus 16 can be integrated into first process path 11 as shown in FIG. 20. Here, the first container 1 remains on the first process path 11 while passing through thermal zones amenable to the desired format.

Figure 21:
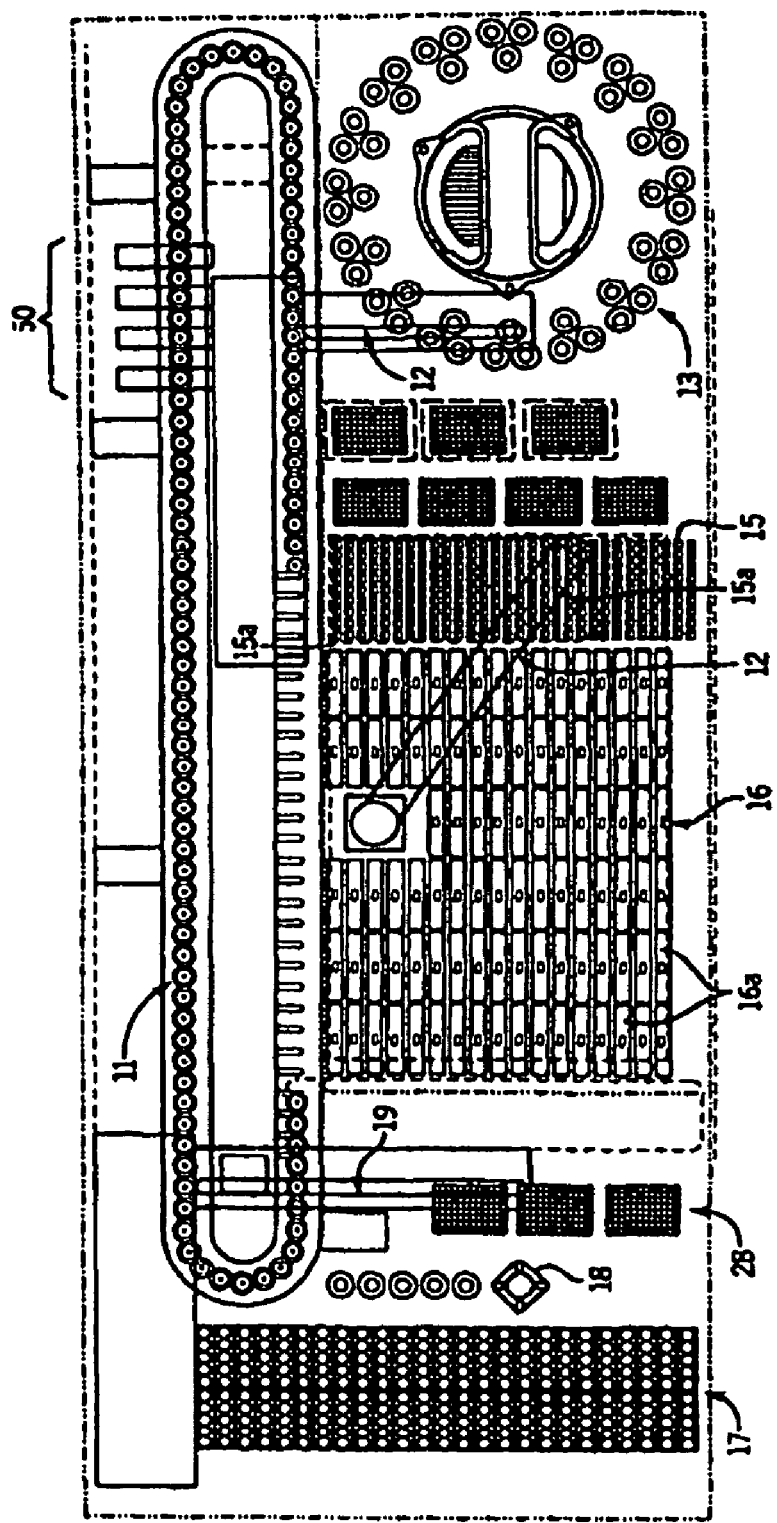
FIG. 21 is a top view of an additional apparatus substantially similar to the apparatus of FIG. 20.

In another apparatus 120 shown in FIG. 21, the first container 1 is transferred to the second container 15 and, subsequently, the second container 15 passes through thermal zones amenable to desired format. Thus, a portion of a thermal reaction can be implemented in the processing line 15a for the second container 15 prior to transfer of the second container 15 to the heat transfer/detection apparatus 16.

Figure 22:
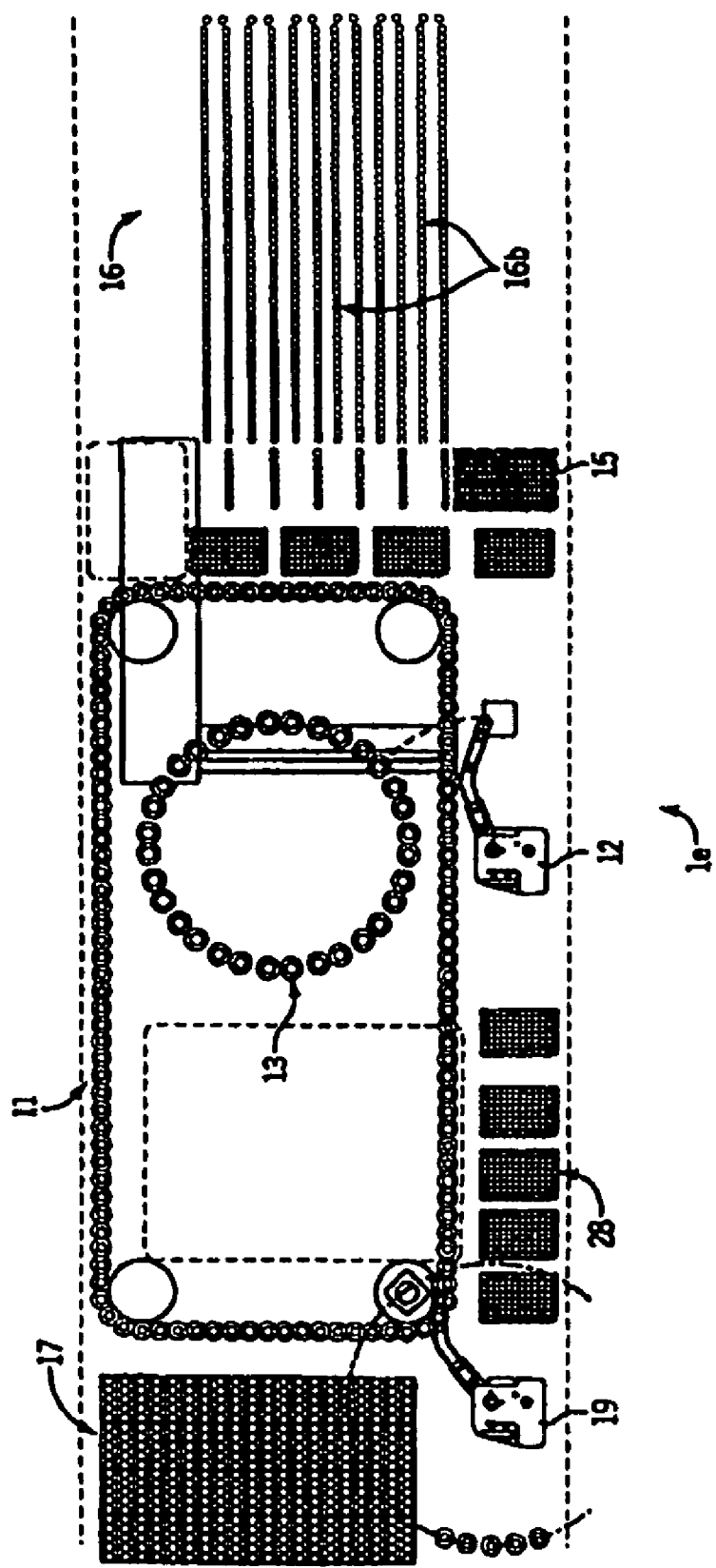
FIG. 22 is a top view of a further apparatus substantially similar to the apparatus of FIG. 21.

In still another apparatus 130 illustrated in FIG. 22, the second process path or heat transfer/detection apparatus 16 includes a plurality of individually controlled second process sub-paths or heat transfer/detection paths 16b. Each of the heat transfer/detection paths 16b may be dedicated to a particular item of interest in a manner substantially similar to the construction of the Abbott Prism's instrument.

Figure 23:
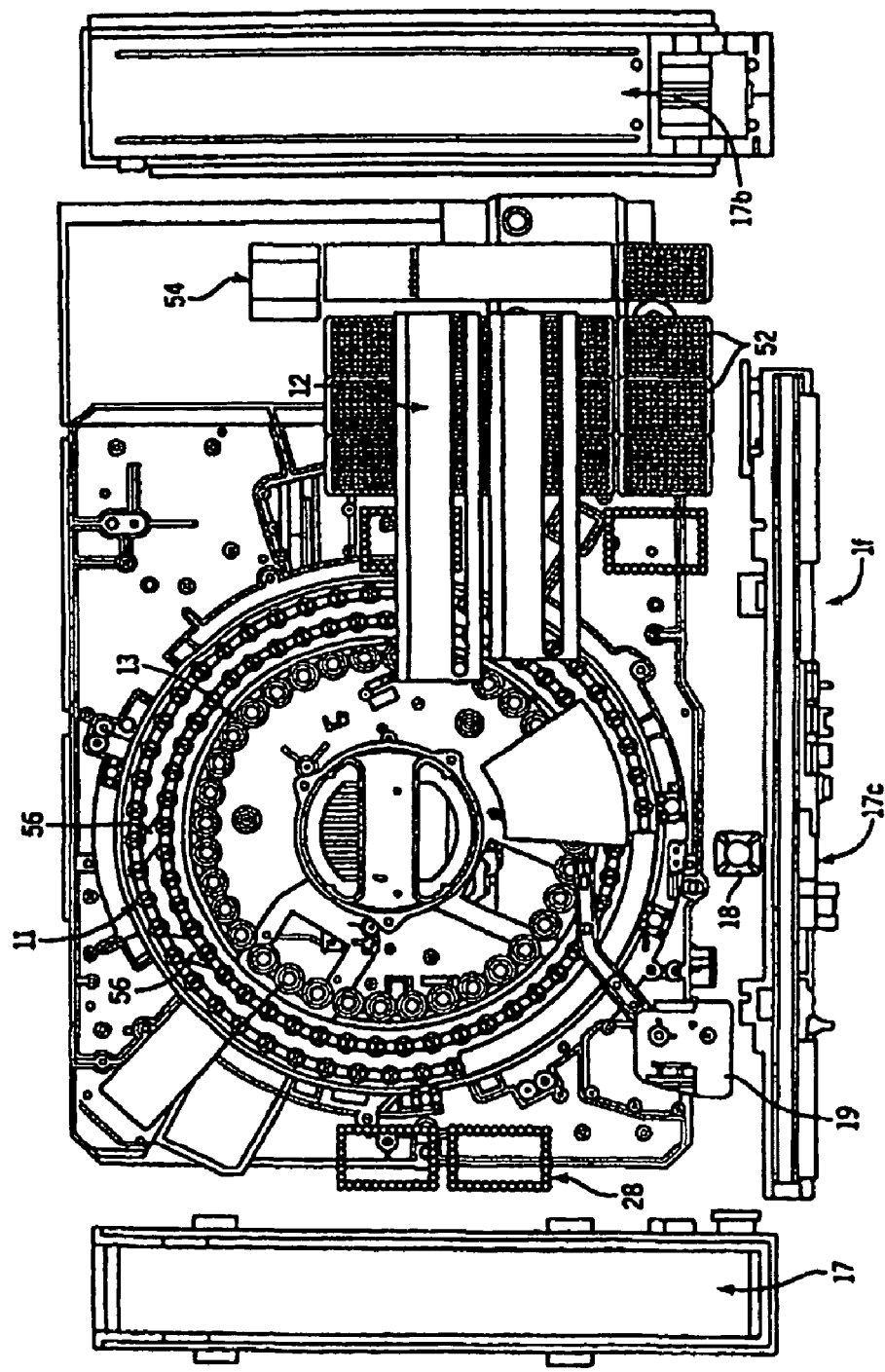
FIG. 23 is a top view of another apparatus substantially similar to the apparatus of FIG. 22.

In an additional apparatus 140 depicted in FIG. 23, processing of the contents of the first container 1 can be preformed and the processed first container contents transferred into a reaction vessel or tray 52, such as a multiple well (e.g. ninety-six wells) tray filled with desired reagents. The apparatus 140 also includes a bypass region 56 on the first process path 11, as described in U.S. Pat. No. 5,795,784. The tray may be sealed and moved to an output queue 54 for transfer, either manual or automatic, to further apparatus such as heat transfer/detection apparatus 16. In this modification, further methods may be employed to improve customer lab workflow by sorting samples by desired assay in a sample handling queue 17 prior to further processing. This allows for consolidation of heating and cooling devices (e.g., consolidation of the number of modules 16a within the heat transfer/detection apparatus 16) needed to process chemistry requiring different heating and cooling protocols for each assay.

The structures described herein and their use may be optimized. For example, the structures may be adjusted such that number of determinations in a given time period are increased, by allocating items such as determinations to be performed, samples, reagents, containers, etc., across elements of the structure(s). Specifically, an operator may loads sample on the sample handler 17 of the structure in any order. To reduce cost per determination or to improve structure reliability, among other things, the number of items present in a structure may be reduced. Some determinations, for example DNA/RNA amplification and detection, require heating and cooling protocols that may vary from determination to determination. This may complicate cost and/or item reduction. To achieve these reductions, items may be allocated across elements of the structure(s).

In the embodiments discussed herein, a determination method may consist of a number of processes, such as a first process, a second process and a third process. The first process may be common to all determinations, such as DNA/RNA sample preparation, sample incubation, immunodiagnostic sample preparation and determination and the like. The second process (e.g., amplification and the like) may be specific to a given determination. The third process (e.g., detection) may be either common to all determinations or specific to a given determination.

To allocate items across elements of the structure(s), samples are identified and then grouped by commonality in second and third processes. For example, one DNA/RNA assay may be processed according to one protocol, such as Protocol A described below, in one module 16a, 16b, 16c or 16d while another DNA/RNA assay may be processed according to another protocol, such as Protocol B described below, in another module 16a, 16b, 16c or 16d. By supplying samples, selected by common second and third processes, from sample handler 17 to process path 11, allocation of modules 16a, 16b, 16c or 16d to specific determination(s) may be achieved while reducing the number of modules 16a, 16b, 16c or 16d and containers 52 needed, while increasing throughput.

Sample sorting may comprise identifying sample information by reading a bar code on the container 8 held by the sample handler 17 with a barcode reader. The containers 8 may then be sorted (mechanically) with other containers 8 within a given carrier 27 and then carriers 27 may be sorted with other carriers 27 in the sample handler 17 by determinations having common second and third processes. After sorting, samples from the containers 8 are transferred to the first containers 1 by a pipettor 19. Alternately, sample sorting may be achieved by pipettor 19 selectively transferring sample from the containers 8 to the first containers 1 on the process path 11 based on predetermined, sorted order.

Once the sample is in the container 1 on the process path 11, the first process comprising the determination method is performed. After the first process is finished, depending on the particular structure used, the second and/or third processes may occur in either the process path 11, in one or more modules 16a, 16b, 16c or 16d, or in a separate apparatus.

By sorting or grouping samples according to common second and/or third process, an optimal number of modules 16a, 16b, 16c or 16d can be allocated to determining a given item of interest, viz. the greatest number of determinations of a given item of interest can be discerned, associated samples can be suitably sorted, and elements or items of or in the structure(s), such as containers, reagents and the like, can be appropriately duplicated over two or more modules 16a, 16b, 16c or 16d on a given structure(s). Similarly, two or more modules 16a, 16b, 16c or 16d can be duplicated based on specific determination protocols.

Figure 24:
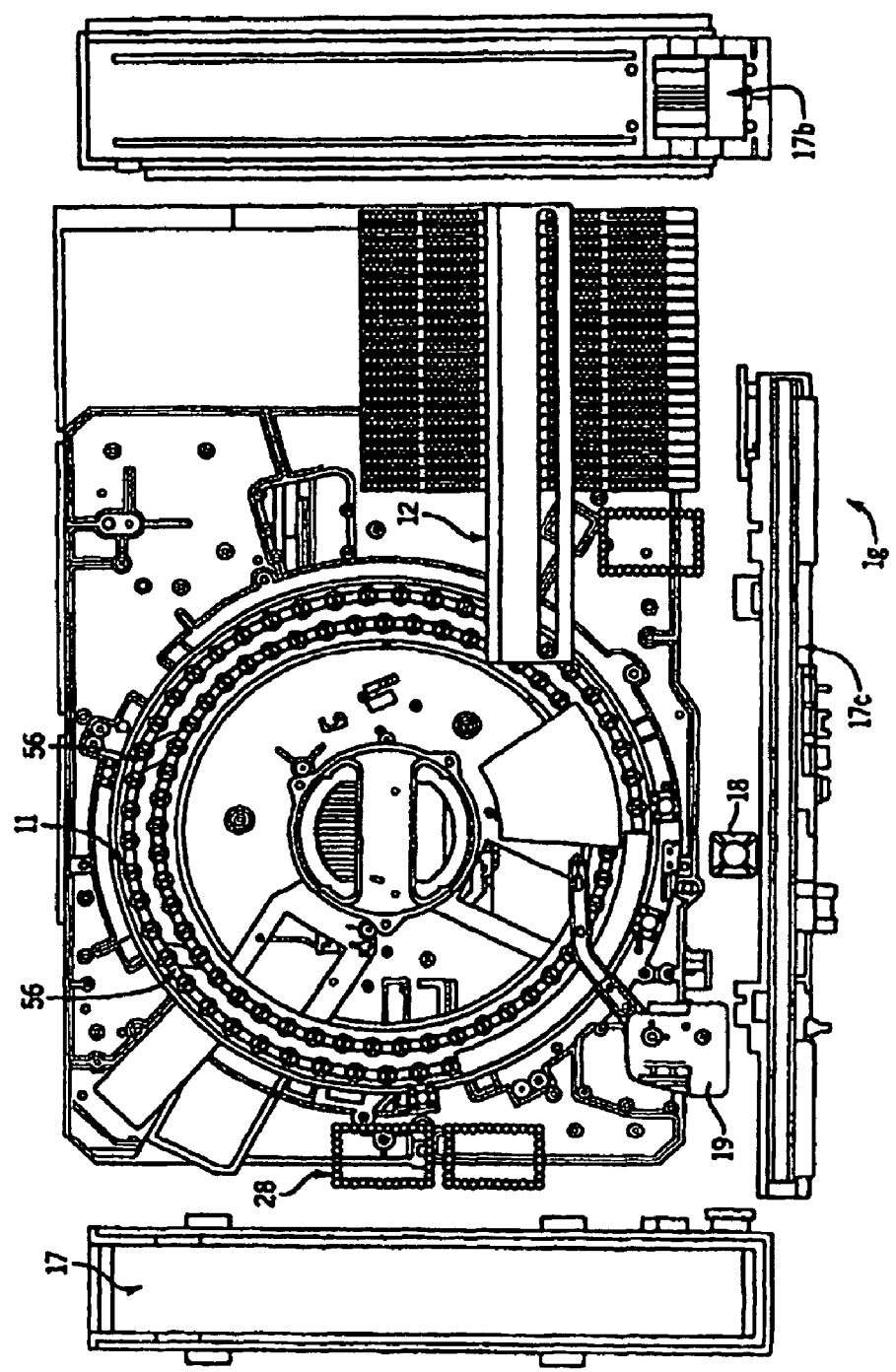
FIG. 24 is a top view of yet a further apparatus substantially similar to the apparatus of FIG. 23.

FIG. 22 shows an apparatus 130 in which the modules 16b can be duplicated according to sample sorting outcomes. FIGS. 23 and 24 show other apparatuses 140 and 150 where modules 16 can be located exterior to the apparatus(s). Here, sorted samples can be duplicated across multiple modules 16 exterior to the apparatus(s) 140 and 150.

FIG. 20 shows an apparatus 110 where the module 16 is integrated into the process path 11. Sample sorting here allows for the process path 11 to be programmed for one determination for a first period of time and then be programmed for another determination for a second period of time.

In applications involving sorting samples by determination in sample handling queue 17 prior to further processing, it may be desirable to form relatively small groupings. The grouping size can determine the size of tray 52 and its corresponding heat transfer/detection apparatus 16. In an apparatus 170 depicted in FIG. 26, samples may be sorted by determination into relatively small groupings (e.g., about twelve samples). The tray 52 and thermal cycling/detection module 16c within thermal cycling/detection module 16 are both configured to accommodate groupings of twelve, with module 16c providing individual control of each grouping of twelve. The apparatus 170 may reduce the number of thermal cycling/detection modules 16c required to maintain desired throughput.

Additional enhancements, such as with software controlling the apparatus, can be provided to manage test distribution lists, to generate reagent load maps, to make reagent loading suggestions, and to manage data.

In the apparatus 150 shown in FIG. 24, preparation of the contents of the first container 1 may be preformed and the prepared first container contents may be transferred into another container or tray. The container 1 is moved to an output queue for manual or automatic transfer to further apparatus that performs reagent addition, heat transfer, and detection.

Figure 25:
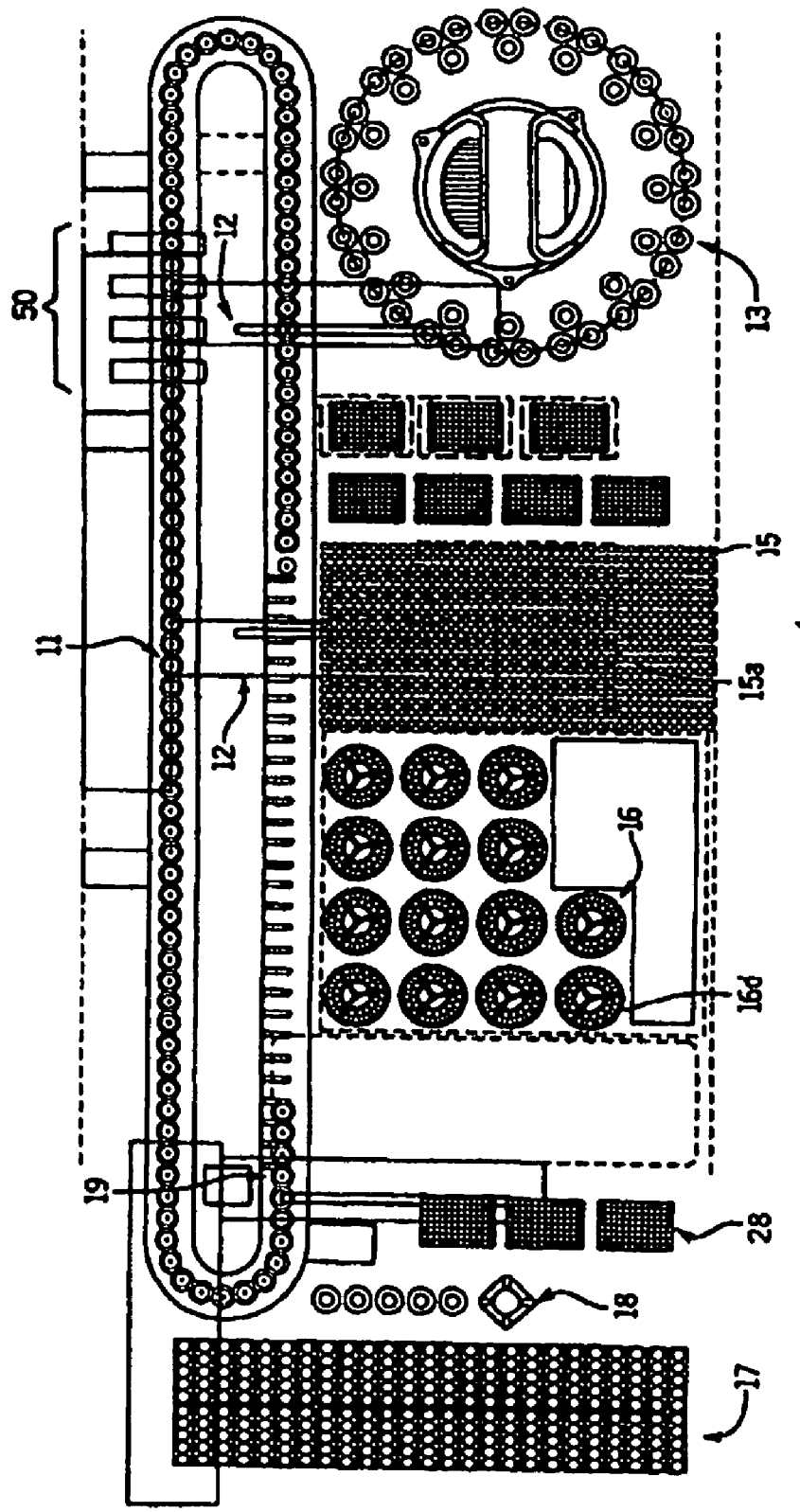
FIG. 25 is a top view of yet a further apparatus similar to the apparatus of FIGS. 3A and 3B.

In the apparatus 160 depicted in FIG. 25, samples do not need to be sorted in sample input queue 17, and the number of thermal cycling/detection modules 16d required is reduced. In this apparatus 160, the second container 15 is transferred to the thermal cycling module 16d, each module 16d being individually controlled and each having a detector. The module 16d may thermally transfer the second container 15 through a plurality (e.g., about two or three) of thermal zones within a carousel over a number of positions. One position on the carousel contains a detector. The module 16d is designed to accept additional containers 15 sequentially while other containers 15 are being processed within the module 16d. Alternately, the module 16d can be fully loaded with the containers 15 and all containers processed substantially simultaneously.

Other embodiments of the module 16d are illustrated in FIGS. 30A, 30B, 31, 32A and 32B. Common reference numbers are used to indicate similar structures in FIGS. 30A, 30B, 31, 32A and 32B. These other embodiments of the module 16d can be used for thermal amplification and detection of PCR products, for example.

A tray 70 has at least one compartment or well 71 where thermal amplification can occur. While the embodiments of FIGS. 30B and 32B include eight wells 71, the number of wells 71 can be modified as desired. The well 71 can be numbered and may be bar coded to facilitate identification. In this manner, well 71 position, contents, etc. can be checked by machine, such as with optics. In some embodiments, the tray 70 may be a disposable item easily removed from the associated structure.

A well 71 may be bounded on at least one side by a divider 72 to reduce exposure of contents of a well 71 to a contaminant. To further reduce exposure to a contaminant, the well 71 may be removably covered or sealed.

The tray 70 is operatively connected with a motor 76 (FIG. 31) (e.g., a stepping motor, a servo motor or the like controlled by a microprocessor and the like) by a drive shaft 73 thereby providing for desired, controlled rotation of the tray 70.

Figure 30A:
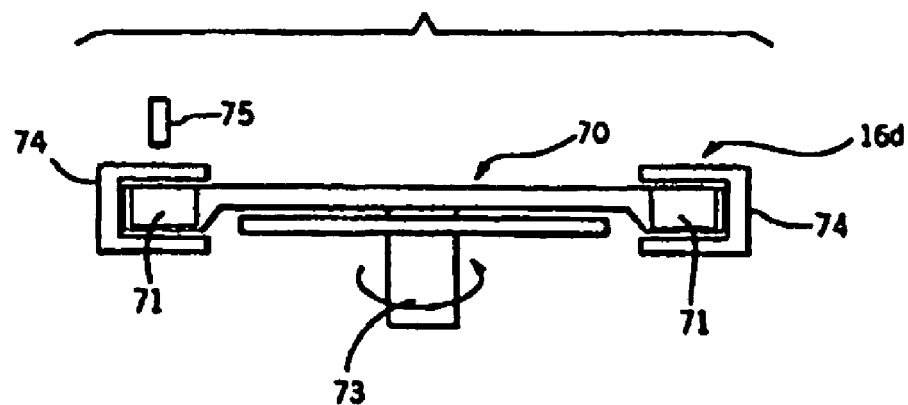
FIG. 30A is a sectional view of a thermal cycling module usable with the present invention.
Figure 30B:
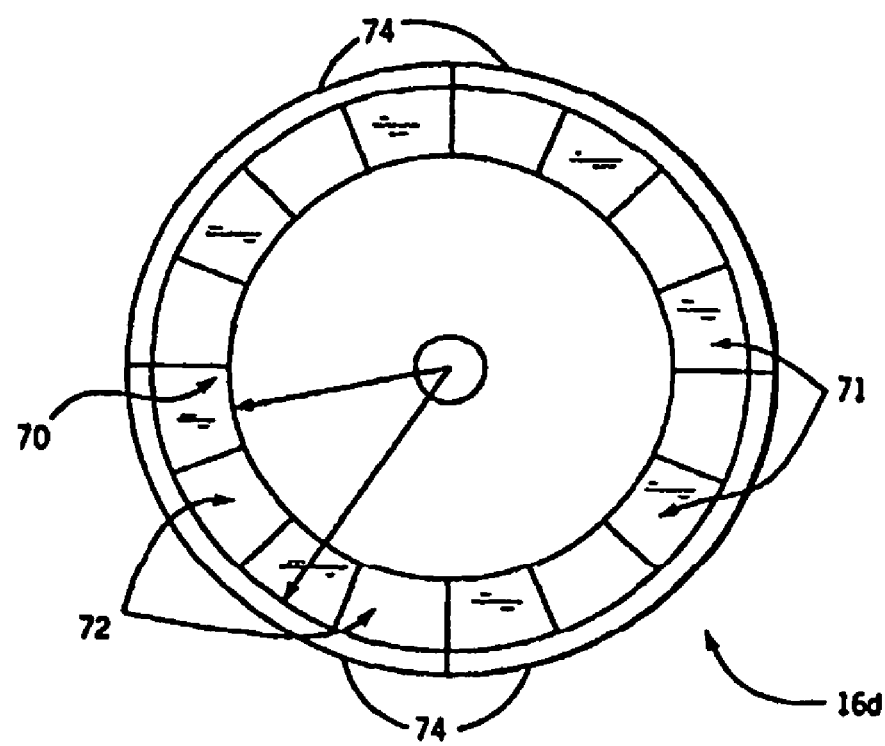
FIG. 30B is a top view of module of FIG. 30A.

The contents of the container 8 can be transferred from the first process path 11 to the well 71 for amplification and detection. To provide desired thermal exposure of the tray 70 and the well 71, at least one heater 74 is thermally associated with the tray 70. If multiple or different thermal exposures are desired, then an appropriate number of heaters 74 can be included. As shown in FIGS. 30B and 32B, four (4) heaters 74 are disposed in thermal association with the tray 70 thereby providing four different temperatures or different thermal exposures. The heater 74 may utilize electric, microwave, Peltier effect, forced air or similar technology.

The heater 74 may operate such that the well 71 is at a desired temperature prior to or after addition of contents to the well 71. In some embodiments, the heater 74 may be separated from the tray 70 such that the tray 70 is operatively connected with the heater 74 either prior to or after addition of contents to the well 71 on the tray 70.

As the tray 70 rotates, the well 71 and its contents are exposed or brought to the temperature provided by the adjacent heater 74. As thermal variations may be cyclical (i.e., repetitive of a given pattern), rotation of the tray 70 can bring the well 71 and its contents to desired temperature(s) in desired sequence for a desired time period. Thus, the well 71 and its contents can experience consecutive, well-defined temperature zones as the tray 70 rotates. Each heater 74 may correspond to temperatures specific to a given reaction, such as melt, annealing, extension, etc., defined by the particular determination being performed.

A time period during which a given well 71 is located adjacent a given heater 74 is determined by the rotational speed of the tray 70. In some utilizations, a number of rotations or step-wise movements of the tray 70 may be proportional to a number of cycles performed by a currently available thermal cycler. Rotational speed of the tray 70 may be controlled such that the well 71 is positioned adjacent a heater 74 for a specified length of time. For example, a first heater 74 may bring the well 71 to a temperature capable of dissociating, or melting, double stranded DNA strands. A second heater 74, adjacent the first heater 74, may bring the well 71 to a temperature that induces association of complementary strands, such as a target and a primer, or a target and a probe. The second heater 74 or another heater 74 may be used to allow enzymatic polymerase elongation of the primer, and the well 71 is positioned adjacent that heater 74 for a time sufficient for the reaction to finish. By adjusting tray 70 rotational speed, thermal "area" of the heater 74 (i.e., the area in which the heater 74 can bring the well 71 and its contents to a temperature associated with the heater 74), and temperature values associated with the heater 74, optimal thermal cycling parameters for a certain assay may be accomplished.

Once the desired thermal exposure of the well 71 is complete, the item of interest present in the well 71 can be detected by detector 75. If the well 71 is sealed, then the seal may be removed or, alternatively, the seal may be made of a material that allows optical transmission so that the detector 75 can monitor the well 71 and detect the item of interest, if present. The detector 75 may also read a bar code associated with the tray 70 or the well 71.

The detector 75 may be used in a dynamic (real time) mode, such as to detect, in real time, PCR products by reading the well 71 as it moves with respect to the detector 75. In some embodiments, the detector 75 may read the well 71 every n times the well 71 encounters the detector 75. The number n may be determined to allow for comparing status of the well 71 with a predetermined threshold at a predetermined time(s). The detector 75 can also be used for static, end point reads.

The detector 75 may be stationary with respect to the tray 70 or may move with respect to the tray 70. If multiple trays 70 are present, then multiple detectors 75 (e.g., one detector 75 for each tray 70) may be used. Fiber optics may be used to channel light from a well 71 to the detector 75.

The detector 75 may use a light source to illuminate the contents of a well 71 at a single or multiple wavelengths, thereby accommodating multiplex detector 75 data reduction of multiple wavelength emission intensity at discrete wavelengths, for example. In some embodiments, the detector 75 may provide single or parallel detection of single or multiple wavelengths, such as fluorescence emissions from the well 71.

Figure 33:
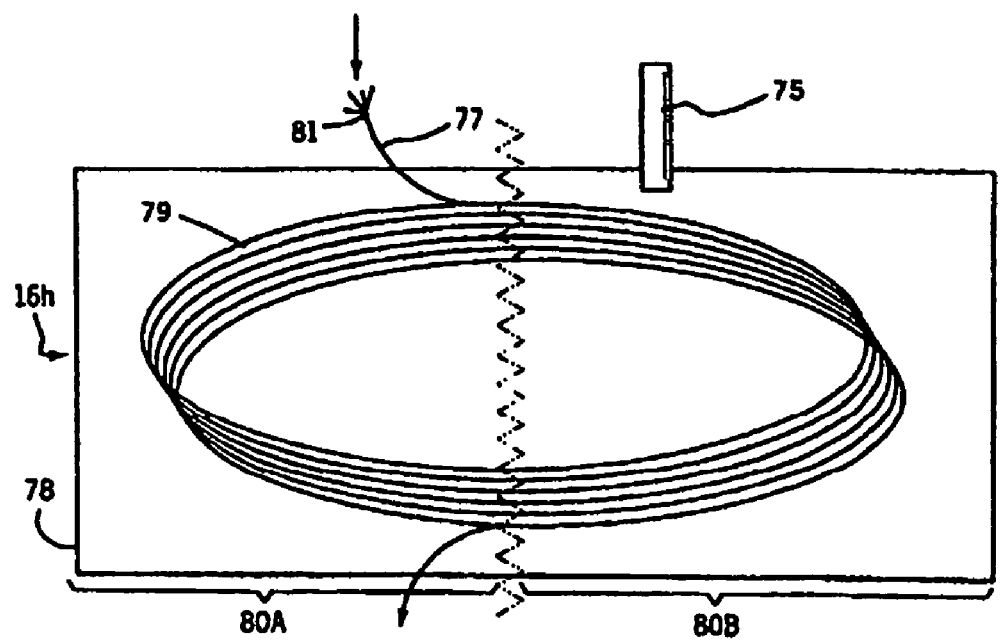
FIG. 33 is a generic plan view of still another thermal cycling module.

Another module 16*h* is shown in FIG. 33. This module 16*h* includes a fluid conveying conduit 77 disposed within a block 78. The conduit 77 may be formed as a coil 79 in the block 78. The block 78 is constructed with suitable thermal energy conductive elements to form at least a first thermal zone 80A having a first temperature and a second thermal zone 80B having a second temperature different from the first temperature. With this construction, some portions of the coil 79 are in a thermal zone 80A or 80B different than other portions of the coil 79 while some portions of the coil 79 are in the same thermal zone 80A or 80B.

The contents or fluid of a container 1, 8 or 15 may be transferred from the first process path 11 to an inlet 81 of the conduit 77, and the contents or fluid forced to flow from the inlet 81 through the coil 79 by suitable means, such as a pump, capillary action, etc. As the fluid flows through the coil 79, the fluid encounters or is brought to different temperatures as it moves between thermal zones 80A and 80B.

The temperatures associated with the thermal zones 80A and 80B can be chosen to match temperatures of specific PCR amplifications. In this embodiment, a number of turns, or loops, comprising the coil 79 is equivalent to the number of cycles performed by a currently available thermal cycler. The fluid flow in the coil 79 is controlled such that the fluid resides in each thermal zone 80A or 80B a specified length of time. For example, one thermal zone 80B may bring the fluid to a temperature capable of dissociating, or melting, double stranded DNA strands. The other thermal zone 80A may bring the fluid to a temperature inducing association of complementary strands, such as a target and a primer, or a target and a probe. This same thermal zone 80A may be used to allow enzymatic polymerase elongation of the primer. Of course, the fluid flow is adjusted to expose the fluid to a thermal zone 80A or 80B for a time period sufficient for the reaction to finish. A detector 75 is disposed adjacent the coil 79 to monitor status of the fluid within the coil 79 in a manner substantially similar to that described above.

Fluid corresponding to various samples may be introduced to the conduit 77 separated by suitable other fluid, such as air, a buffer and the like.

Any heat transfer/detection module can be used in the apparatus 16. For example, the apparatus 16 can use methods described in U.S. Pat. No. 5,576,218 (assigned to the assignee of the present case), the disclosure of which is hereby incorporated herein in its entirety.

Figure 29:
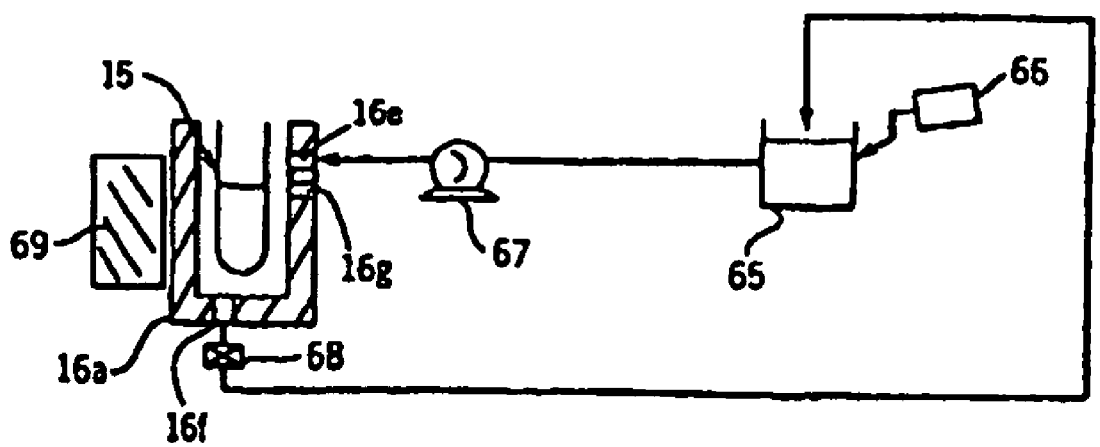
FIG. 29 is a generic view of operation of a portion of the structures described herein.

The module 16a shown in FIGS. 3A and 3B can provide thermal cycling of reaction contents in the second container 15 with use of heated or chilled fluids as shown in FIG. 29. Fluid is stored in the reservoir 65 and heated or chilled by thermal controller 66. Fluid is routed to the module 16a through the port 16e at desired times by metering fan or pump 67. Heat transfer occurs between the contents in the second container 15 and the heated or chilled fluid. The metered amount of fluid transferred to module 16a determines the time the contents in the second container 15 will remain at a given temperature. Evacuation of fluid from the module 16a occurs through the port 16f with use of the valve 68 and/or additional pumps or gravity to the container 65 or to waste. Given that the thermal mass of the second container 15, the contents of the second container 15 and the metered fluid in container 65 are known, the temperature of a metered fluid interaction with the second container 15 may be calculated and predicted thereby reducing a need for temperature control at the interface of the fluid with the second container 15.

Different temperatures of contents in the second container 15 can be achieved (e.g., by adding additional reservoir pumps and ports, such as port 16g shown in FIG. 29). To enhance performance of rapid heat transfer, the second container 15 can be constructed as a pouch out of a thin polymeric film. Also, the thermal element 69 may be positioned adjacent to and in contact with the module 16a and controlled at a desired temperature.

Figure 28:
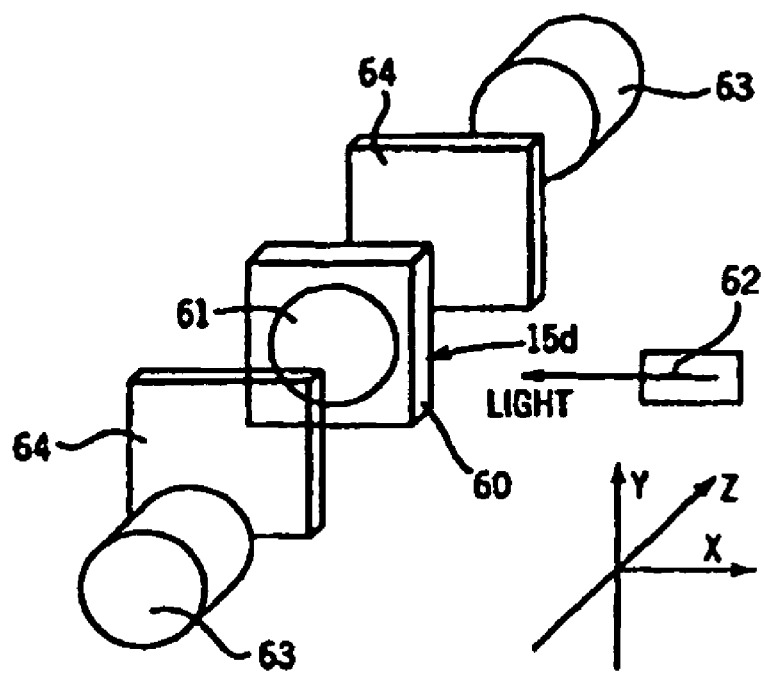
FIG. 28 is a perspective view of an optical configuration usable with the present invention.

Orientation of detector optics to the second container 15 or 15d, for example, may be accomplished any suitable manner, with one suitable way being shown in FIG. 28. As illustrated there, the second container 15d may include at least one first face 60 on a first axis plane, designated "YZ", and at least one second face 61 on a second axis plane, designated "XY". An optical source 62 is located adjacent to the first face 60 and an optical detector 63 is located adjacent to a second face 61 opposite the first face 60 such that excitation of a label associated with an item of interest is induced by the optical source 62 and emission of a signal (e.g., light) from the label is detected by detector or detector pair 63. The relative position of a first axis plane is different from the second axis plane to provide an increased signal collection area. Suitable detectors or detector pairs 63 include a single photodiode, quadrant photodiode, diode array, photomultiplier tube, or any combination of these detection devices. Combining optics with heating elements can be done with use of transparent heating elements 64 mounted in transparent material, such as glass, the heaters being located adjacent to at least one of the second faces of the second container 15d, and possibly lying on the second plane. In some embodiments, the optical source 62 may lie on a plane substantially orthogonal to the detector or detector pair 63. In this optical configuration, the second container 15d may be, for example, a reaction tube supplied by Cepheid of Sunnyvale, Calif., or any reaction container configuration including but not limited to substantially hemispherical, spherical, cubic, or tetrahedron shapes.

It is to be noted that additional first container contents preparation, immunodiagnostic, and/or determination processing modules may be connected together with a common robotic and/or system processor, such as a computer and the like. It should also be noted that the heat transfer/detection apparatus 16 may accept first container contents or other sample, processed or not, from another process path not operatively coupled to the apparatuses 100-170.

The described elements comprising the apparatuses 100-170 may be selectively automatically and/or manually operated at desired times to accomplish a desired determination of an item of interest. The functions of the elements can be performed in any desired order any desired number of times to achieve desired results. The methods of operation and items, such as reagents and the like, used may be substantially similar to those described in U.S. Pat. No. 5,234,809, the disclosure of which is incorporated herein in its entirety.

The following example of a DNA/RNA sample extraction protocol and polymerase chain reaction (PCR) protocol illustrates such an application. The time periods, temperatures, volumes and elements (containers, solutions, reagents, etc.) used can be adjusted as appropriate. The position numbers correspond to the apparatus 100 of FIGS. 3A and 3B. However, the position numbers may also indicate the number of stepwise movements along a process path in the same manner as used to described the various assay formats in U.S. Pat. No. 5,795,784.

| One-Tube DNA/RNA 20-20 Minute Sample Preparation Protocol and One-Tube 1.5 Hour PCR End-Point Protocol | |
|---|---|
| Sample Prep | |
| 0 Seconds - At Position 0: | Instrument loads first container 1 onto first process path 11 |
| 1-36 Seconds - At Position 1: | Pipettor 19 engages a disposable pipette tip 28, aspirates magnetically responsive microparticles (about 0.1 ml) from container 31 in reagent storage area 18, and dispenses those microparticles into first container 1 at Position 1. The disposable pipette tip 28 is washed with fluid in wash cup 23. Pipettor 19 aspirates another reagent (about 0.05 ml), such as an internal control and the like, from a container located in reagent handling area 13, dispenses that reagent into first container 1, and disposable pipette tip 28 is washed with fluid in wash cup 23 a second time. Sample (about 1 ml) disposed in container 8 is aspirated by pipettor 19 and dispensed into first container 1. Disposable pipette tip 28 is removed from pipettor 19 and deposited in tip waste 24. Alternately, the pipettor wash performed after microparticle dispense can be eliminated. In this case, microparticles and internal control are aspirated and dispensed into first container 1 substantially simultaneously or sequentially. Alternatively, a subset of or all liquid |

-continued

One-Tube DNA/RNA 20-20 Minute Sample Preparation Protocol and One-Tube 1.5 Hour PCR End-Point Protocol

Figure 5A:
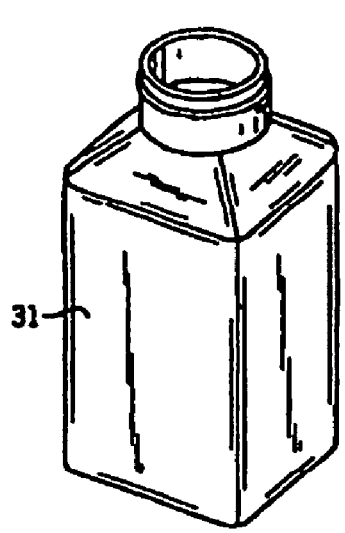
FIGS. 5A through 5F are perspective views of various components which may be used with the apparatus shown in FIGS. 3A and 3B.
Figure 5B:
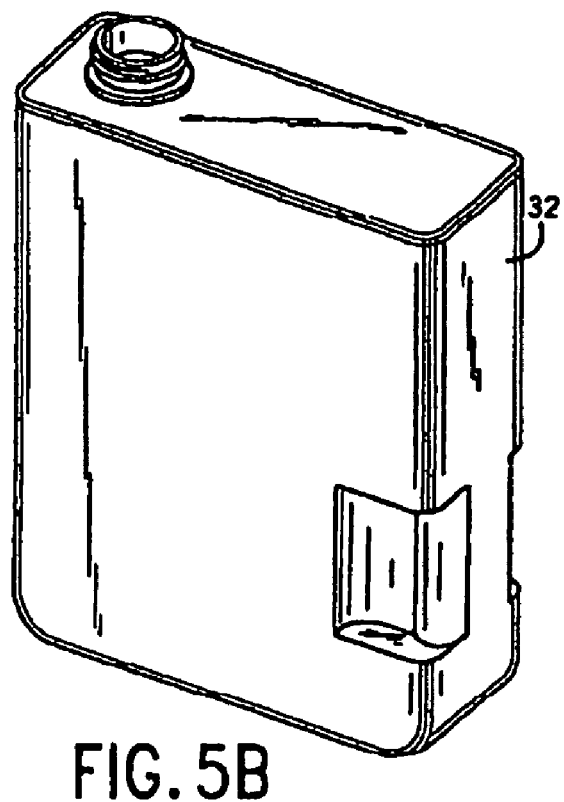
Figure 5C:
Figure 5D:
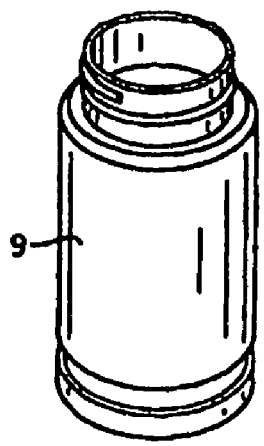
Figure 5E:
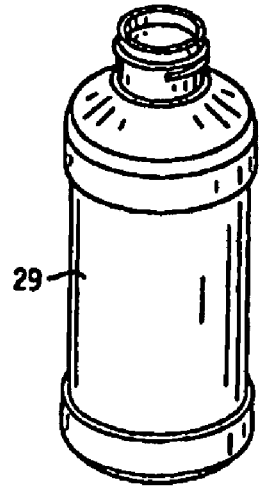
Figure 5F:
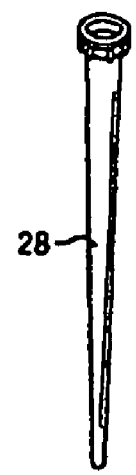
Figure 19:
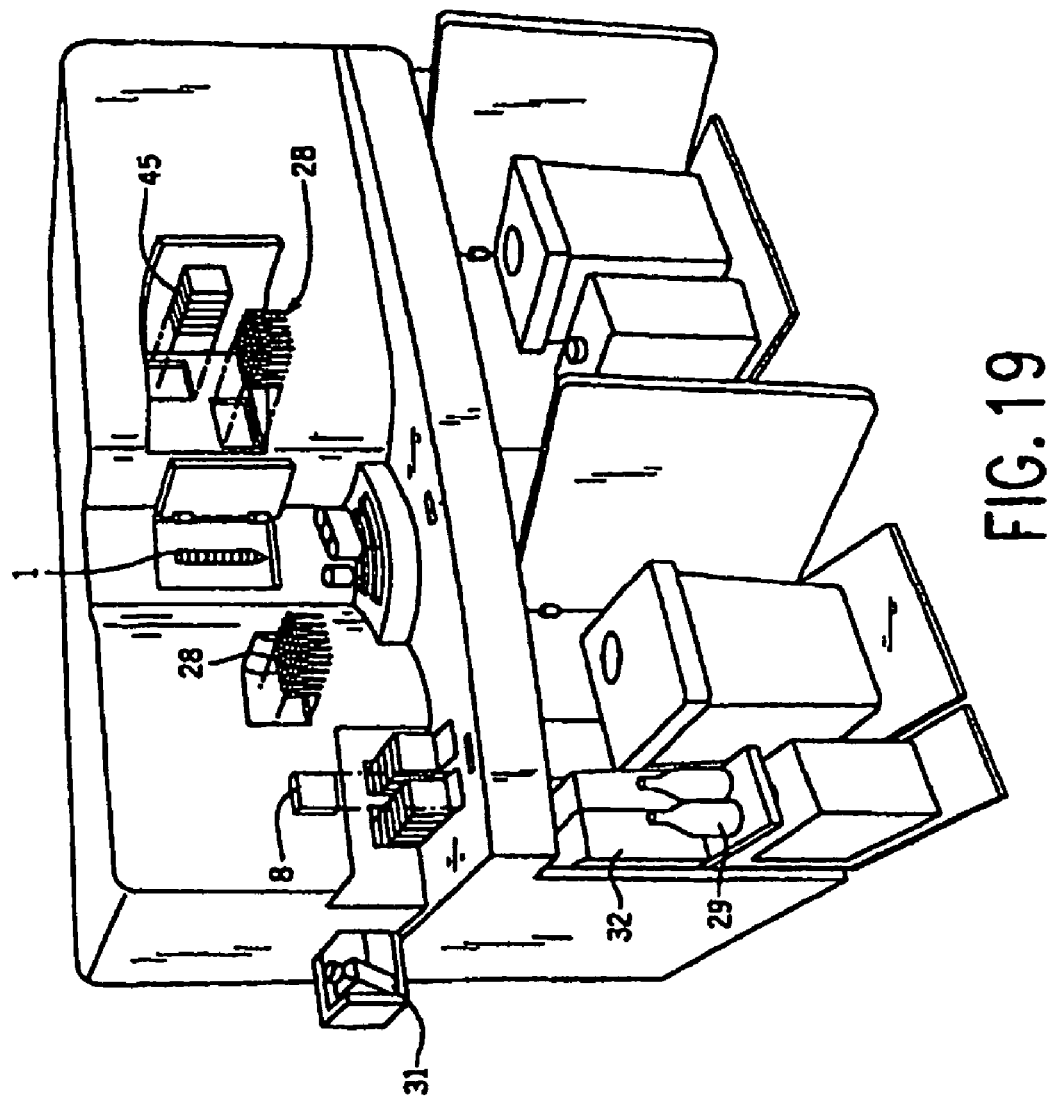
FIG. 19 is an isometric view of an apparatus substantially similar to the apparatus of FIG. 18.

| | |
|---|---|
| | washes can be eliminated, in which case, microparticles, internal controls and sample may be aspirated and simultaneously and/or sequentially dispensed into first container 1. |
| 37-72 Seconds - At Position 2: | A dispense nozzle coupled to first process path 11 is fluidically connected to a reagent container, such as reagent bottle 32 as shown in FIGS. 5B and 19, containing a lyse solution. About 6 mL of lyse solution is dispensed, either at room temperature or at about 37 degrees Celsius, to the first container 1. |
| 73-108 Seconds - At Position 3: | Contents of first container 1 are mixed with mixer 5. First container 1 contents are incubated at about 37 degrees Celsius. |
| 109-1260 Seconds - At Positions 4 through 35: | Continue incubation for about 19.8 minutes at about 37 degrees Celsius. First container 1 contents are mixed at about 648 seconds and at about 1224 seconds. Periodic mixing of first container 1 contents enhances reaction. |
| 1261-1296 Seconds - At Position 36: | Item of interest bound to microparticles are captured on side wall of first container 1 with magnet 4. |
| 1297-1332 Seconds - At Position 37: | Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. A wash solution (buffer) is dispensed from the probe 49 into the first container 1. Probe 49 is washed. Alternately, wash functions performed separately at, e.g. positions 36 and 37 can be combined at one position on first process path 11. |
| 1333-1368 Seconds - At Position 38: | Probe 49 performs wash and dispense functions. Mixer 5 provides resuspension of microparticles into fluid, specifically wash solution #1 in this example, in the first container 1. Alternately, resuspension of microparticles can be accomplished with appropriate fluid dispense into first container 1 as described above with respect to FIG. 17. Alternatively, functions performed at positions 36, 37, and/or 38 can be combined at one position on first process path 11. |
| 1369-1404 Seconds - At Position 39: | Item of interest bound to microparticles are captured on side wall of first container 1 with magnet 4. Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. Probe 49 is washed. Alternately, wash functions performed separately at, e.g. positions 36 and 37 can be combined at one position on first process path 11. |
| 1405-1440 Seconds - At Position 40: | Probe 49 performs wash and dispense functions. Mixer 5 provides resuspension of microparticles into fluid in the first container 1. Alternately, resuspension of microparticles can be accomplished with appropriate fluid dispense into first container 1 as described above with respect to FIG. 17. Functions performed at positions 36, 37, and/or 38 can be combined at one position on first process path 11. |
| 1441-1476 Seconds - At Position 41: | Item of interest bound to microparticles are captured on side wall of first container 1 with magnet 4. Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. A wash solution (buffer) is dispensed from the probe 49 into the first container 1. Probe 49 is washed. Alternately, wash functions performed separately at, e.g. positions 36 and 37 can be combined at one position on first process path 11. |
| 1477-1512 Seconds - At Position 42: | Probe 49 performs wash and dispense functions. Mixer provides resuspension of microparticles into fluid, specifically wash solution #2 in this example, in the first container 1. Alternately, resuspension of microparticles can be accomplished with appropriate fluid dispense into first container 1 as described above with respect to FIG. 17. Functions performed at positions 36, 37, and/or 38 can be combined at one position on first process path 11. |
| 1513-1548 Seconds - At Position 43: | Item of interest bound to microparticles are captured on side wall of first container 1 with magnet 4. Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. A wash solution (buffer) is dispensed from the probe 49 into the first container 1. Probe 49 is washed. Alternately, wash functions performed separately at, e.g. positions 36 and 37 can be combined at one position on first process path 11. |

| One-Tube DNA/RNA 20-20 Minute Sample Preparation Protocol and One-Tube 1.5 Hour PCR End-Point Protocol | |
|---|---|
| 1549-1584 Seconds - At Position 44: | Probe 49 performs wash and dispense functions. Mixer 5 provides resuspension of microparticles into fluid, specifically wash solution #2 in this example, in the first container 1. Alternately, resuspension of microparticles can be accomplished with appropriate fluid dispense into first container 1 as described above with respect to FIG. 17. |
| 1584-1620 Seconds - At Position 45: | Item of interest bound to microparticles are captured on side wall of first container 1 with magnet 4. Elements comprising the wash zone 50 perform wash functions, described herein, comprising magnetic separation and aspiration and dispense of fluids with probe 49. Specifically, microparticles are separated from the remainder of first container 1 contents by magnet 4 and probe 49 removes the unseparated first container 1 contents. Probe 49 is washed. Alternately, wash functions performed separately at, e.g. positions 36 and 37 can be combined at one position on first process path 11. |
| 1621-1656 Seconds - At Position 46: | A pump, operatively associated with the first process path 11, connected fluidly with a dispense nozzle, and fluidly coupled with the first process path 11, and a reagent container, such as container 29 shown in FIGS. 5E and 19, induces dispense of a fluid, such as an elution reagent, to first container 1. In one embodiment, about 80 μL of elution reagent is dispensed at ambient temperature or, alternately, at about 70 degrees Celsius. |
| 1657-2844 Seconds - At Positions 47-76: | First container 1 contents are incubated, for a period of about 19.8 minutes, in this example at about 37 degrees Celsius, or at a temperature substantially within the range of about 50 to about 70 degrees Celsius. Periodic mixing enhances reactions among elements of the first container 1 contents. Elution reagent releases the item of interest from the microparticles. |
| Assay | |
| 2845-2880 Seconds - At Position 77: | At position 76, pipettor 12 engages a disposable pipettor tip 28, aspirates a first reagent from a container in reagent storage area 13, and dispenses that reagent into second container 15 on container processor line 15a. The disposable pipette tip 28 is washed with fluid in wash cup 24. Pipettor 12 aspirates a second reagent from a container in reagent handling area 13, dispenses the second reagent into second container 15, and disposable pipette tip 28 is washed with in wash cup 24. A third reagent is aspirated into pipette tip 28 from a container in reagent handling area 13, and the first container 1 contents containing the item of interest, about 50 μL, is aspirated from first container 1 in position 77 of first process path 11 to the pipette tip 28. The third reagent and the aspirated first container 1 contents are dispensed from the pipette tip 28 into second container 15 and pipettor 12 ejects disposable pipette tip 28 to tip waste 24. Alternately, the third reagent can be dispensed into first container 1 on first process path 11 at position 76 by pipettor 12 or by another dispense nozzle on the first process path 11. In another embodiment, the first reagent and second reagent aspirations can be completed, without washing the pipettor 12 between aspirations, and the reagents can be dispensed into second container 15 substantially simultaneously. The volumes of each of the three reagents may be substantially within the range of about 10 to about 50 μL. If it were desired to detect more than one item of interest in a given sample, portions of the contents of first container 1 can be transferred to a corresponding number of containers 15. These multiple transfers of first container 1 contents may occur from position 77 or, alternatively, may occur from position 77 and subsequent position(s). If a relatively large number, such as about 15, of items of interest are to be determined from one sample, then multiple aspirations and dispenses can occur from container 8 and/or first container 1 by pipettors 19 and/or 12. |
| 2881-2916 Seconds - | Second container 15 is transported on the container processor line 15a to the sealer 21 where the second container 15 is sealed. The sealed second container 15 is transported to the spinner 22 where the contents in the upper portion of second container 15 are moved to the lower portion of second container 15. |
| 2917-2952 Seconds - | A robot engages second container 15, and places the second container 15 in a heat transfer/detection module 16a where the second container 15 is exposed to a thermal cycle and the item of interest in the second container 15 is detected. |
| 2953-8352 Seconds - | Assay Specific Thermal Cycling Protocols: Second container 15 undergoes a thermal cycling protocol as specified. The following are a few examples of such a protocol. |
| Protocol A | |
| | 1. about 59 degrees Celsius for about 30 minutes. One cycle
2. about 95 degrees Celsius for about 30 seconds, about 54 degrees Celsius for about 30 seconds, about 72 degrees Celsius for about 30 seconds. 4 cycles |

| | One-Tube DNA/RNA 20-20 Minute Sample Preparation Protocol and One-Tube 1.5 Hour PCR End-Point Protocol |
|---|---|
| | 3. about 90 degrees Celsius for about 30 seconds, about 59 degrees Celsius for about 30 seconds, about 72 degrees Celsius for about 30 seconds. 46 cycles<br>4. about 94 degrees Celsius for about 5 minutes, about 45 degrees Celsius for about 15 minutes, about 25 degrees Celsius for about 10 min. 1 cycle |
| | Protocol B |
| | 1. about 94 degrees Celsius for about 10 minutes. One cycle.<br>2. about 94 degrees Celsius for about 1 minute, about 58 degrees Celsius for about 1 minute. 45 cycles.<br>3. about 58 degrees Celsius for about 10 minutes, about 94 degrees Celsius for about 5 minutes, about 55 degrees Celsius for about 15 minutes, about 25 degrees Celsius and maintain. |
| | Protocol C |
| | 1. about 95 degrees Celsius for about 9.5 minutes. One cycle.<br>2. about 95 degrees Celsius for about 30 seconds, about 59 degrees Celsius for about 1 minute. 41 cycles.<br>3. about 95 degrees Celsius for about 3 minutes, about 25 degrees Celsius for about 10 minutes. One cycle |
| 8353-8388 Seconds - | After completion of the particular thermal cycling protocol selected, the item of interest in the second container 15 is detected and the second container 15 is disposed. A result of the above steps is reported. |

In any of the embodiments described herein, lysis may include use of induced electrical pulse(s) or sonication whereby such pulsing causes DNA/RNA to be exposed in undamaged form prior to binding.

In addition to the above-disclosed DNA/RNA method or protocol, the method performed by the apparatuses 100-170 may be an immunodiagnostic method. For example, U.S. Pat. No. 5,795,784 lists various methods or formats that may be executed with the above-disclosed apparatuses 100-170 with appropriate modification. Furthermore, DNA/RNA extraction may be amplified and detected with the apparatuses 100-170, or alternately transported to another apparatus 100 or a different apparatus, such as those disclosed in U.S. Pat. No. 5,795,784 and the like, for further processing. It is understood that the first container 1 may be sealed by suitable means, if desired.

In another embodiment, the contents of the first container 1, after processing discussed above, may be transferred from Position 76 on the first process path 11 to a suitable optical flow cell on the apparatus. The optical flow cell may be substantially similar to that described in the following U.S. Pat. Nos. 5,589,394, 5,601,234, 5,631,165, 5,631,730, 5,656, 499, 5,812,419, and 5,891,734, the disclosures of which are all incorporated by reference herein in their entirety. The item of interest in the sample can be detected with the optical flow cell.

In a modification of this embodiment, a sample can be transferred directly from first container 1, 8, 15, or another sample carrying vessel to a sample receiving cups on the apparatus. The sample can be mixed and suitably incubated with a reagent containing a label. The reagent may be formulated such that the label encounters or passes through cell and/or nuclear membranes in the sample, thereby permitting the label to bind or otherwise to become associated with the item of interest in the sample irrespective of where the item of interest is located within the sample. If the label encounters no item of interest in the sample (e.g., if no item of interest is present in the sample or if all items of interest in the sample are already associated with a label), then the label or excess label can be removed by suitable methods, such as separation, washing, etc. The sample, possibly containing an item of interest associated with a label, is passed to the optical flow cell on the structure and the label is detected by optics associated with the flow cell thereby indicating presence of the item of interest.

Advanced Magnetic Handling

In any of the embodiments described herein, lysis may include use of induced electrical pulse(s) or sonication whereby such pulsing causes nucleic acids (e.g., DNA and RNA) to be exposed in substantially undamaged form prior to binding.

In addition to the above-disclosed nucleic acid method or protocol, the method performed by the apparatuses 100-170 may be an immunodiagnostic method. For example, U.S. Pat. No. 5,795,784 lists various methods or formats that may be executed with the above-disclosed apparatuses 100-170, possibly with appropriate modification. Furthermore, the extracted DNA and/or RNA may be amplified and detected with the apparatuses 100-170, or alternately transported to another apparatus 100 or a different apparatus, such as those disclosed in U.S. Pat. No. 5,795,784 and the like, for further processing. The first container 1 optionally may be sealed by suitable means.

In another embodiment, the contents of the first container 1, after processing discussed above, can be transferred from Position 76 on the first process path 11 to an optical flow cell on the structure. The optical flow cell is substantially similar to that described in the following U.S. Pat. Nos. 5,589,394, 5,601,234, 5,631,165, 5,631,730, 5,656,499, 5,812,419, and 5,891,734, the disclosures of which are all incorporated by reference herein in their entirety. The item of interest in the sample can be detected with the optical flow cell.

In a modification of this embodiment, a sample can be transferred directly from first container 1, 8, 15, or another sample carrying vessel to a sample receiving cups on the apparatus. The sample can be mixed and suitably incubated with a reagent containing a label. The reagent may be formulated such that the label encounters or passes through cell and/or nuclear membranes in the sample, thereby permitting the label to bind or otherwise to become associated with the item of interest in the sample irrespective of where the item of interest is located within the sample. If the label encounters no item of interest in the sample (e.g., if no item of interest is present in the sample or if all items of interest in the sample are already associated with a label), then the label or excess label can be removed by suitable methods, such as separation, washing, etc. The sample, possibly containing an item of interest associated with a label, is passed to the optical flow cell on the structure and the label is detected by optics associated with the flow cell thereby indicating presence of the item of interest.

Figure 34:
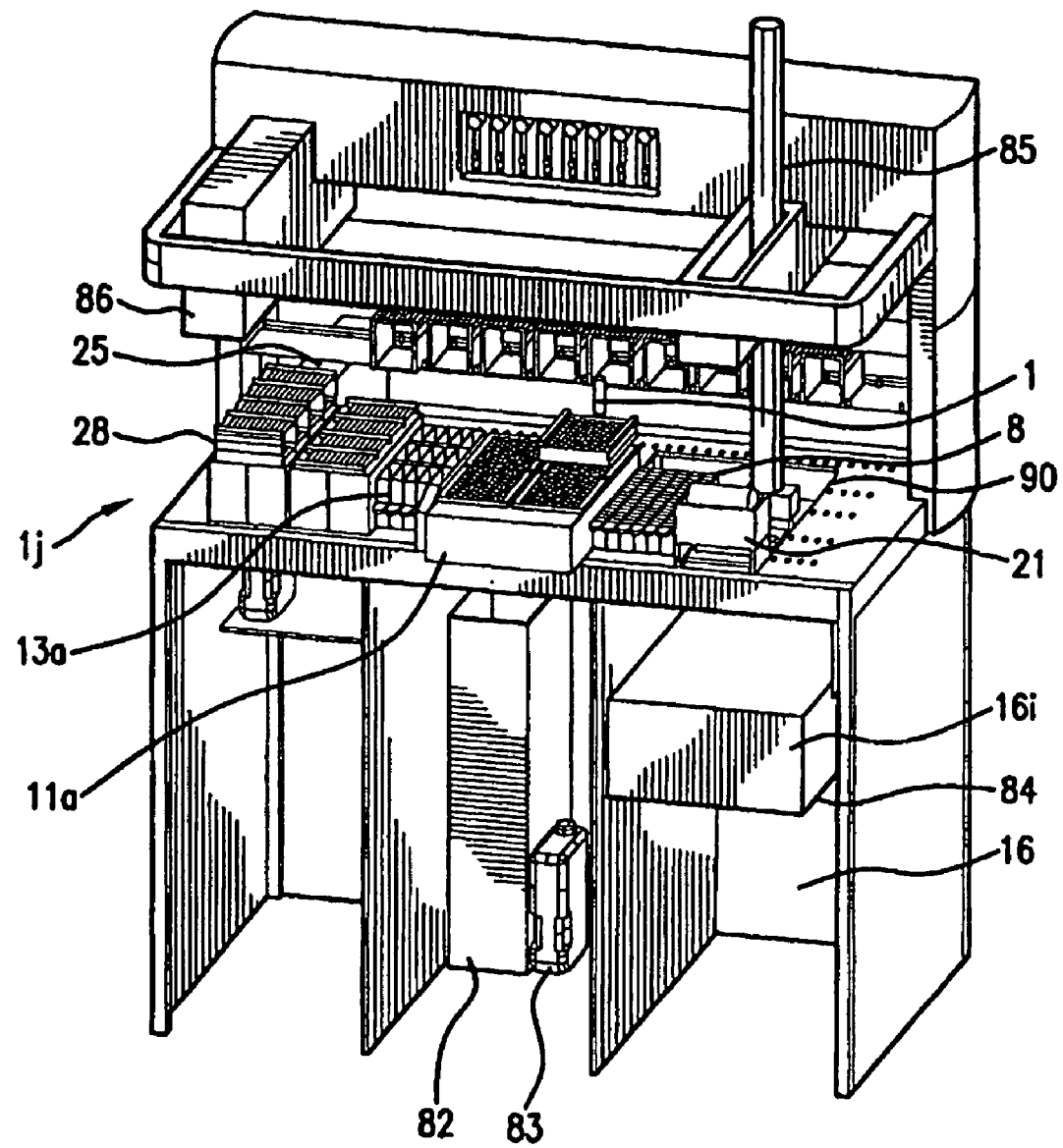
FIG. 34 is a perspective view of still another apparatus substantially similar to the apparatus of FIGS. 3A and 3B described herein.
Figure 34A:
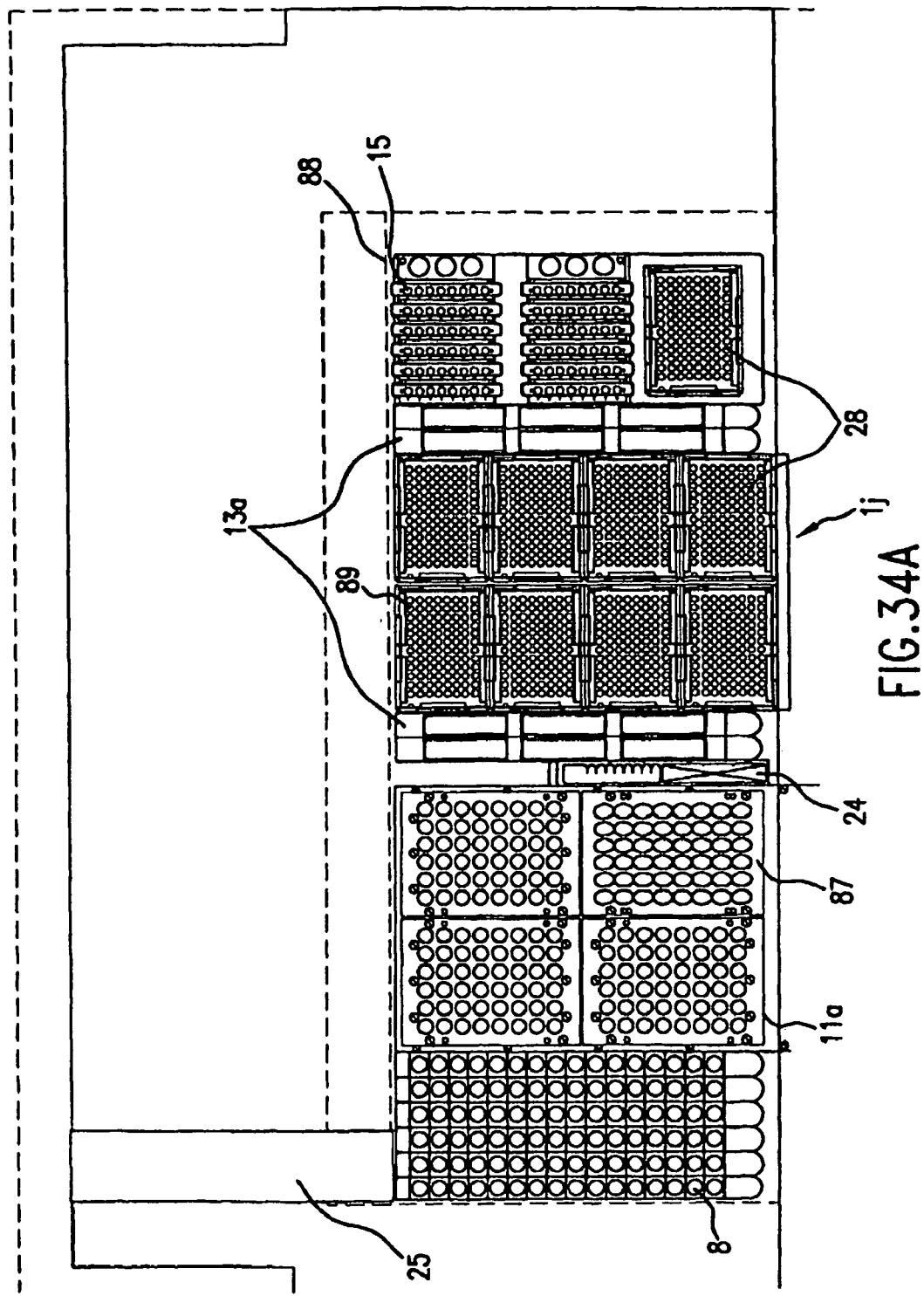
FIG. 34a is a generic top view of the apparatus of FIG. 34.

Additional methods and structures for performing a determination of an item of interest in a sample may be used. FIG. 34 illustrates a fluid handler 86 with other elements configured to process samples from Container 8. The fluid handler 86 utilizes known fluidic transfer technology to automate pipetting steps commonly exercised in routine laboratory applications. Suitable fluid handlers are known and well understood by those skilled in the art, with common commercially available fluid handlers including those manufactured by Gilson, Hamilton, PSS, Tecan, Tri continent, Packard and others. Apparatus 180 is configured with a fluid handler 86, pipette tips 28, reagent handler 13a, DNA/RNA process path extractor 11a, containment for samples contained in container 8, prime mover (drive) 85, sealer 90, amplification and detection device 84, and other required elements to process an item of interest on a single structure or alternately on multiple structures.

Figure 12R:
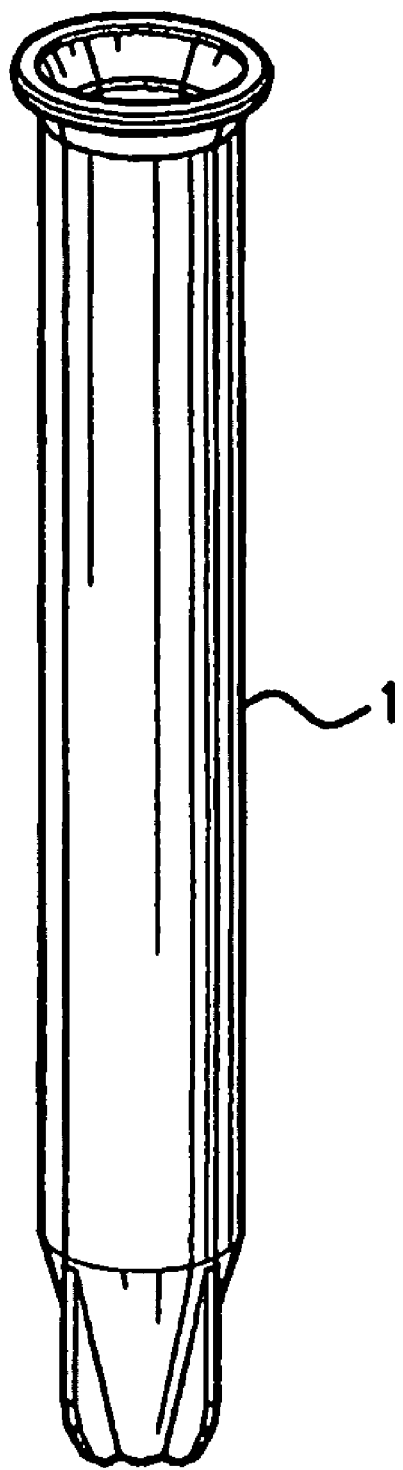
Figure 35:
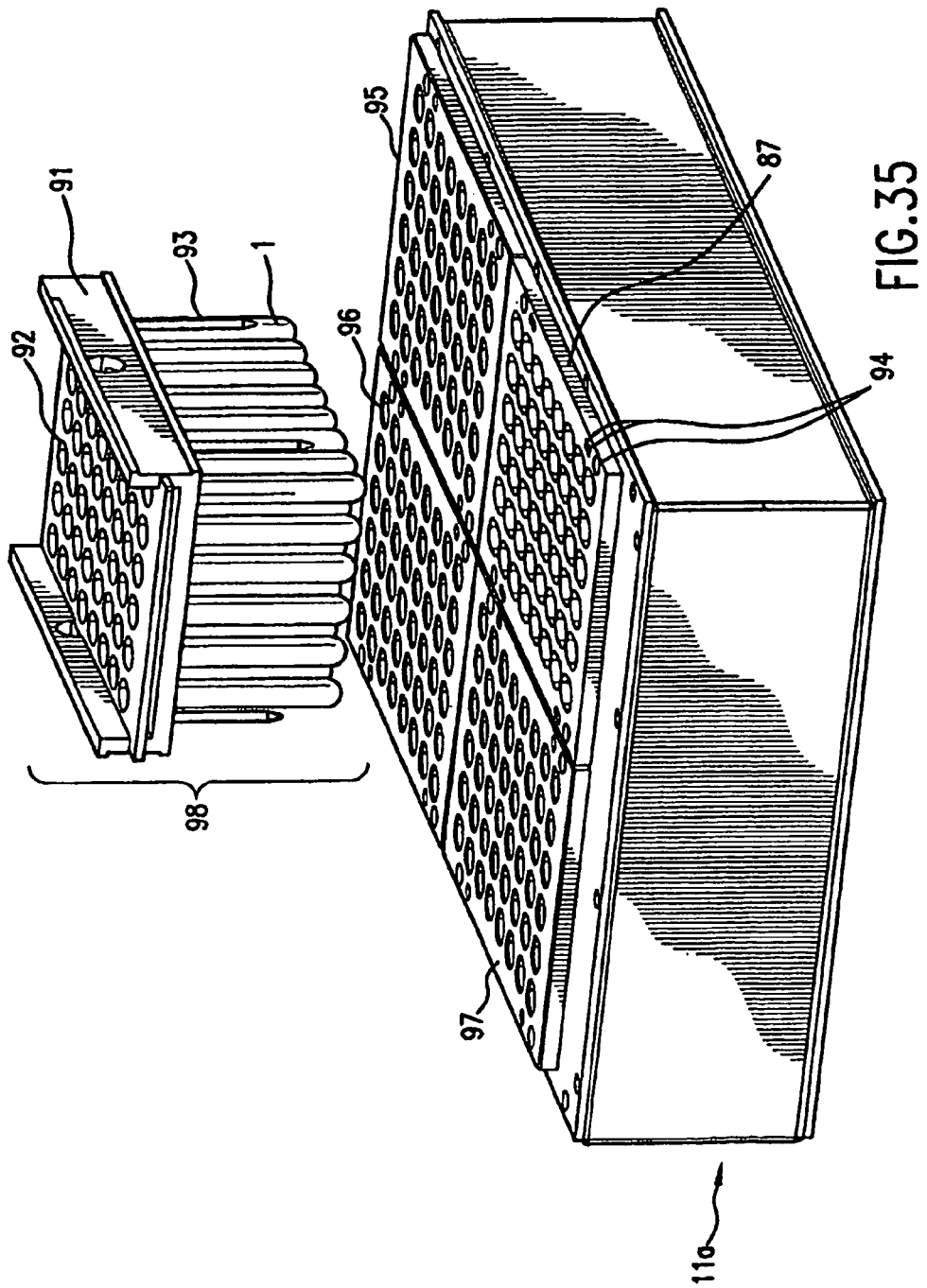
FIG. 35 is a perspective view of an alternate sample prep process area for use with the apparatus of FIG. 34.

To process the aforementioned chemistry examples described herein on apparatus 180, the fluid handler 86 performs the combined functions previously described by pipettors 12 and 19 at the appropriate steps. Automatic pipetting of samples from container(s) 8, and automatic pipetting of reagents useful for separation of an item of interest from reagent area 13a is performed to an array of first container(s) 1. A convenient array of first container(s) 1 is shown in FIG. 35 as reaction vessel container assembly 98, which contains mechanical elements 93 useful for positioning the assembly at various heights onto alternate sample prep process area 11a. The assembly 98 also contains a holder 91 and cover 92 to retain the array of first container(s) 1 during the reaction process. The process area 11a is shown in FIG. 35 and consists of a temperature assembly 96, temperature assembly 95, temperature assembly 97, and magnet assembly 87. Alternate first container(s) 1a-1r are shown in FIGS. 12A through 12R.

Thus, the present invention provides an apparatus for isolating magnetic particles from a fluid, the apparatus comprising: an array of magnets, the array having at least n columns and at least m rows, optionally wherein the poles of the magnets are oriented in parallel, and an array of at least n+1 containers or container-holders that is positioned adjacent to the array of magnets such that each container or container-holder is adjacent to only one pole of a magnet, wherein n is an integer from 1 to 1000, and m is from 1 to 1000. Preferably, n is at least 1 and m is at least 3, such that the array of magnets is at least 1-by-3, and the array of containers is at least six-by-eight. It will be appreciated that more than one magnet can generate a magnetic flux density pattern that is essentially identical to a larger magnet such that each container will be adjacent to only one pole of multiple magnets. Therefore, the present invention also provides an array of magnets and containers (or container holders) wherein each container is positioned adjacent to only one row or column of magnets, wherein a line drawn through the center of each magnet in the row of magnets does not intersect the circumference defining the open end of the container and each magnet adjacent to the container is oriented to have the same pole facing the container.

Figure 44:
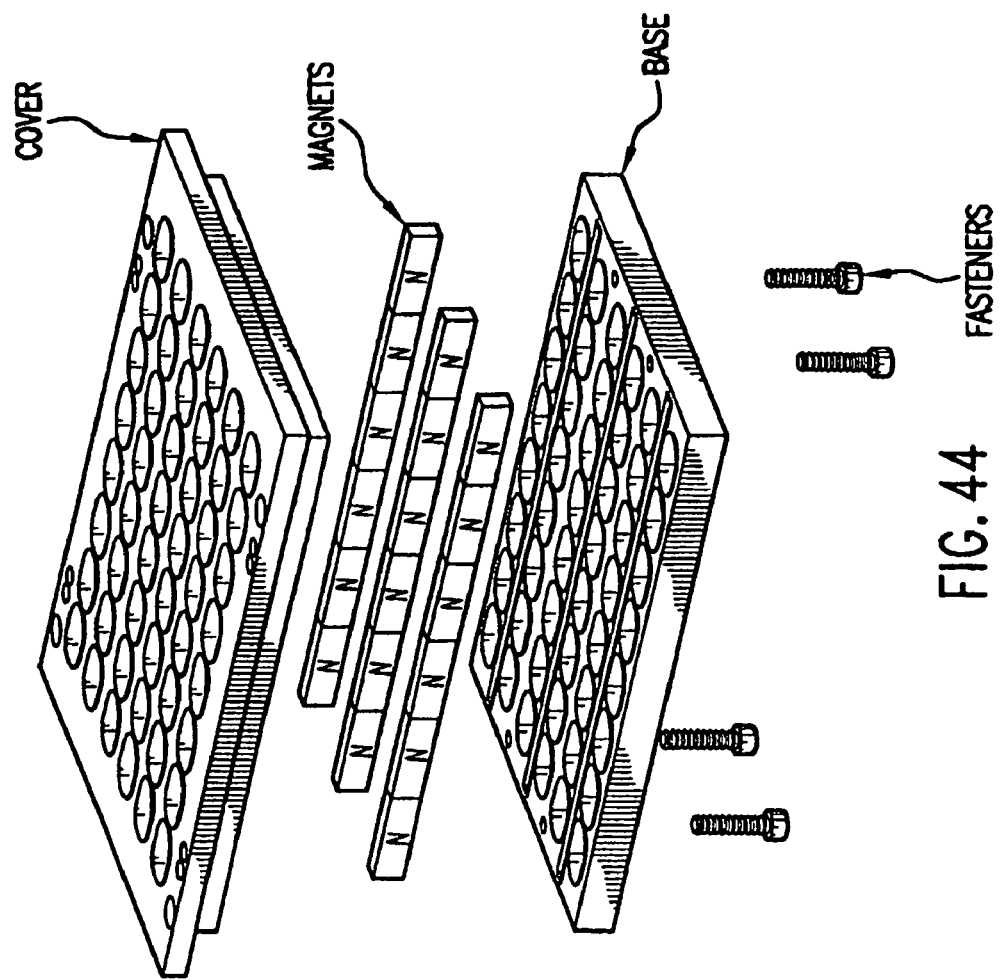
FIG. 44 is an illustration of a magnetic array and tube holder assembly.

Similarly, the array of magnets preferably comprises at least 1 column and at least three rows of magnets. A suitable device having this configuration is depicted in FIG. 44. In FIG. 44 a 3×6 array of magnets is interleaved in a 6×8 array of container holders. The 6 magnets of any column are either abutted end to end, or are placed close together, such that each bank of six magnets produces a magnetic flux pattern that is substantially identical to the magnetic flux a single magnet having a length equal to the six magnets of the bank. Thus, the skilled artisan will appreciate that the six magnets in FIG. 44 can be replace by more or fewer than six magnets.

In the embodiment illustrated in FIG. 44, each magnet in the magnetic array of FIG. 44 has a pair of narrow-sides and a pair of broad-sides, with each pair of sides being oppositely disposed, and the broad sides of the magnets forming the poles of the magnets.

Figure 45:
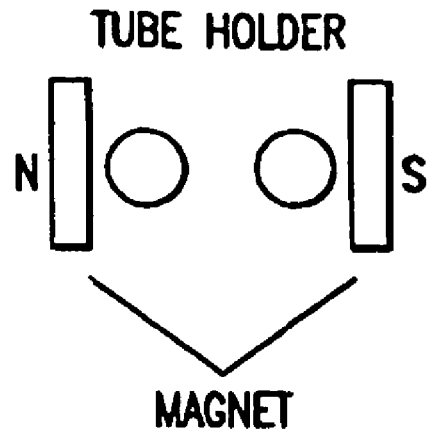
FIG. 45 is an illustration of a pattern of magnets and tube holders.
Figure 46:
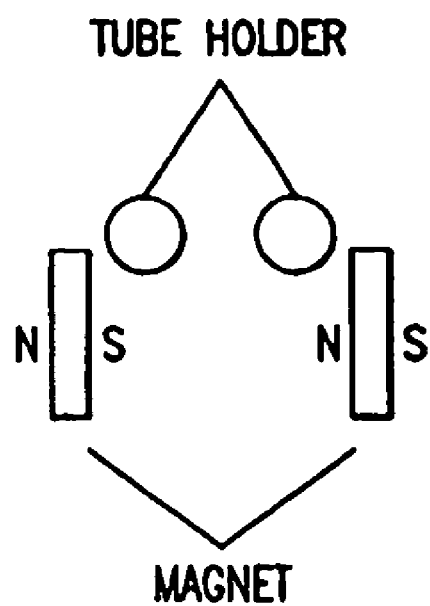
FIG. 46 is an illustration of another pattern of magnets and tube holders.

Thus, the magnetic container holder creates an assembly of magnets and containers having a pattern of containers and magnets generally depicted in FIG. 45, except that the containers, when held by the holders are off-set a small distance as is shown in FIG. 46, and on a larger scale form the pattern shown in FIG. 47, which beneficially generates a sufficient magnetic flux density pattern to capture substantially all the magnetic particles held by containers placed in the container holders, with a minimum requirement for magnets.

Figure 37:
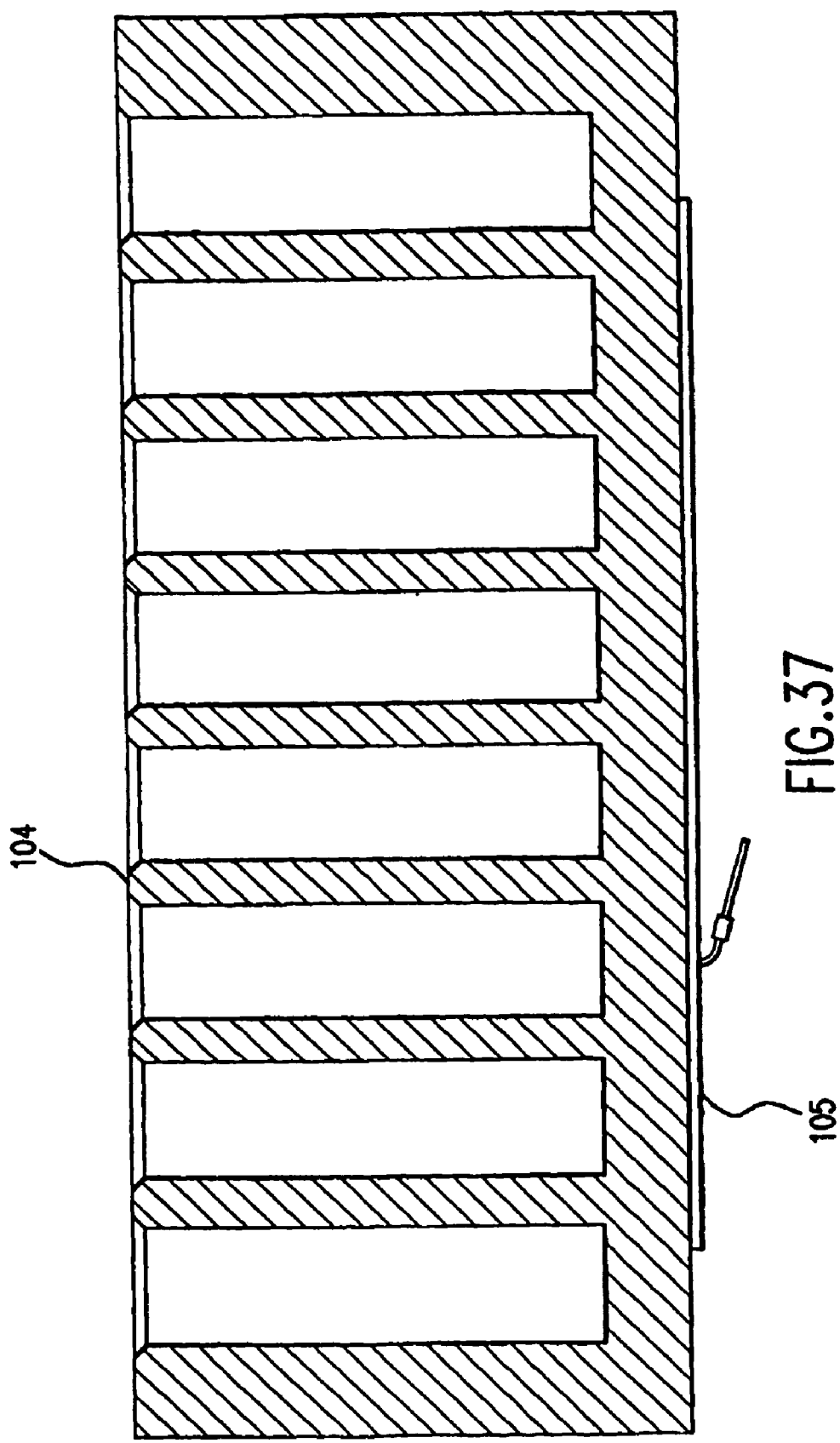
FIG. 37 is a side cross-section view of a component for use with the alternate sample prep process area of FIG. 35.

After sample and reagent pipetting, the assembly 98 is positioned by a suitable robotic prime mover 85 to locations amenable to the chemistry process. Robotic prime movers are well understood in the field and provide automatic gripping and relocation of desired elements in the X, Y, and Z axis. Common manufacturers of such robotic technology include NSK, Yamaha, Fanuc, Tecan, and others. For the process described herein, the assembly 98 is moved to the heater assembly 96 held at a temperature amenable to the separation process. Any suitable time and temperature can be used. In the embodiment shown, one desirable temperature and incubation time has been discovered to be 37 deg C. for 20 minutes. Detail of the assembly 96 is shown in FIG. 37 comprising structure 104 and electronically controlled heater element 105. Upon completion of initial incubation, which could include, without limitation, lysis of a cell, denaturation of a protein, and binding of an item of interest to a solid phase material, the prime mover 85 relocates the assembly 98 to the magnet assembly 87 for separation of the item of interest from other items that are not of interest in a particular embodiment.

To enhance confidence and sensitivity in quantifying an item of interest, processing of a relatively large (e.g., 1 mL-4 mL) sample input volume can be desirable. It is equally desirable to reduce the reagents and reaction volumes for further amplification and detection of samples. Similarly, it is desirable to perform this reduction of volume in a single container. The amount of fluid required for quantification is preferably reduced to a relatively small volume (e.g., preferably to less than 500 µL, more preferably to less than 100 µL, optionally to less than 50 µL, and in some embodiments to less than 25 µL, but preferably is at least 2 µL) from relatively large reaction volumes (e.g., preferably greater than 1 mL, more preferably greater than 2.5 mL, optionally greater than 5 mL, or 10 mL, but also preferably not more than 25 mL or 100 mL). However, when utilizing a solid phase in solution during the reaction for binding item of interest, for example microparticles, it has not been possible with prior art methods to first disperse particles in a large volume (e.g., 3.5 mL), separate the particles, and ensure high capturing of particles for subsequent steps completed at relatively low volumes (e.g., 80 µL) in a timely fashion, especially without centrifugation, at least on an automated instrument.

Figure 35A:
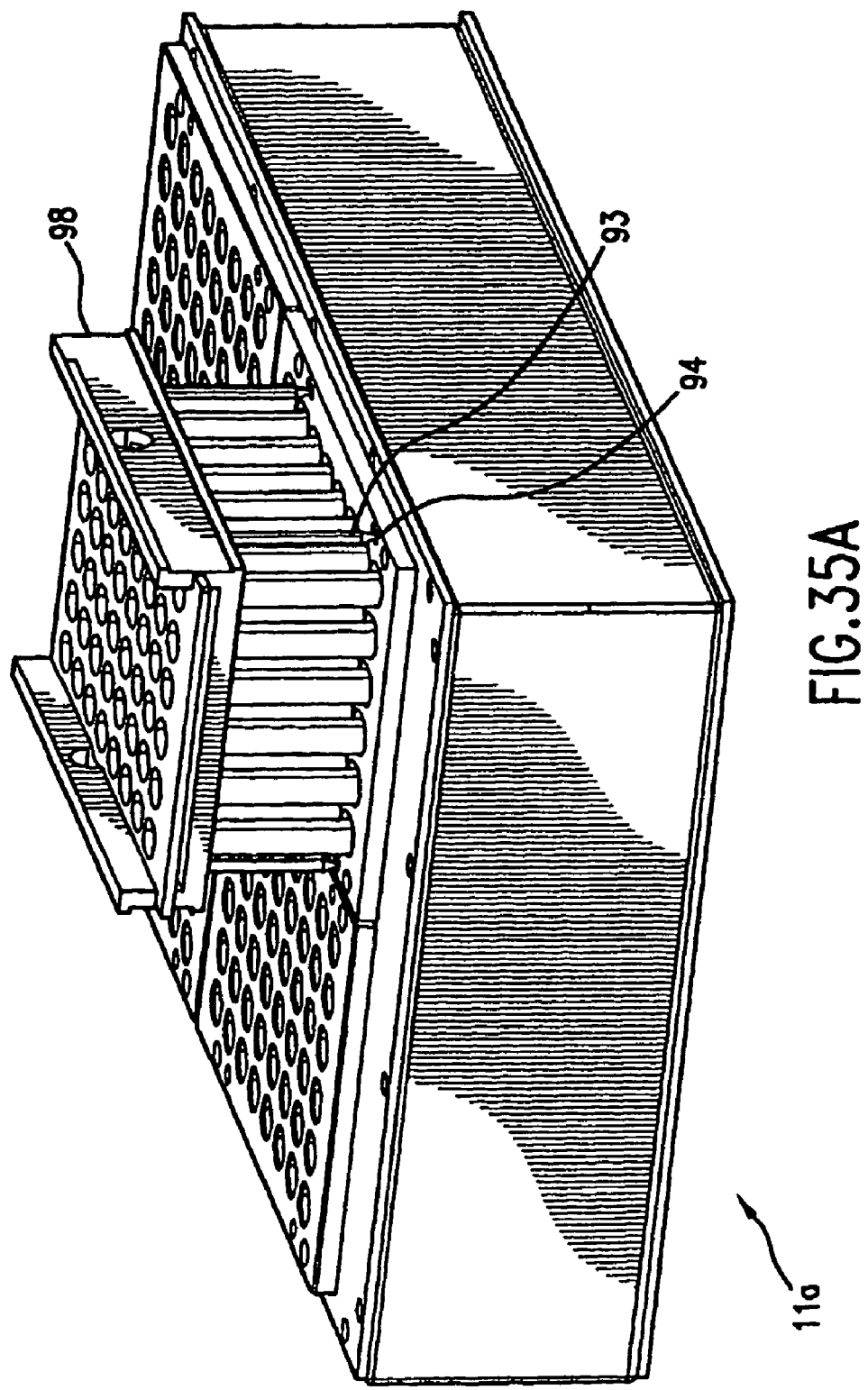
FIGS. 35A through 35F are additional perspective views of the alternate sample prep process area of FIG. 35.
Figure 35B:
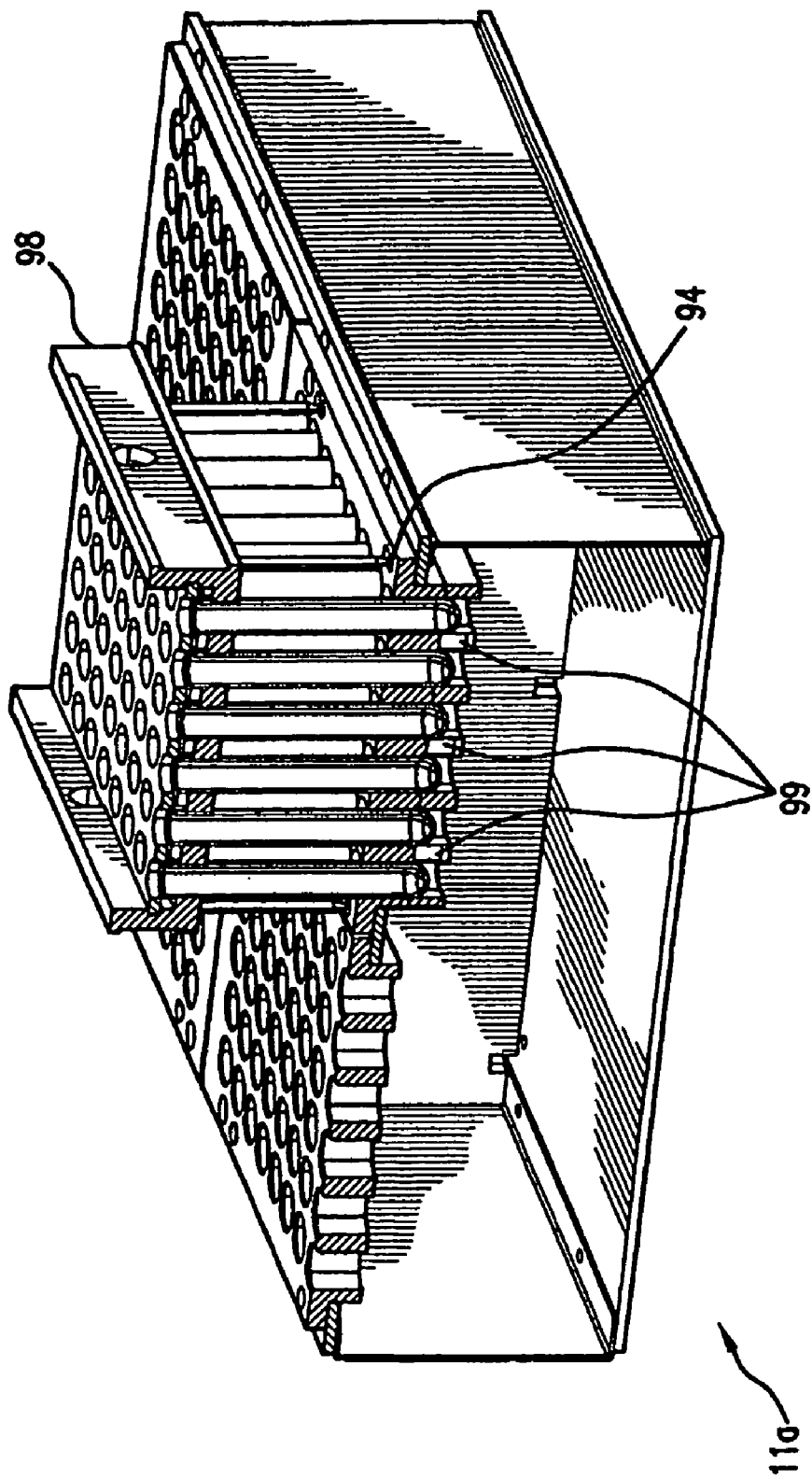
Figure 35C:
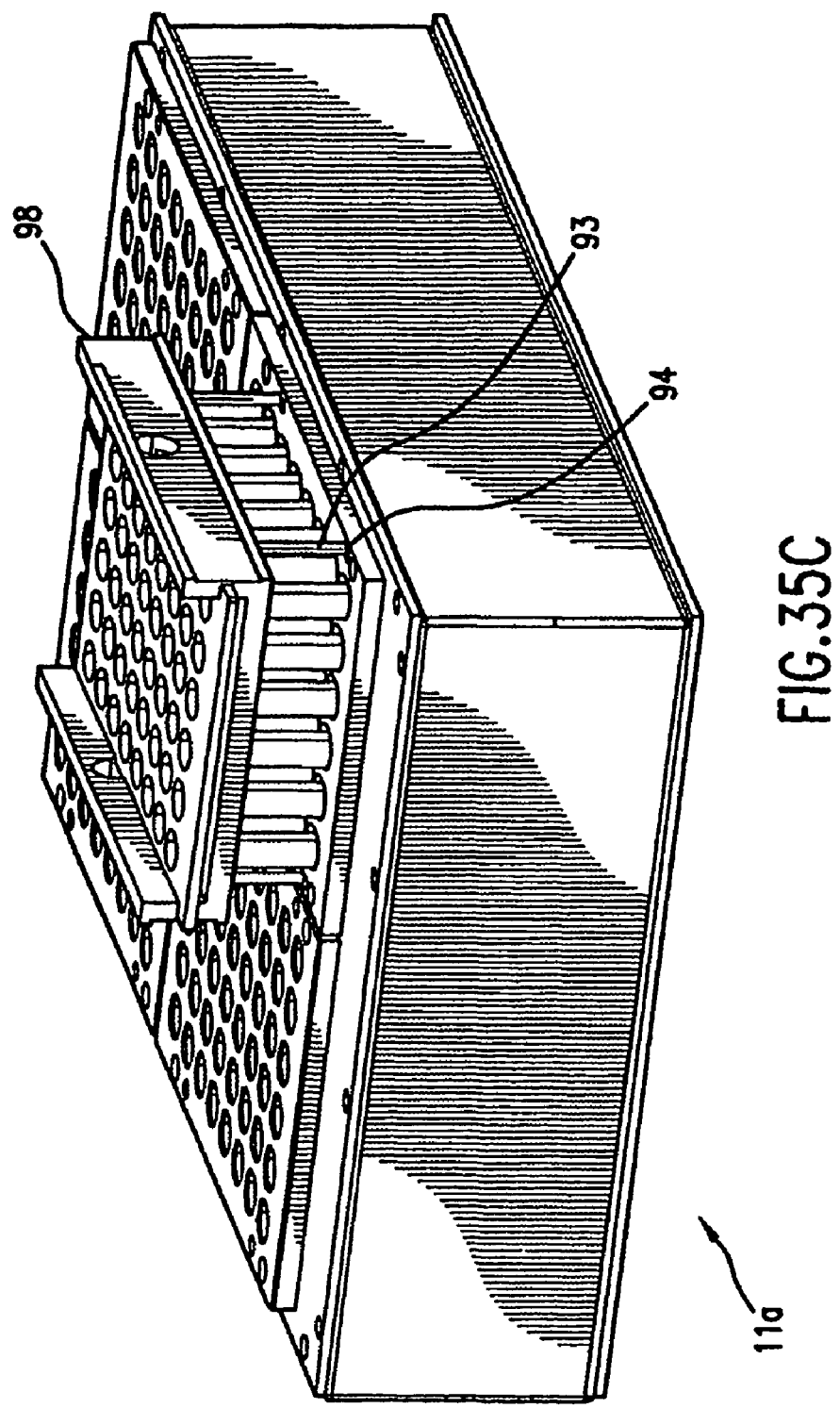
Figure 35D:
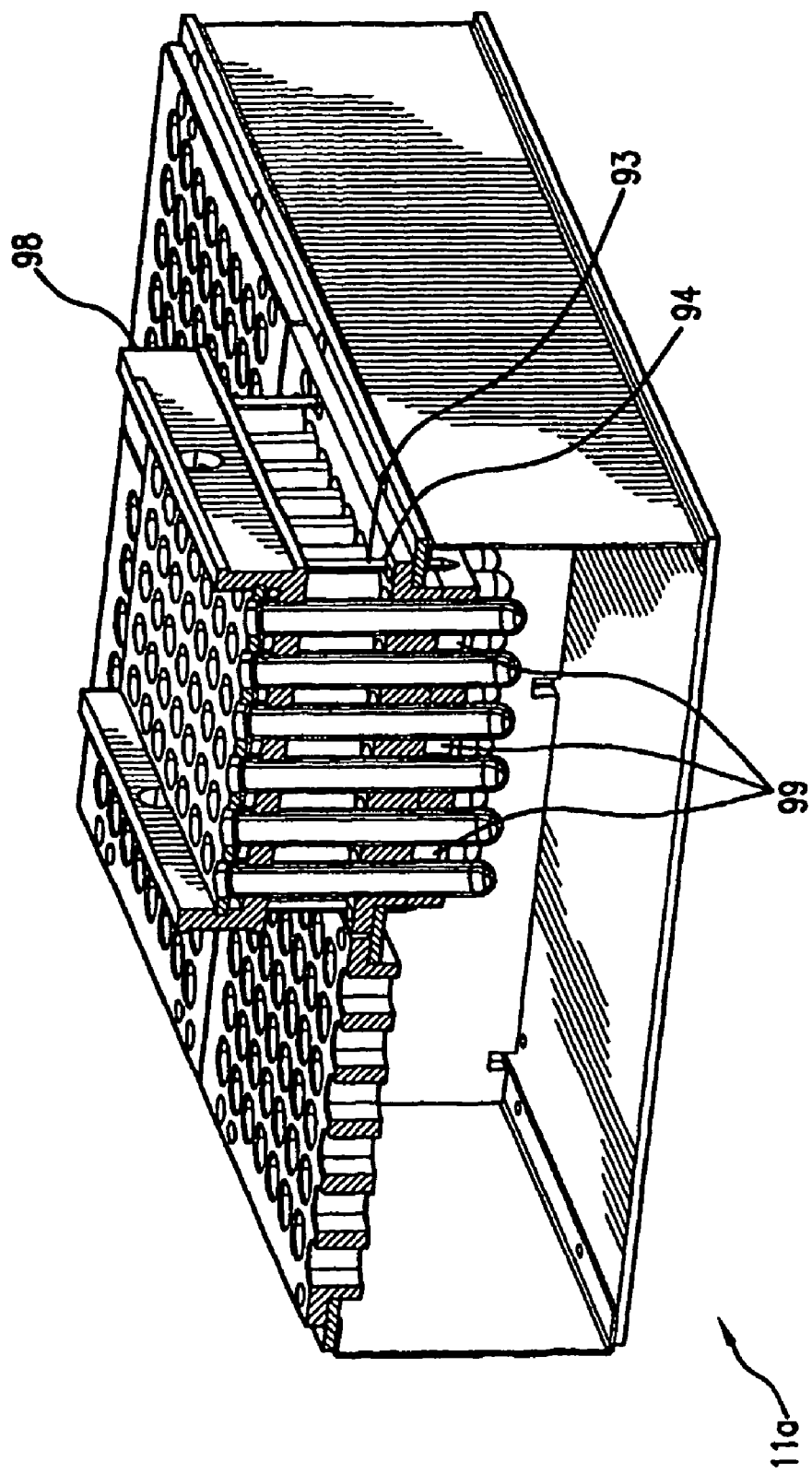
Figure 35E:
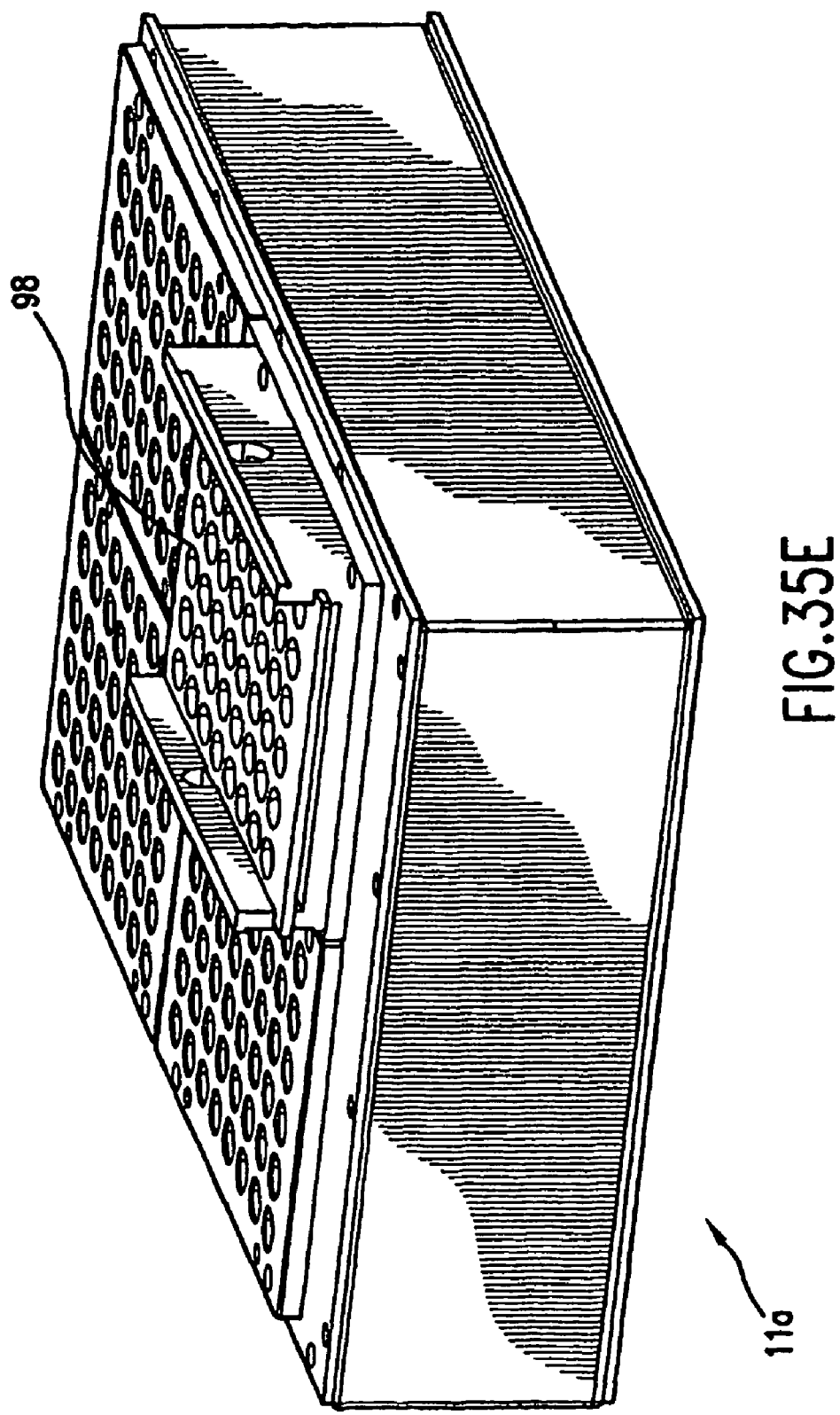
Figure 35F:
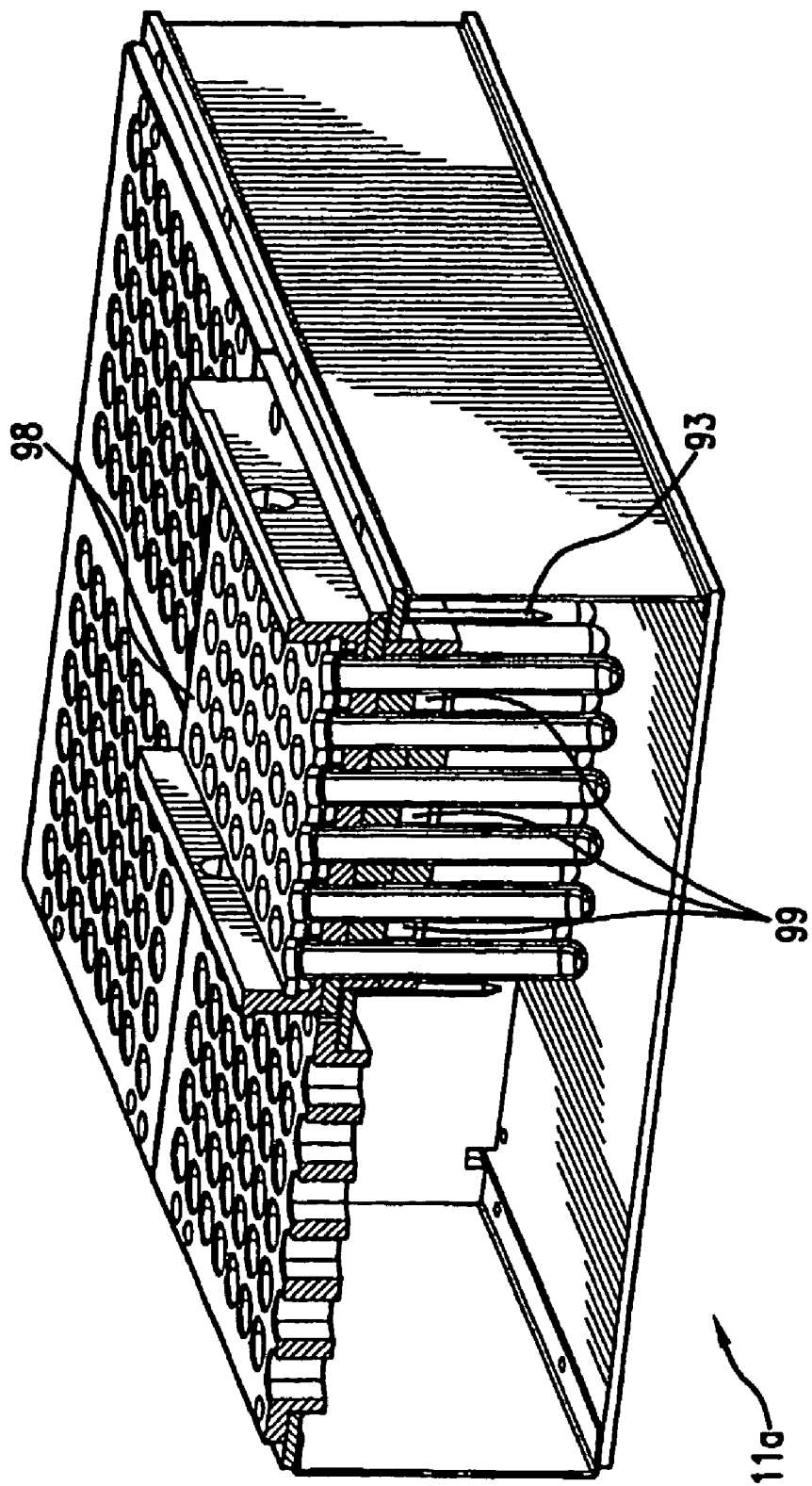

In the depicted embodiment, the present invention first positions the assembly 98 to a first position on the magnet assembly 87 with the prime mover 85 as shown in FIGS. 35E and 35F. Magnets 99 are positioned relatively high to the first container reaction volume for capture of bound item of interest in a region relatively high on the side wall of the first container(s). In this embodiment, magnets with horizontal poles in every other row of the array are shown which provides for optimal capture performance, although other suitable magnet configurations could be utilized. After a period of time (e.g., 15 to 210 seconds, preferably 45 to 135 seconds), the prime mover 85 (or an alternative means of motion) moves the assembly 98 to a second position on the magnet assembly 87 as shown in FIGS. 35C and 35D. During this process, already captured particles are moved down vertically on the first container 1 wall as a consequence to the movement, and uncaptured particles (if any) in the middle region of container(s) 1 are additionally captured. After a suitable period of time (e.g., 15 to 210, or 45 to 135 seconds) to allow capture of the magnetic particles by the magnet 99, the assembly 98 is preferably moved to a third position on the magnet assembly 87 with the prime mover 85 as shown in FIGS. 35A and 35B. During this process, already captured particles are moved down vertically on the container(s) wall as a consequence to the movement, and uncaptured particles in the lower region of container(s) 1 are additionally captured to a desirable and relatively low position on container(s) wall. After each sequential capture, it may be desirable to use the fluid handler 86 to sequentially aspirate and dispose of unbound reaction mixtures, or alternately, perform evacuation of unbound reaction mixture after the final capture stage.

In another embodiment, a sample is combined with magnetic particles and lysis solution in a container and held under lysis conditions for a period sufficient to lyse the sources of nucleic acids in the sample to produce a lysed sample and allow capture of the nucleic acids on the magnetic particles. The magnetic particles can be captured and the uncaptured portion of the lysed sample can then be aspirated from the container. According to the preceding description, the magnets are disposed relatively high on the wall of the container and after a suitable period of time are moved relative to the container such that the magnet is disposed beside the container near the bottom of the container. This has the effect of isolating the pellet of magnetic particles on the side of the container near the bottom of the container, making evacuation of the lysis solution from the container more effective and/or reducing the extent of magnetic particle loss during the aspiration or evacuation of the lysis solution. This is illustrated in FIG. 48.

If desired, wash solution can be added and the magnets can be manipulated to capture the magnetic pellet in the position shown in FIG. 48.

Figure 49:
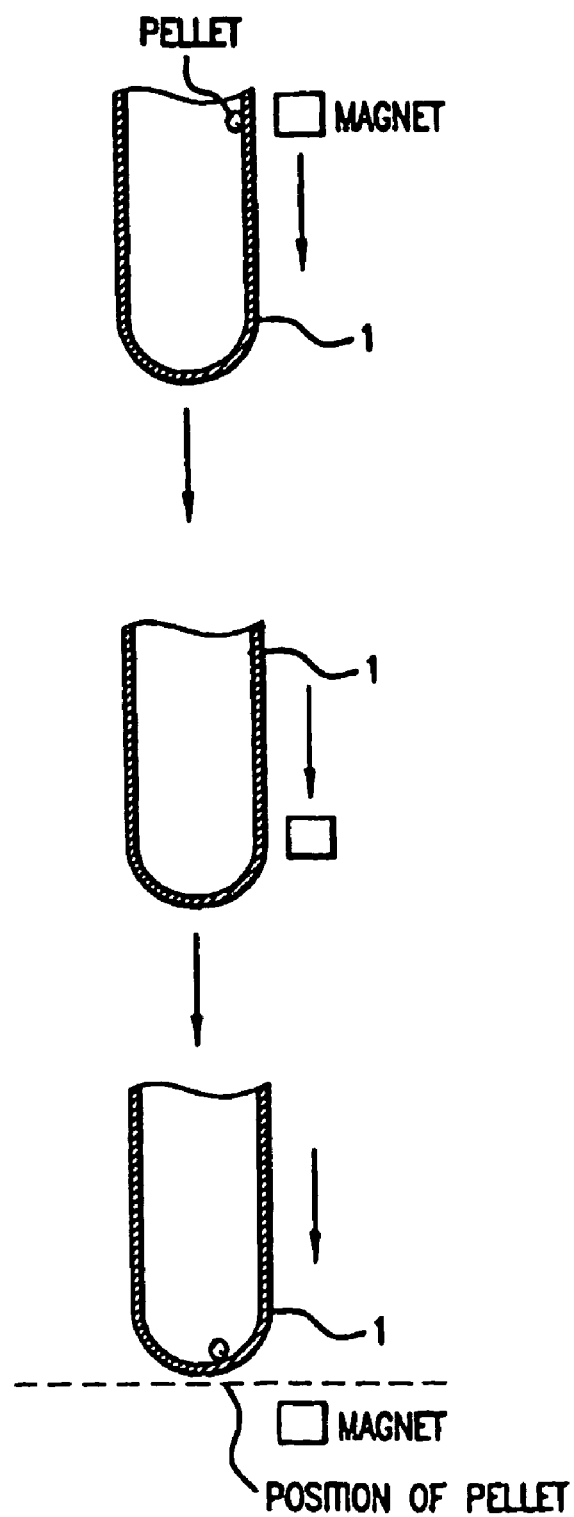
FIG. 49 illustrates preferred relative movement of the container 1 and the magnet(s) for elution of nucleic acids from magnetic particles.

After the one or more washing steps described above are completed, the container can be lifted relative to the magnets such that the bottom of the container is raised above the top of the magnet. This causes the pellet to move to the bottom of the container, which is the preferred position for the pellet to reside in when the nucleic acids are to be eluted from the magnetic particles. To accomplish the elution, a small volume of elution solution is added to the container. Any suitable volume of elution solution can be used, and typically at least 10 µl, preferably at least 30 µl, are added to the container. However, it is desirable that the elution solution not be too large. Accordingly, the maximum volume of elution solution is preferably less than 510 µl, more preferably less than 210 µl, and yet more preferably less than 100 µl. The use of such low elution solution volumes (e.g., 40 µl) means that it is better if the magnetic particle can be reliable moved to the bottom of the container. This is accomplished in the present embodiment by lifting the bottom of the container above the top of the magnet as is illustrated in FIG. 49.

The relative movement of the magnet position to the container can be achieved by any suitable means. For example, a robotic prime mover 85 can move the arrayed containers from one location to another wherein structural supports dispose the arrayed containers at different heights relative to a (partial) array of magnets, as is illustrated. In another embodiment, a mechanism can suitably shift the location of the arrayed containers relative to the magnets, for example by means of a lifting arm or arms, or by rotating the combined container and magnet arrays wherein either the container array or the magnet array travels across an inclined plane. This advantageously causes the position of the container relative to the magnet to change in a continuous fashion. The ordinarily skilled artisan will readily appreciated that other suitable means for changing the positions of the container to the magnet can be employed.

Thus, the present invention also provides a method for separating magnetic particles suspended in a fluid comprising providing an apparatus in a first position having a container for containing a fluid having magnetic particles suspended in the fluid, an automated pipette, and a magnet, wherein, if necessary, magnet or the container or both the magnet and the container are moved such that the magnet exerts a magnetic field on the magnetic particles that tends to isolate the magnetic particles in a preselected zone of the container, applying the magnetic field across the container (for a suitable period of time) such that the magnetic particles are evacuated from a first aspiration zone of the container, wherein the preselected zone is distal from the pipette. The method continues, if necessary, by submerging the pipette into the fluid and aspirating a preselected quantity of fluid from the first aspiration zone in the container, preferably wherein the preselected quantity of fluid is less than ½ (one-half) the volume of the fluid (e.g., 5%-50%), and alternatively wherein the preselected quantity of fluid is about 85% of the volume of the fluid (e.g., more than about 50% to about 90%). Optionally, the method also includes moving the apparatus to a second position thereby separating the magnetic field from the pipette. In this second position, the magnet can apply a magnetic field to the magnetic particles and evacuate the magnetic particles from a second aspiration zone. The automated pipette is then advanced and the fluid is aspirated from the second aspiration zone, thereby separating the magnetic particles from the fluid.

The assembly 98 is then moved to a temperature position 97, preferably where no magnets are present. The fluid handler 86 adds a wash fluid, and the assembly 98 is then moved back to the magnet assembly 87 for additional capture and aspiration to waste of unbound reaction mixer. The wash and capture process is repeated a number of times. For the some embodiments, three to four wash cycles are preferred.

After washing, the fluid handler 86 can dispense an elution buffer and the prime mover 85 can move the assembly 98 to the temperature assembly 95 where during incubation (e.g., 70 deg C. for 20 minutes) the item of interest is separated from solid phase media. A final capture of unbound solid phase is performed in the magnet assembly 87 prior to further processing. Further processing may contain the steps of transferring an item of interest from the first container(s) 1 to an alternate container(s) 15. The container(s) 15 may also contain additional reagents dispensed by the fluid handler 86. The container(s) 15 can be sealed with a sealer 21 and further transferred by the prime mover 85 through an opening 90 to an additional process path 16 containing one or more process paths 16i located vertically below the alternate sample prep processing area 11a as illustrated in FIG. 34. In this embodiment, positioning the process path 16 vertically lower than the alternate sample prep processing area 11a improves separation of sample preparation processes from the amplification processes, thereby reducing chance of contamination on a single structure. Further utilizing a vent 45 in the wall of the structure containing the amplification detection process (in location 84 shown on FIG. 34) further removes any undesirable airborne contaminates from the vicinity of the amplification and detection processes thereby reducing the chance of contamination between processing areas.

Figure 38:
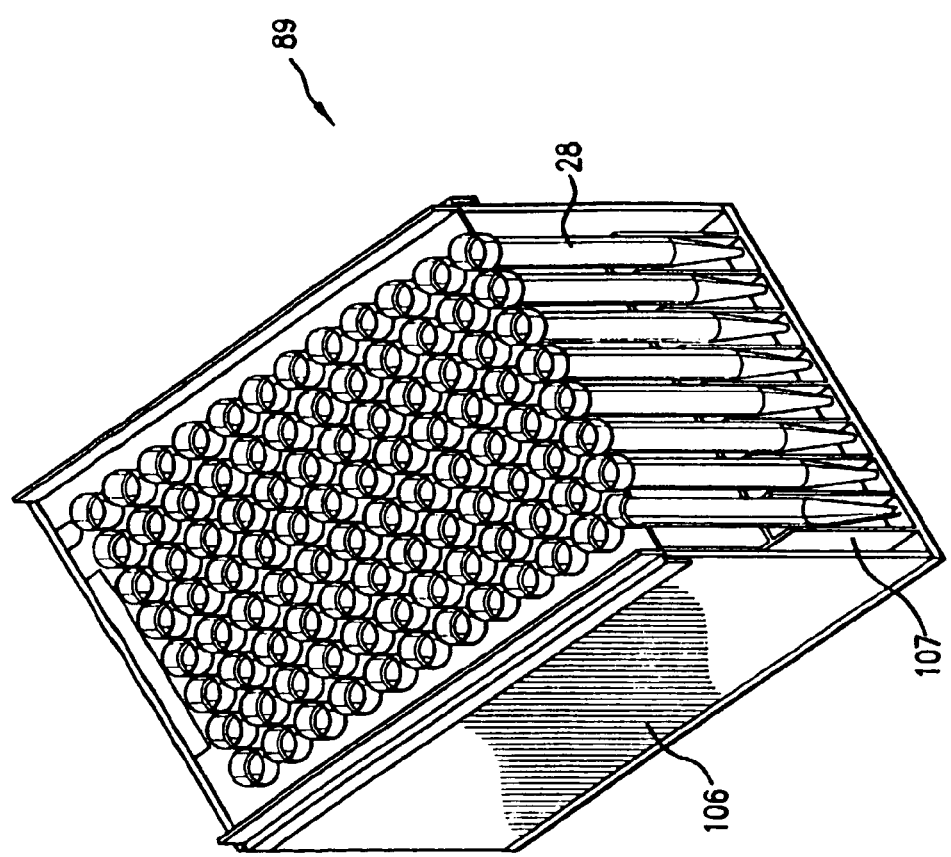
FIG. 38 is a perspective view of a tip isolation containment assembly for use with the apparatus of FIG. 34.

To aid in the reduction of solid waste, the fluid handler 86 utilizing disposable pipette tips 28 may reserve tip(s) 28 for use with a specific or particular sample during the chemistry process to be used on multiple occasions. To properly house such tip(s) 28 during appropriate times in the process to be re-used later in the process, a tip isolation container 107 interfaces with tip isolation container holder 106 as shown in FIG. 38. This causes each tip in an array of tips to be stored and isolated from other tips until they are needed. The skilled artisan will appreciate that substantial reductions in solid waste generation can result from the use of this pipette parking mechanism and assembly.

It is understood other processes may be combined with the described processes to created additional processes. For example, an item of interest could remain in the container(s) 1 for further reagent addition and amplification detection with the alternate sample prep processing area 11a. Also, two or more assemblies 98 may be processed sequentially, in parallel, or interleaved to improve sample processing yield. In addition, the magnet(s) 99 may be attached to a mechanism to provide relative positioning of the magnet(s) 99 to the container(s) 1.

Figure 42:
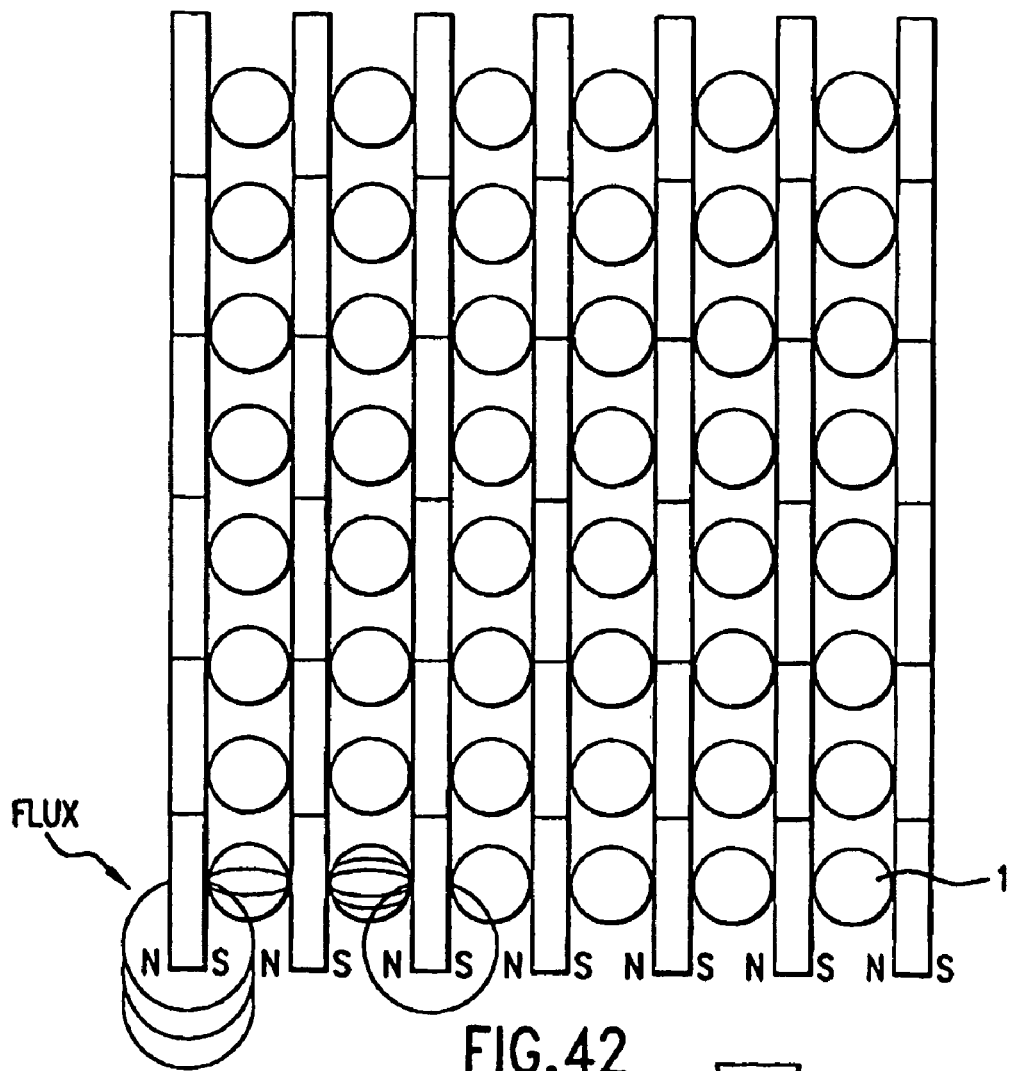
FIG. 42 is an illustration of a magnetic pattern.
Figure 42A:
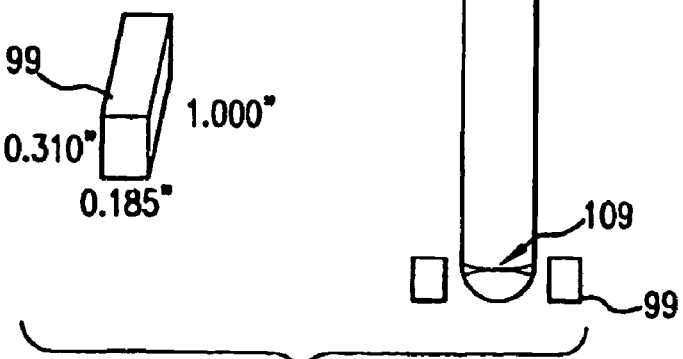
FIG. 42A is another illustration of another magnetic pattern.
Figure 42B:
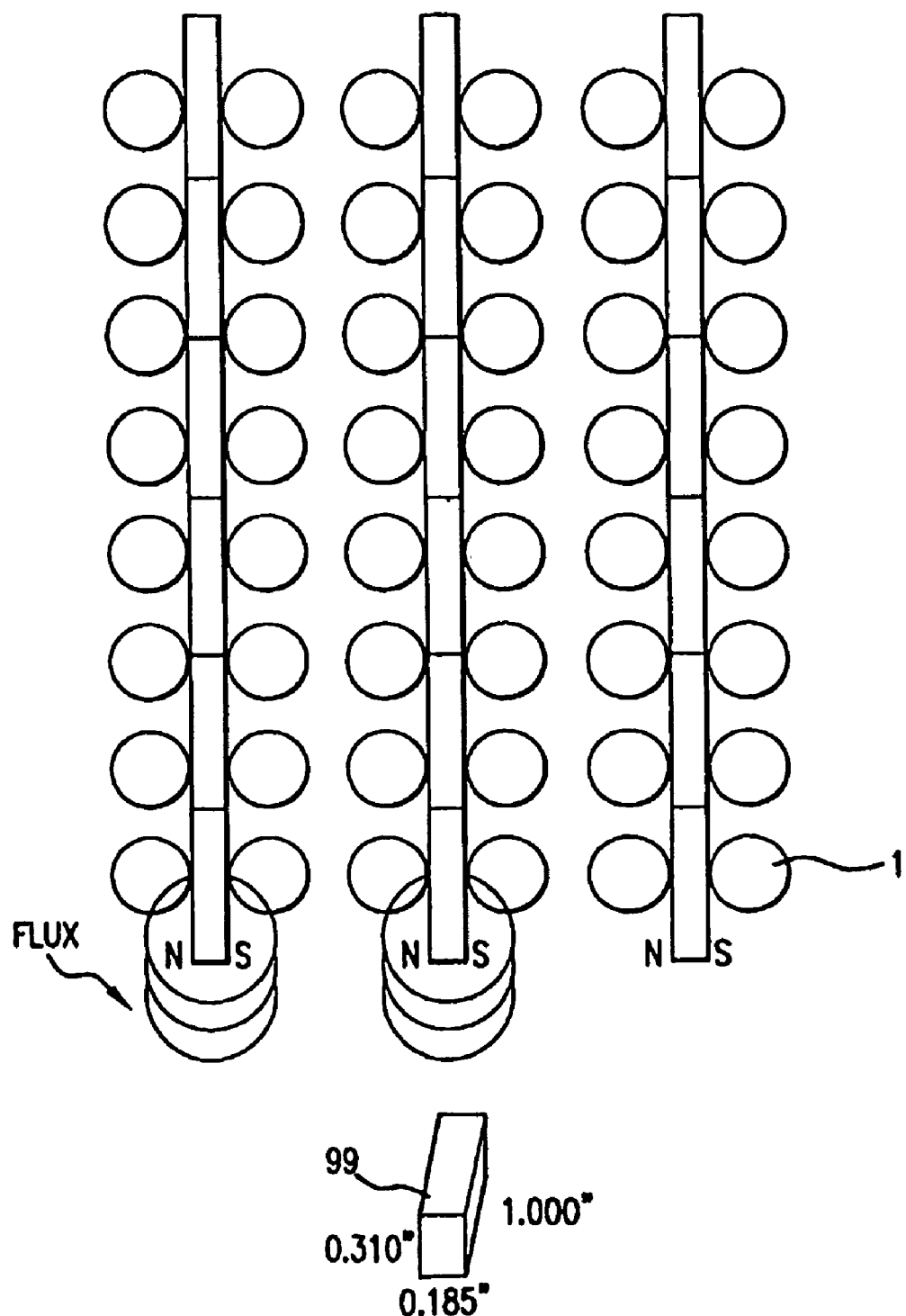
FIG. 42B is another illustration of yet another magnetic pattern.
Figure 43:
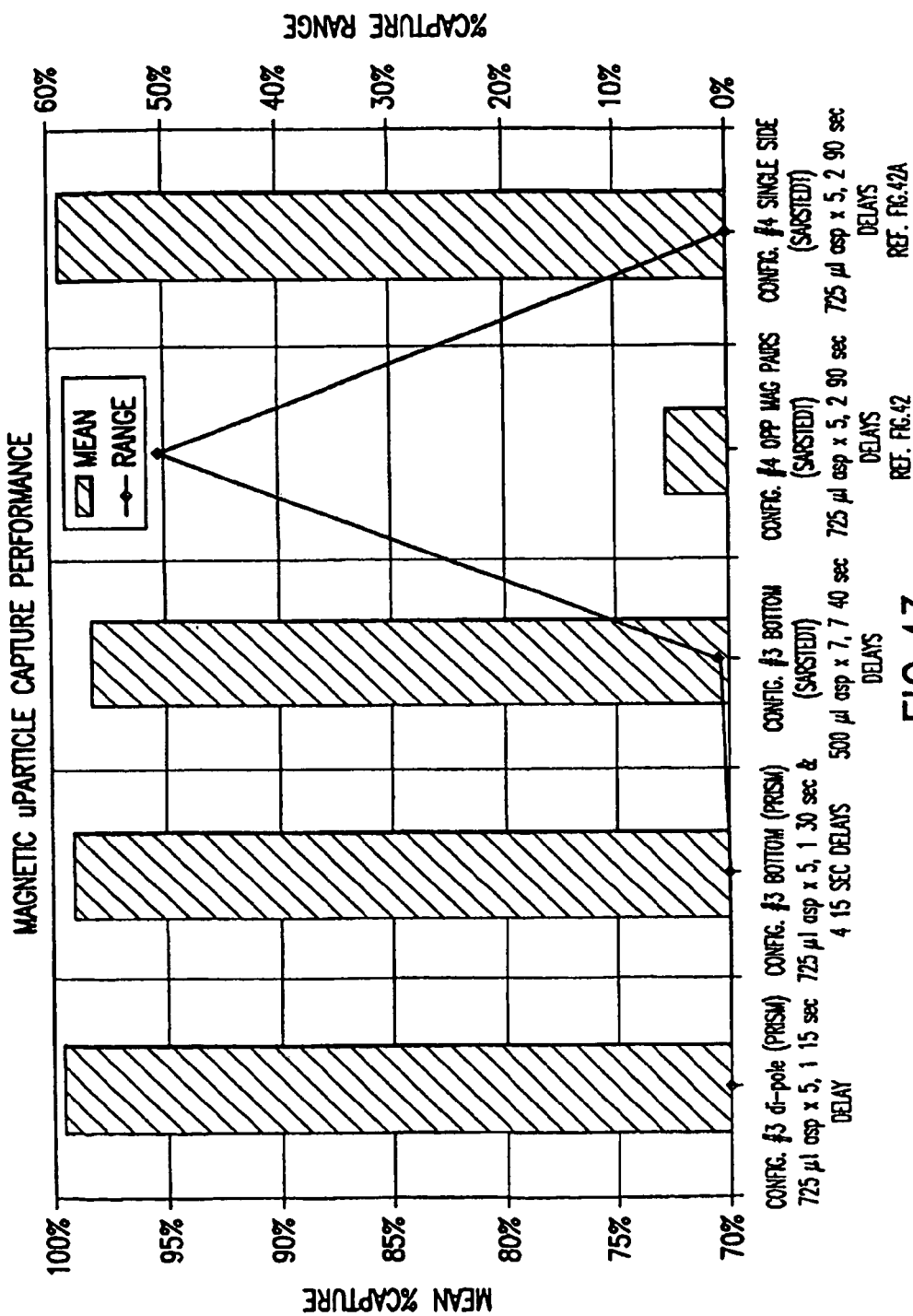
FIG. 43 is an illustration of performance data using multiple magnetic configurations.

Detail of the magnet assembly 87 is shown in FIGS. 36 and 36A. The magnet(s) 99 reside in slot(s) 103 and are mechanically retained with a plate 100 and fasteners 102. The polarity of the magnets shown in FIG. 36A is horizontal, however, alternative configurations (including without limitation diagonal and vertical configurations) can also be applied. Alternating rows of magnets have are superior to utilizing every row possible and adjacent to the container(s) 1. While the present invention is not bound by any particular theory in this regard, this superiority may be because undesirable magnetic flux density patterns surprisingly develop when utilizing every row possible as illustrated in FIGS. 42 and 42A, (resulting in a solid phase bridge 109). Desirable flux density patterns are illustrated in FIG. 42B and a comparison of % Capture performance between the configurations is illustrated in FIG. 43.

Figure 40A:
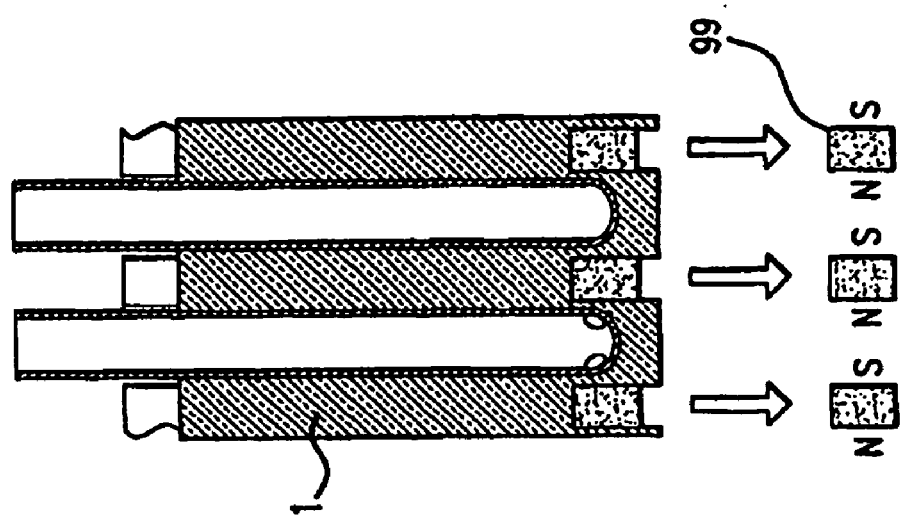
FIGS. 40A and 40B are side views of other alternate magnet configurations for use with the alternate sample prep process area of FIG. 35.
Figure 40B:
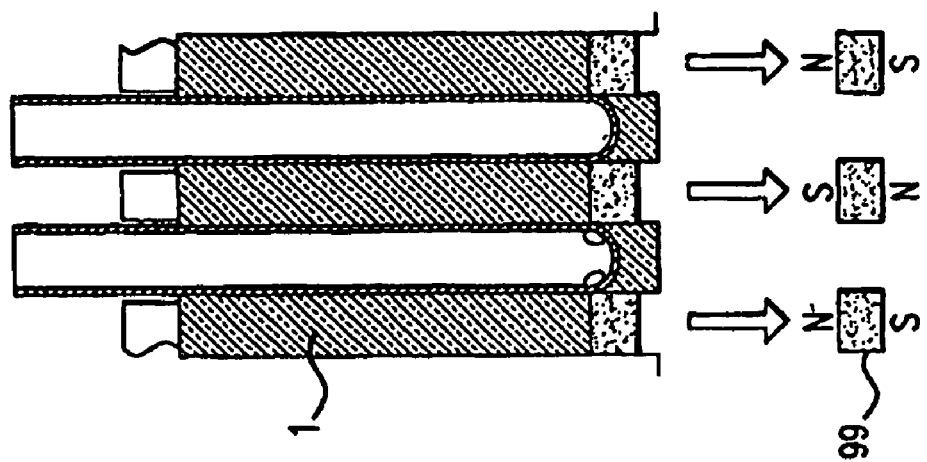
Figure 40C:
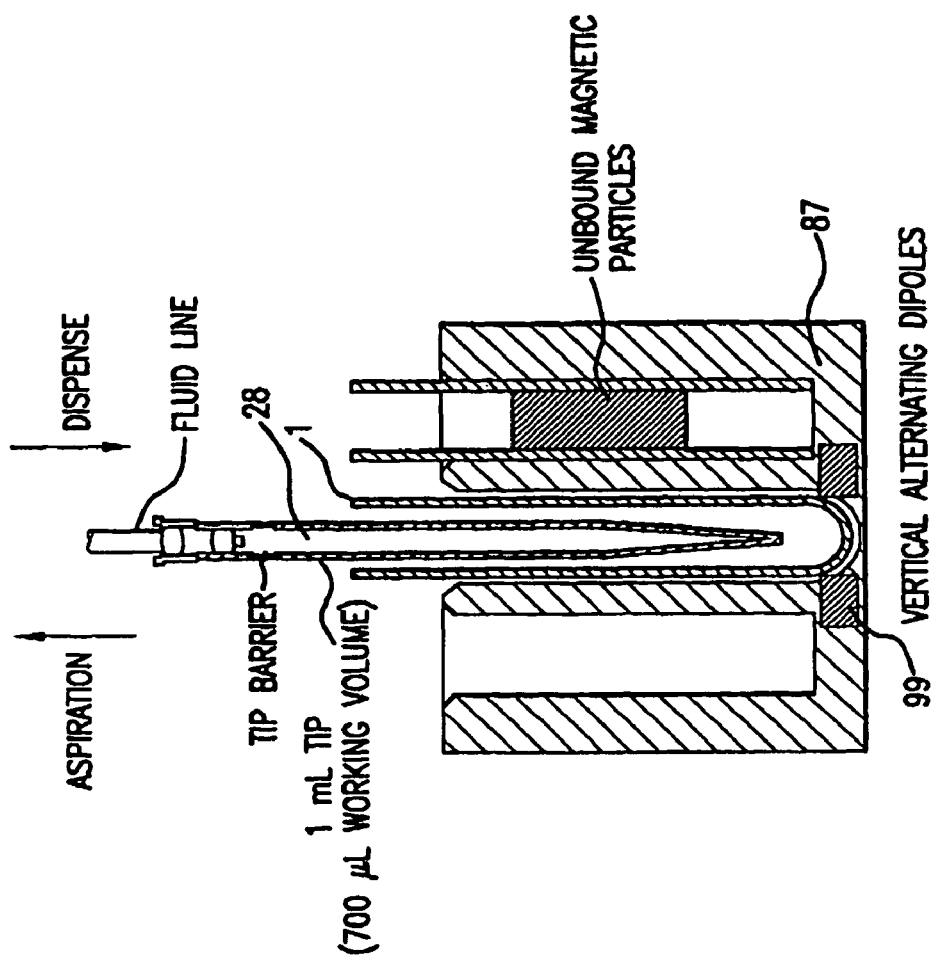
FIG. 40C is a side views of a pipettor interfacing with alternate magnet configurations shown in FIGS. 40A and 40B.

Additional alternate configurations could be integrated into the magnet assembly 87. Fixing the position of the magnet(s) 99 and container(s) 1 during the aforementioned process could yield acceptable results with increased capture time allowing for magnetic particles to settle to lower portions of the tube resident to a stationary flux pattern as shown in FIG. 40B. To enhance the reach of the flux pattern in a vertical plane, the magnet(s) 99 may be positioned with vertical pole orientation as illustrated in FIG. 40A, thereby reducing capture time required. To further reduce capture time in a fixed magnet configuration, the pipette tip 28 may be moved to a region within the magnetic flux pattern during evacuation of unbound reaction mixture as illustrated in FIG. 40C. Such technique reduces the amount of unbound magnetic that may be inadvertently diverted to waste.

Figure 39:
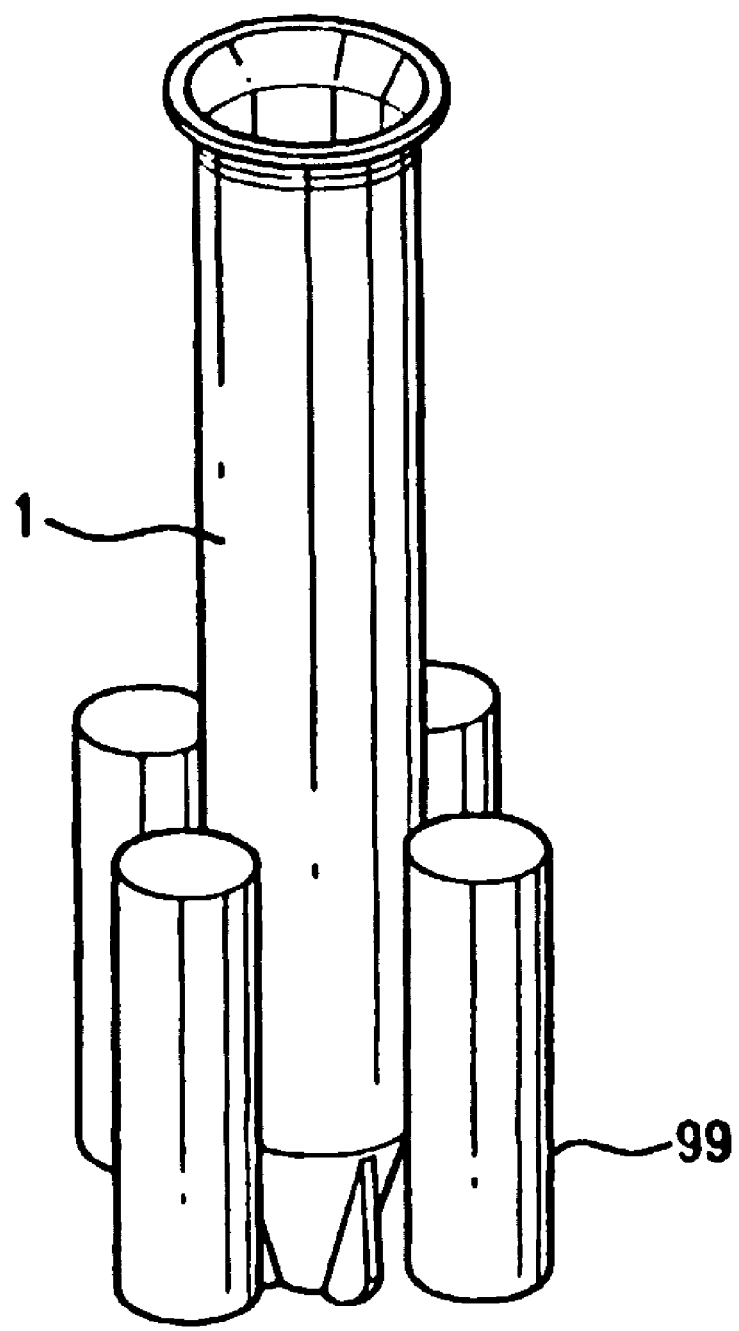
FIG. 39 is a perspective view of an alternate magnet configuration for use with the alternate sample prep process area of FIG. 35.
Figure 40D:
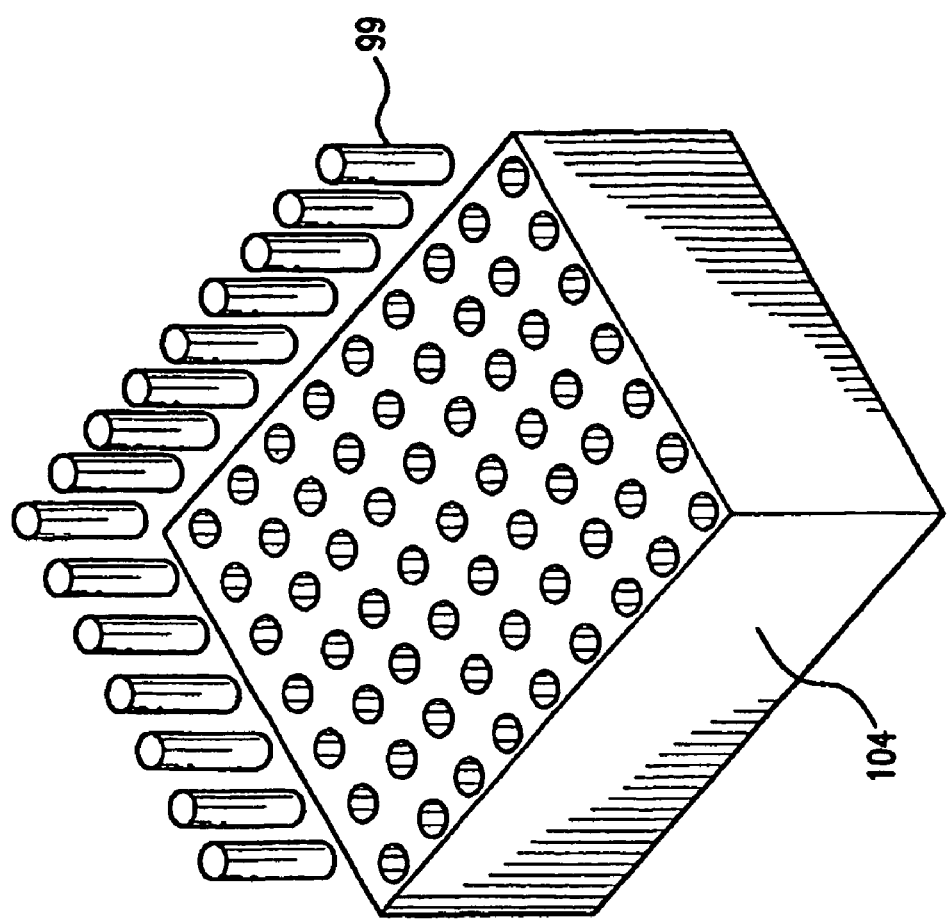
FIG. 40D is a perspective view of an alternative magnet assembly for use with the alternate sample prep process area of FIG. 35.

In another embodiment, cylindrical magnets may be used in the magnet assembly 87. Advantageously, cylindrical magnets have a north pole along one edge of the cylinder and a south pole along the opposite edge. As illustrated in FIG. 39, cylindrical magnet(s) 99 may be oriented around the container(s) 1 to achieve effective capture of magnetic microparticles. Multiple options are available for configuring the array of magnets around the array of containers 1. For example, each container 1 in the array of containers can be placed next to four cylindrical magnets as is depicted in FIG. 39. Alternatively, two or one cylindrical magnets can be disposed next to each container. In another embodiment, one cylindrical magnet can be placed between each 2-by-2 subarray (or element) of containers 1 in the container array. FIG. 40D shows an installation of cylindrical magnets 99 in structure 104.

Figure 41:
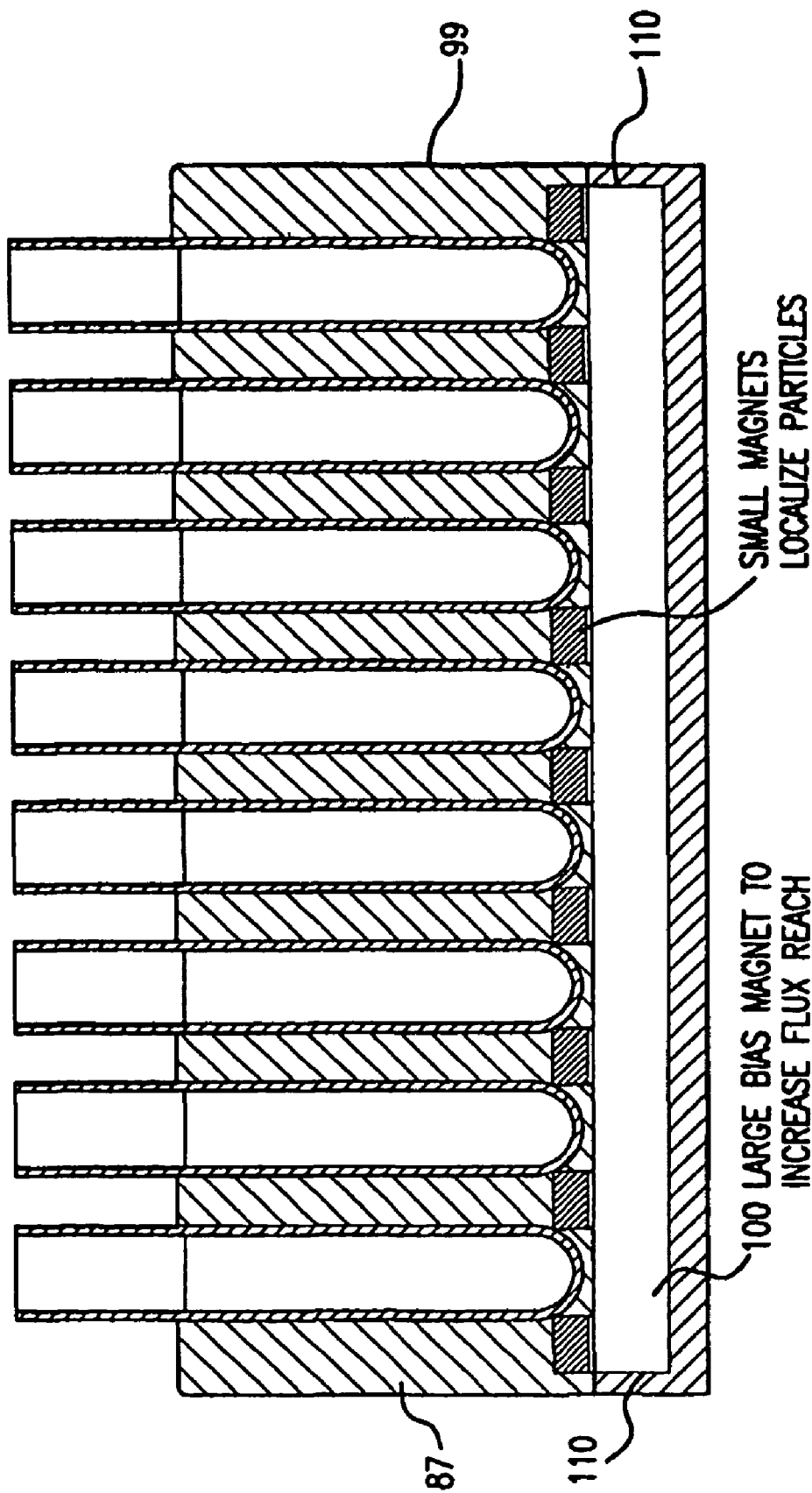
FIG. 41 is a side view of an alternate magnet configuration for use with the alternate sample prep process area of FIG. 35.

In a preferred embodiment, any of the forgoing embodiments of the magnet assemblies 87 can be combined with a large bias magnet 108 as depicted in FIG. 41. A large bias magnet spans the container array to provide an effective magnetic field originating at opposite ends of the container 1 array. The large bias magnet increases magnetic flux density at the uppermost portion of the container(s) 1. The large bias array may advantageously increase the magnetic flux density by 3 fold, more preferably 10-fold, at one-half the height of the container 1. In the depicted embodiment, an increase in magnetic flux density greater than 2 cm from the bias magnet of about 10-fold was observed in a test sample. For clarity, the containers in the embodiment depicted in FIG. 41 are about 12 cm in height. Line 110 depicts the reach of the effective reach of the magnetic flux provided by the large bias magnet.

What is claimed is:

1. An apparatus comprising:
   a first process path for isolating a nucleic acid, the first process path including temperature assembly and a magnetic assembly;
   an array of first containers positioned on the first process path, the first containers configured to receive a sample to be processed on the first process path;
   wherein each of the temperature assembly and the magnetic assembly are configured to receive the array of first containers;
   a second process path for amplification of nucleic acids, wherein the second process path is positioned vertically below the first process path; and
   a second container positioned on the second process path, the second container configured to receive an isolated item of interest from a sample processed on the first process path.

2. The apparatus of claim 1, wherein the apparatus further comprises a horizontal surface upon which the first process path is mounted, wherein the horizontal surface includes an opening adapted for the transfer of the second container to the second process path.

3. The apparatus of claim 1, wherein the second process path is enclosed in a chamber containing a vent, and the apparatus includes a pressure source fluidly connected with the chamber for causing air to flow from the chamber through the vent.

* * * * *